(12) United States Patent
Stasi et al.

(10) Patent No.: US 9,062,033 B2
(45) Date of Patent: Jun. 23, 2015

(54) CHEMICAL COMPOUNDS

(71) Applicant: Rottapharm Biotech S.r.l., Monza (IT)

(72) Inventors: Luigi Piero Stasi, Monza (IT); Lucio Claudio Rovati, Monza (IT); Roberto Artusi, Monza (IT); Fabrizio Colace, Monza (IT); Stefano Mandelli, Monza (IT); Lorenzo Perugini, Monza (IT)

(73) Assignee: Rottapharm Biotech S.R.L., Monza (IT)

( * ) Notice: Subject to any disclaimer, the term of this patent is extended or adjusted under 35 U.S.C. 154(b) by 0 days.

(21) Appl. No.: 14/366,743

(22) PCT Filed: Dec. 20, 2012

(86) PCT No.: PCT/EP2012/076447
§ 371 (c)(1),
(2) Date: Jun. 19, 2014

(87) PCT Pub. No.: WO2013/092893
PCT Pub. Date: Jun. 27, 2013

(65) Prior Publication Data
US 2014/0357653 A1    Dec. 4, 2014

(30) Foreign Application Priority Data

Dec. 21, 2011 (IT) .............. MI2011A2329

(51) Int. Cl.
| | |
|---|---|
| *C07D 417/14* | (2006.01) |
| *C07D 403/14* | (2006.01) |
| *C07D 471/04* | (2006.01) |
| *C07D 401/12* | (2006.01) |
| *C07D 413/14* | (2006.01) |
| *A61K 31/505* | (2006.01) |
| *A61K 31/4439* | (2006.01) |
| *A61K 31/427* | (2006.01) |
| *C07D 401/14* | (2006.01) |
| *C07D 405/14* | (2006.01) |

(52) U.S. Cl.
CPC ............ *C07D 401/12* (2013.01); *C07D 401/14* (2013.01); *C07D 405/14* (2013.01); *C07D 413/14* (2013.01); *C07D 417/14* (2013.01); *C07D 403/14* (2013.01); *C07D 471/04* (2013.01)

(58) Field of Classification Search
USPC .......... 514/256, 275, 278, 365, 367; 544/230; 546/15; 548/147
See application file for complete search history.

(56) References Cited

FOREIGN PATENT DOCUMENTS

EP    WO 2011006960    *  1/2011    .................... 514/275

* cited by examiner

Primary Examiner — Samantha Shterengarts
(74) Attorney, Agent, or Firm — Jones Day

(57) ABSTRACT

The invention relates to a novel compound of formula (I) or a stereoisomer, or a racemate or a mixture or a pharmaceutically acceptable salt thereof: wherein: R is phenyl or a 5- or 6-membered heteroaryl ring containing 1 to 3 heteroatoms selected from S, N and O, such rings may be optionally substituted with n groups Q; Q is selected from a group consisting of: C1-C4 alkyl, halogen, halo C1-C4 alkyl, C1-C4 alkoxy, CN, $SO_2CH_3$ or a group $—O[(CR_1R_2]pQ_1$; or Q may be a group $Q_2$; $Q_1$ is phenyl, which may be optionally substituted with n substituents selected from a group consisting of: C1-C4 alkyl, halogen, halo C1-C4 alkyl, C1-C4 alkoxy, CN, or a group $Q_2$; or corresponds to 2,2-difluoro-benzo[d][1,3]dioxol-4-yl; Q2 is a 5- or 6-membered heteroaryl containing at least one nitrogen atom, which may optionally substituted with n substituents selected from a group consisting of: C1 C1-C4 alkyl, halogen, halo C1-C4 alkyl, C1-C4 alkoxy, CN; P is a 6-membered heteroaryl or a 8-1 1 membered bicyclic heteroaryl group, which may be substituted with n substituents selected from a group consisting of: C1-C4 alkyl, halogen, halo C1-C4 alkyl, C1-C4 alkoxy, CN; $R_1$ is hydrogen or C1-C3 alkyl; $R_2$ is hydrogen or C1-C3 alkyl; n is 1, 2 or 3; p is 0, 1 or 2; and with the proviso that when R corresponds to phenyl, P is substituted by at least one $CF_3$; processes for the preparation of those compounds, pharmaceutical compositions containing one or more compounds of formula (I) and their use as dual antagonists of the Orexin 1 and Orexin 2 receptors.

(I)

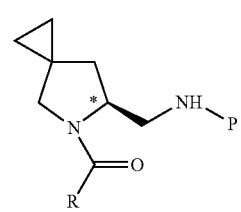

7 Claims, No Drawings

CHEMICAL COMPOUNDS

This application is a national stage application of International Application No. PCT/EP2012/076447, filed Dec. 20, 2012, which claims the benefit of Italian Patent Application No. MI2011A002329, filed Dec. 21, 2011, each of which is incorporated herein by reference in its entirety.

FIELD OF THE INVENTION

The invention relates to novel spiro aminic derivatives and their use as pharmaceuticals. The invention also concerns a process for the preparation of those compounds, pharmaceutical compositions containing one or more compounds of formula (I) and their use as dual antagonists of the Orexin 1 and Orexin 2 receptors.

BACKGROUND OF THE INVENTION

Orexin (or hypocretin) signalling is mediated by two receptors and two peptide agonists. The two orexin peptides (orexin A and orexin B) herein after referred to as orexins, bind to two high affinity receptors, termed Orexin-1 and Orexin-2 receptors. The Orexin-1 receptor is selective in favour of orexin A, while the Orexin-2 receptor binds both orexins with similar affinities. The orexins, are cleavage products of the same gene, prepro orexin. In the central nervous system neurons expressing prepro-orexin, the precursor from which orexin is produced, are found in the periformical nucleus, the dorsal hypothalamus and the lateral hypothalamus (C. Peyron et al., J. Neurosci., 1998, 18(23), 9996-10015). Orexinergic cells in these nuclei project to many areas of the brain, extending rostrally to the olfactory bulbs and caudally to the spinal cord (van den Pol, A. N. et al., J. Neuroscience., 1999, 19(8), 3171-3182).

The broad CNS distribution of orexin projections and neurons expressing orexin receptors is suggestive of orexin involvement in a number of physiological functions including; feeding, drinking, arousal, stress, reward, metabolism and reproduction (T. Sakurai, Nature Reviews Neuroscience, 2007, 8(3), 171-181). The targeted necrosis of cells expressing prepro-orexin suggests the most physiologically important roles of the orexins are likely to be effects on arousal, feeding and metabolism (J. Hara et al., Neuron, 2001, 30, 345-354). A prominent orexin neuronal projection via the vagus nerve probably mediates central orexin effects on cardiac parameters (W. K. Samson et al., Brain Res., 1999, 831, 248-253; T. Shirasaka et al., Am. J. Physiol., 1999, 277, R1780-R1785; C.-T. Chen et al., Am. J. Physiol., 2000, 278, R692-R697), gastric acid secretion and gastric motility (A. L. Kirchgessner and M.-T. Liu, Neuron, 1999, 24, 941-951; N. Takahashi et al., Biochem. Biophys. Res. Commun., 1999, 254, 623-627). Several lines of evidence indicate that the orexin system is an important modulator of arousal. Rodents administered orexins intracerebroventricularly spend more time awake (Piper et al., J. Neurosci. 2000, 12, 726-730). Orexin-mediated effects on arousal have been linked to orexin neuronal projections to histaminergic neurons in the tuberomammillary nucleus (TMN) (Yamanaka et al., Biochem. Biophys. Res. Comm. 2002, 290, 1237-1245). TMN neurons express the orexin-2 receptor primarily, and the orexin-1 receptor to a lesser extent. Rodents whose prepro orexin gene has been knocked out, or whose orexigenic neurons have been lesioned, display altered sleep/wake cycles similar to narcolepsy (Chemelli et al., Cell 1999, 98, 437-451; Hara et al., 2001, supra). Dog models of narcolepsy have been shown to have mutant or non-functional orexin-2 receptors (Lin et al., Cell 1999, 98, 365-376). Human narcolepsy appears to be linked to deficient orexin signalling, likely related to immune ablation of orexinergic neurons in the lateral hypothalamus (Mignot et al., Am. J. Hum. Genet. 2001, 68: 686-699; Minot & Thorsby, New England J. Med. 2001, 344, 692), or, in rare cases, to mutations in the orexin-2 gene (Peyron et al., Nature Med. 2000, 6, 991-997). The disclosure that rats, dogs and humans treated with the dual orexin-1/2 receptor antagonist, ACT-078573 (Brisbare-Roch et al., Nature Medicine, 2007, 13, 150-155) exhibited decreased alertness together with characteristic clinical and EEG (electroencephalographic) signs of sleep provides evidence to support a role for the orexin system in the regulation of arousal, sleep and wake states. EEG data indicates that orexin-2 may be more important than orexin-1 in the modulation of sleep/wake (P. Malherbe et al., Molecular Pharmacology (2009) 76(3):618-31; C. Dugovic et al., J. Pharmacol. Exp. Then, 2009, 330(1), 142-151). Disorders of the sleep-wake cycle are therefore likely targets for orexin-2 receptor antagonist therapy. Examples of such disorders include sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic pain). The orexin system also interacts with brain dopamine systems. Intracerebroventricular injections of orexins in mice increase locomotor activity, grooming and stereotypy; these behavioural effects are reversed by administration of D2 dopamine receptor antagonists (Nakamura et al., Brain Research, 873(1), 181-7). Therefore, orexin-2 modulators may be useful to treat various neurological disorders; e.g., agonists or up-regulators to treat catatonia, antagonists or down-regulators to treat Parkinson's disease, Tourette's syndrome, anxiety, delirium and dementias. Recent evidence indicates a role for orexin in the pathogenesis of Alzheimers disease (Kang et al, Science Express, 2009, 1-10). Brain interstitial fluid levels of amyloid-beta were demonstrated to fluctuate diurnally in both humans and rodents with sleep deprivation in rodents leading to significant increases in brain interstitial fluid levels of amyloid-beta. Infusion of a dual orexin antagonist in rodents suppressed interstitial levels of amyloid-beta and abolished the natural diurnal variation of amyloid-beta. The reduction of interstitial fluid amyloid-beta levels is correlated with reduced amyloid plaque formation, a hallmark of Alzheimer's disease, and consequently the regulation of sleep time could potentially inhibit amyloid-beta aggregation and slow the progression of Alzheimer's disease.

Orexin neurons project to many regions of the brain associated with reward function (T. Sakurai, supra) and research, focusing on animal models of drug intake, reward, and reinstatement, has expanded the link between the orexin system and addiction. A comprehensive set of data suggest that drugs of abuse activate the orexin system, which in turn enhances drug reward or drug seeking (G. Aston-Jones et al., Neuropharmacology, 2009, 56 (Suppl 1) 112-121. Thus interactions between nicotine (J. K. Kane et al., Endocrinology, 2000, 141 (10), 3623-3629; J. K. Kane et al., Neurosci. Lett, 2001, 298(1), 1-4), morphine (D. Georgescu, et al., J. Neurosci., 2003, 23(8), 3106-3111) and amphetamine (C. J. Winrow et al., Neuropharmacology, 2010, 58(1), 185-94) and the orexin system have been demonstrated. Additional studies from a number of laboratories have demonstrated an important relationship between the Orexin system and ethanol consumption. As examples, ethanol consumption in an alcohol-preferring strain of rat was shown to up regulate Orexin mRNA in the lateral hypothalamus and that an Orexin-1 receptor antagonist reduced operant responding for ethanol (Lawrence, et. al., Br. J. Pharmacol., 2006, 148, 752-759). Treatment with an orexin-1 antagonist has also been shown to decrease operant responding for ethanol (Richards, et. al., Psychopharmacology, 2008, 199 (1), 109-117). Other studies have demonstrated increased Fos activation of orexin neurons following contextual reinstatement to ethanol seeking (Dayas, et. al., Biol. Psychiatry, 2008, 63 (2), 152-157 and Hamlin, et. al., Neuroscience, 2007, 146, 525-536). Studies have also shown increased ethanol consumption following Orexin infusion into the paraventricular nucleus of the hypothalamus or in the lateral hypothalamus (Schneider, et. al., Alcohol. Clin. Exp. Res., 2007, 37(11), 1858-1865). These studies provide evidence that modulation of the Orexin system effects alcohol preference and therefore Orexin receptor antagonists are likely to be useful for the treatment of alcoholism.

Orexins and their receptors have been found in both the myenteric and submucosal plexus of the enteric nervous system, where orexins have been shown to increase motility in vitro (Kirchgessner & Liu, Neuron 1999, 24, 941-951) and to stimulate gastric acid secretion in vitro (Takahashi et al., Biochem. Biophys. Res. Comm. 1999, 254, 623-627). Orexin mediated effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhoea and gastroesophageal reflux. Body weight may also be affected by orexin-mediated regulation of appetite and metabolism (T. Sakurai et al., Cell, 1998, 92(4), 573-585; T. Sakurai, Reg. Pept, 1999, 85(1), 25-30). Some effects of orexin on metabolism and appetite may be mediated in the gut, where, as mentioned, orexins alter gastric motility and gastric acid secretion. Orexin receptor antagonists therefore are likely to be useful in treatment of overweight or obesity and conditions related to overweight or obesity, such as insulin resistance, type II diabetes, hyperlipidemia, gallstones, angina, hypertension, breathlessness, tachycardia, infertility, sleep apnoea, back and joint pain, varicose veins and osteoarthritis. Conversely, orexin receptor agonists are likely to be useful in treatment of underweight and related conditions such as hypotension, bradycardia, amenorrhea and related infertility, menopause and eating disorders such as anorexia and bulimia. Intracerebroventricularly administered orexins have been shown to increase mean arterial pressure and heart rate in freely moving (awake) animals (Samson et al., Brain Res. 1999, 831, 248-253; Shirasaka et al., Am. J. Physiol. 1999, 277, R1780-R1785) and in urethane-anesthetized animals (Chen et al., Am. J. Physiol. 2000, 278, R692-R697), with similar results.

Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor antagonists, in one embodiment modulators of the orexin-2 receptor, will be of great advantage in the development of therapeutic agents for the treatment of a wide variety of disorders that are mediated through these receptor systems.

In the International patent application WO2011/006960 spiro amino selective Orexin 1 antagonists of the following general formula have been disclosed:

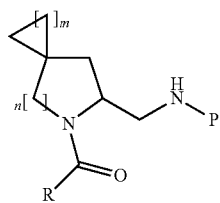

in which m and n may be both 1 and R and P are as defined.

It has been found that modifying the decoration of the compounds when R is phenyl it is possible to change the activity of such compounds at the OX2 receptors.

There remains a need, however, for potent orexin dual receptor antagonists with desirable pharmaceutical properties The object of the present invention is to provide spiro amino compounds with dual antagonist activity at the Orexin 1 and Orexin 2 receptors.

SUMMARY OF THE INVENTION

The present invention provides a compound of formula (I) or a pharmaceutically acceptable salt thereof:

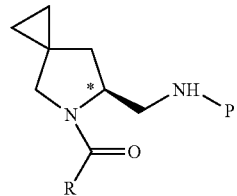

(I)

R is phenyl or a 5- or 6-membered heteroaryl ring containing 1 to 3 heteroatoms selected from S, N and O, such rings may be optionally substituted with n groups Q;

Q is selected from a group consisting of: C1-C4 alkyl, halogen, halo C1-C4 alkyl, C1-C4 alkoxy, CN, $SO_2CH_3$ or a group $—O[(CR_1R_2]pQ_1$; or Q may be a group $Q_2$;

$Q_1$ is phenyl, which may be optionally substituted with n substituents selected from a group consisting of: C1-C4 alkyl, halogen, halo C1-C4 alkyl, C1-C4 alkoxy, CN, or a group $Q_2$; or $Q_1$ corresponds to 2,2-difluoro-benzo[d][1,3]dioxol-4-yl;

$Q_2$ is a 5- or 6-membered heteroaryl containing at least one nitrogen atom, which may optionally substituted with n substituents selected from a group consisting of: C1 C1-C4 alkyl, halogen, halo C1-C4 alkyl, C1-C4 alkoxy, CN;

P is a 6-membered heteroaryl or a 8-11 membered bicyclic heteroaryl group, which may be substituted with n substituents selected from a group consisting of: C1-C4 alkyl, halogen, halo C1-C4 alkyl, C1-C4 alkoxy, CN;

$R_1$ is hydrogen or C1-C3 alkyl;

$R_2$ is hydrogen or C1-C3 alkyl;

n is 1, 2 or 3;

p is 0, 1 or 2; and with the proviso that when R corresponds to phenyl, P is substituted by at least one $CF_3$.

Compounds of formula (I) are provided as (S) enantiomers at the chiral carbon represented with an asterisk (*). It is intended in the context of the present invention that stereochemical isomers enriched in configuration (S) of formula (I) correspond in one embodiment to at least 90% e.e. In another embodiment the isomers correspond to at least 95% e.e. In another embodiment the isomers correspond to at least 99% e.e.

This invention includes in its scope of protection all the possible isomers and racemic mixtures. Wherever should be present further symmetry centres, this invention includes all the possible diastereoisomers and relative mixtures as well.

In a first embodiment, the present invention provides a compound of formula (II), corresponding to a compound of formula (I) in which R is a thiazolinyl derivative, P, Q and n are defined as above.

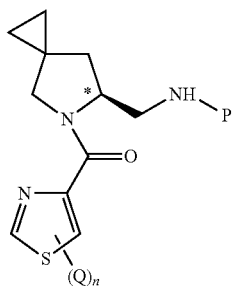

(II)

In a second embodiment, the present invention provides a compound of formula (III), corresponding to a compound of formula (I) in which R is a pyridinyl derivative, P, Q and n are defined as above.

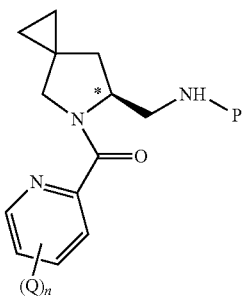

(III)

In a third embodiment, the present invention provides a compound of formula (IV), corresponding to a compound of formula (I) in which R is a phenyl derivative, $P_1$ is a pyridinyl derivative which is substituted by at least a group —$CF_3$, Q and n are defined as above.

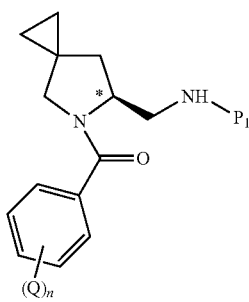

(IV)

In another aspect the invention concerns pharmaceutical compositions comprising a compound of formula (I) and a pharmaceutically acceptable carrier.

In another aspect the invention concerns a compound of Formula (I) as medicament; in particular it concerns its use for the manufacturing of a medicament for the treatment of pathologies where an antagonist of the OX1/OX2 antagonist is needed, such as the treatment of obesity, sleep disorders, compulsive disorders, drug dependency, and schizophrenia.

DETAILED DESCRIPTION OF THE INVENTION

The present invention thus provides a compound of formula (I) or a pharmaceutically acceptable salt thereof:

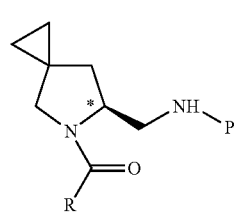

(I)

wherein:
R is phenyl or a 5- or 6-membered heteroaryl ring containing 1 to 3 heteroatoms selected from S, N and O, such rings may be optionally substituted with n groups Q;
Q is selected from a group consisting of: C1-C4 alkyl, halogen, halo C1-C4 alkyl, C1-C4 alkoxy, CN, $SO_2CH_3$ or a group —O[($CR_1R_2$)p$Q_1$]; or Q may be a group $Q_2$;
$Q_1$ is phenyl, which may be optionally substituted with n substituents selected from a group consisting of: C1-C4 alkyl, halogen, halo C1-C4 alkyl, C1-C4 alkoxy, CN, or a group $Q_2$; or $Q_1$ corresponds to 2,2-difluoro-benzo[d][1,3]dioxol-4-yl;
$Q_2$ is a 5- or 6-membered heteroaryl containing at least one nitrogen atom, which may optionally substituted with n substituents selected from a group consisting of: C1 C1-C4 alkyl, halogen, halo C1-C4 alkyl, C1-C4 alkoxy, CN;
P is a 6-membered heteroaryl or a 8-11 membered bicyclic heteroaryl group, which may be substituted with n substituents selected from a group consisting of: C1-C4 alkyl, halogen, halo C1-C4 alkyl, C1-C4 alkoxy, CN;
$R_1$ is hydrogen or C1-C3 alkyl;
$R_2$ is hydrogen or C1-C3 alkyl;
n is 1, 2 or 3;
p is 0, 1 or 2; and
with the proviso that when R corresponds to phenyl, P is substituted by at least one $CF_3$.

The term "5- or 6-membered heteroaryl ring" refers to a monocyclic 5- or 6-membered heterocyclic group containing 1 to 3 heteroatoms and having at least one heteroatom selected from nitrogen, oxygen and sulfur, and containing at least 1 carbon atom. Examples of 5 and 6-membered heteroaryl groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "8,11-membered bicyclic heteroaryl" as used herein means an aromatic bicyclic heterocycle ring of 8 to 11 members and having at least one heteroatom selected from nitrogen, oxygen and sulfur, and containing at least 1 carbon atom. Representative 8, to 11 membered bicyclic heteroaryl groups include (but are not limited to): benzofuranyl, benzothiophenyl, indolyl, isoindolyl, azaindolyl, quinolinyl, isoquinolinyl, benzoxazolyl, benzimidazolyl, benzothiazolyl, quinazolinyl and phthalazinyl.

The term "C1-C4 alkyl" refers to an alkyl group having from one to four carbon atoms, in all isomeric forms, such as methyl, ethyl, propyl, isopropyl, butyl, isobutyl, sec-butyl and tert-butyl. The term "n-C1-C4 alkyl" refers to the unbranched alkyls as defined above.

The term "C1-C4 alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylene-diamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and for be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Hereinafter, compounds of formula (I) and their pharmaceutically acceptable salts, and solvates defined in any aspect of the invention (except intermediate compounds in chemical processes) are referred to as "compounds of the invention".

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers and mixtures thereof. Certain of the substituted heteroaromatic groups included in compounds of formula (I) may exist in one or more tautomeric forms. The present invention includes within its scope all such tautomeric forms, including mixtures.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertible in the mammalian (e.g. human) body to the inventive compounds are however included.

In a first embodiment, the present invention provides a compound of formula (II), corresponding to a compound of formula (I) in which R is a thiazolinyl derivative, P, Q and n are defined as above.

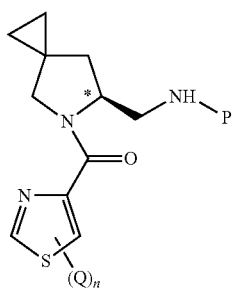

(II)

In a further embodiment compounds the present invention provides a compound of formula (II) in which:

P is selected among a 2-pyridyl derivative, 2-isoquinolinyl derivative, 2-pyrimidyl derivative, 2-benzothiazolyl derivative, 2-benzoxazolyl derivative which may be substituted with n substituents selected from a group consisting of: C1-C4 alkyl, halogen, halo C1-C4 alkyl, C1-C4 alkoxy, CN.

In a second embodiment, the present invention provides a compound of formula (III), corresponding to a compound of formula (I) in which R is a pyridinyl derivative, P, Q and n are defined as above.

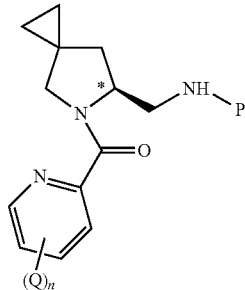

(III)

In a further embodiment the present invention provides a compound of formula (III) in which:
P is selected among a 2-pyridyl derivative, 2-pyrazinyl derivative, 2-benzoxazolyl derivative which may be substituted with n substituents selected from a group consisting of: C1-C4 alkyl, halogen, halo C1-C4 alkyl, C1-C4 alkoxy, CN.

In a third embodiment, the present invention provides a compound of formula (IV), corresponding to a compound of formula (I) in which R is a phenyl derivative, $P_1$ is a pyridinyl derivative which is substituted by at least a group —CF$_3$, Q and n are defined as above.

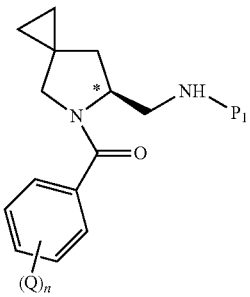

(IV)

In a further embodiment the present invention provides a compound of formula (IV) in which:
P is a 2-pyridyl derivative, which is substituted with at least a —CF3 group and may be further substituted with n−1 substituents selected from a group consisting of: C1-C4 alkyl, halogen, halo C1-C4 alkyl, C1-C4 alkoxy, CN.

Example compounds of the invention include:
(S)-(6-(((5-chloropyridin-2-yl)amino)methyl)-5-azaspiro [2.4]heptan-5-yl)(2-methyl-5-phenylthiazol-4-yl)methanone;
(S)-(2-methyl-5-phenylthiazol-4-yl)(6-(((6-methylpyridin-2-yl)amino)methyl)-5-azaspiro[2.4]heptan-5-yl)methanone;
(S)-(2-methyl-5-phenylthiazol-4-yl)(6-(((5-(trifluoromethyl)pyridin-2-yl)amino)methyl)-5-azaspiro[2.4]heptan-5-yl)methanone;

(S)-(6-((isoquinolin-1-ylamino)methyl)-5-azaspiro[2.4]heptan-5-yl)(2-methyl-5-phenylthiazol-4-yl)methanone;
(S)-(6-(((4,6-dimethylpyrimidin-2-yl)amino)methyl)-5-azaspiro[2.4]heptan-5-yl)(2-methyl-5-phenylthiazol-4-yl)methanone;
(S)-(6-(((5-chloropyrimidin-2-yl)amino)methyl)-5-azaspiro[2.4]heptan-5-yl)(2-methyl-5-phenylthiazol-4-yl)methanone;
(S)-(6-methyl-3-(pyrimidin-2-yl)pyridin-2-yl)(6-(((5-(trifluoromethyl)pyridin-2-yl)amino)methyl)-5-azaspiro[2.4]heptan-5-yl)methanone;
(S)-(6-methyl-3-phenylpyridin-2-yl)(6-(((5-(trifluoromethyl)pyridin-2-yl)amino)methyl)-5-azaspiro[2.4]heptan-5-yl)methanone;
(S)-(6-(((5-chloro-3-fluoropyridin-2-yl)amino)methyl)-5-azaspiro[2.4]heptan-5-yl)(6-methyl-3-(pyrimidin-2-yl)pyridin-2-yl)methanone;
(S)-(6-(((3-fluoro-5-(trifluoromethyl)pyridin-2-yl)amino)methyl)-5-azaspiro[2.4]heptan-5-yl)(6-methyl-3-(pyrimidin-2-yl)pyridin-2-yl)methanone;
(S)-(6-(((3-fluoro-5-(trifluoromethyl)pyridin-2-yl)amino)methyl)-5-azaspiro[2.4]heptan-5-yl)(6-methyl-3-phenylpyridin-2-yl)methanone;
(S)-(3-(4-fluorophenyl)-6-methylpyridin-2-yl)(6-(((5-(trifluoromethyl)pyridin-2-yl)amino)methyl)-5-azaspiro[2.4]heptan-5-yl)methanone;
(S)-(6-(((3-chloro-5-(trifluoromethyl)pyridin-2-yl)amino)methyl)-5-azaspiro[2.4]heptan-5-yl)(6-methyl-3-(pyrimidin-2-yl)pyridin-2-yl)methanone;
(S)-(6-methyl-3-(pyrimidin-2-yl)pyridin-2-yl)(6-(((5-(trifluoromethyl)pyrazin-2-yl)amino)methyl)-5-azaspiro[2.4]heptan-5-yl)methanone;
(S)-(6-methyl-3-(4-methyl-1H-pyrazol-1-yl)pyridin-2-yl)(6-(((5-(trifluoromethyl)pyridin-2-yl)amino)methyl)-5-azaspiro[2.4]heptan-5-yl)methanone;
(S)-(6-methyl-3-(3-methyl-1H-pyrazol-1-yl)pyridin-2-yl)(6-(((5-(trifluoromethyl)pyridin-2-yl)amino)methyl)-5-azaspiro[2.4]heptan-5-yl)methanone;
(S)-(3-(benzyloxy)-6-methylpyridin-2-yl)(6-(((5-(trifluoromethyl)pyridin-2-yl)amino)methyl)-5-azaspiro[2.4]heptan-5-yl)methanone;
(S)-(6-(((6-fluorobenzo[d]thiazol-2-yl)amino)methyl)-5-azaspiro[2.4]heptan-5-yl)(2-methyl-5-phenylthiazol-4-yl)methanone;
(S)-(6-(((6-chlorobenzo[d]thiazol-2-yl)amino)methyl)-5-azaspiro[2.4]heptan-5-yl)(2-methyl-5-phenylthiazol-4-yl)methanone;
(S)-(3-((2,3-difluorobenzyl)oxy)-6-methylpyridin-2-yl)(6-(((5-(trifluoromethyl)pyridin-2-yl)amino)methyl)-5-azaspiro[2.4]heptan-5-yl)methanone;
(S)-(3-((4-fluorobenzyl)oxy)-6-methylpyridin-2-yl)(6-(((5-(trifluoromethyl)pyridin-2-yl)amino)methyl)-5-azaspiro[2.4]heptan-5-yl)methanone;
(S)-(3-((2,4-difluorobenzyl)oxy)-6-methylpyridin-2-yl)(6-(((5-(trifluoromethyl)pyridin-2-yl)amino)methyl)-5-azaspiro[2.4]heptan-5-yl)methanone;
(S)-(3-((3,5-difluorobenzyl)oxy)-6-methylpyridin-2-yl)(6-(((5-(trifluoromethyl)pyridin-2-yl)amino)methyl)-5-azaspiro[2.4]heptan-5-yl)methanone;
(S)-(2,2-difluorobenzo[d][1,3]dioxol-4-yl)(6-(((5-(trifluoromethyl)pyridin-2-yl)amino)methyl)-5-azaspiro[2.4]heptan-5-yl)methanone;
(S)-(5-chloro-2-(pyrimidin-2-yl)phenyl)(6-(((5-(trifluoromethyl)pyridin-2-yl)amino)methyl)-5-azaspiro[2.4]heptan-5-yl)methanone;
(S)-(6-((benzo[d]oxazol-2-ylamino)methyl)-5-azaspiro[2.4]heptan-5-yl)(2-methyl-5-phenylthiazol-4-yl)methanone;
(S)-(3-methyl-2-(pyrimidin-2-yl)phenyl)(6-(((5-(trifluoromethyl)pyridin-2-yl)amino)methyl)-5-azaspiro[2.4]heptan-5-yl)methanone;
(S)-(4-(methylsulfonyl)-[1,1'-biphenyl]-2-yl)(6-(((5-(trifluoromethyl)pyridin-2-yl)amino)-methyl)-5-azaspiro[2.4]heptan-5-yl)methanone;

or their pharmaceutically acceptable salts thereof.

A further aspect of this invention concerns a process for the preparation of a compound of formula (I) comprising the following steps represented in the scheme below:

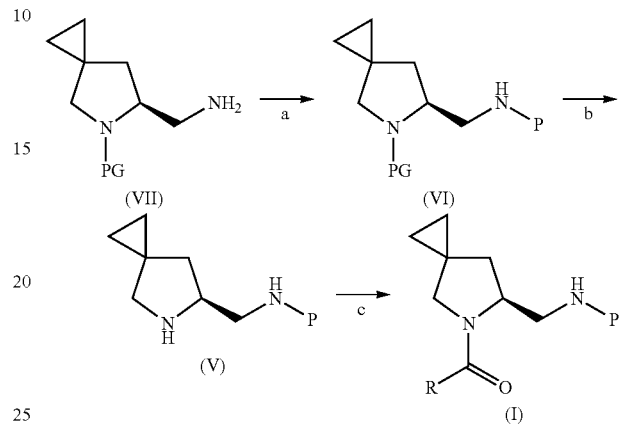

Step a) means adding a compound of formula P—X, where P is defined as above and X is a leaving group, to the compound of formula (VII) in which PG means a suitable protective group of the nitrogen such the BOC group to obtain a compound of Formula (VI);

Step b) means cleaving the protecting group (PG), such as the BOC group from the compound of formula (V) to obtain a compound of Formula (IV);

Step c) means reacting a compound of Formula (IV) with RCOOH or a reactive derivative thereof (such as anhydride or acyl chloride) in the presence of coupling reagents in the presence of a base, where R is defined as above.

"Leaving group" is as understood by a skilled chemist, i.e. a group which can be displaced by a nucleophile in e.g. a $S_N2$, $S_N1$ or $S_NAr$ type reaction, such as an halogen or a reactive residue of a alkyl/aryl sulphonic acid, for example mesylate, tosylate, triflate.

A further aspect of this invention concerns a process for the preparation of a compound of Formula (I), prepared according to WO2011006960. Alternatively, the preparation of a compound of Formula (VII), which was obtained from a compound of formula (VIII) (prepared according to WO 2008101665) is represented in the scheme below (scheme 1):

Scheme 1

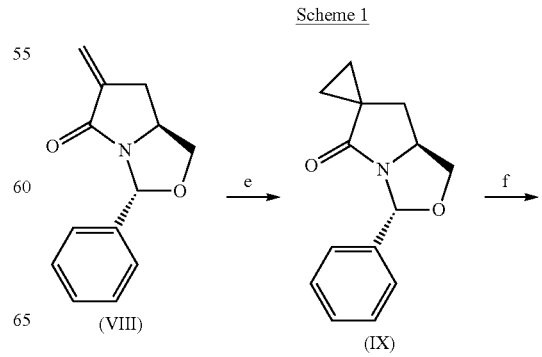

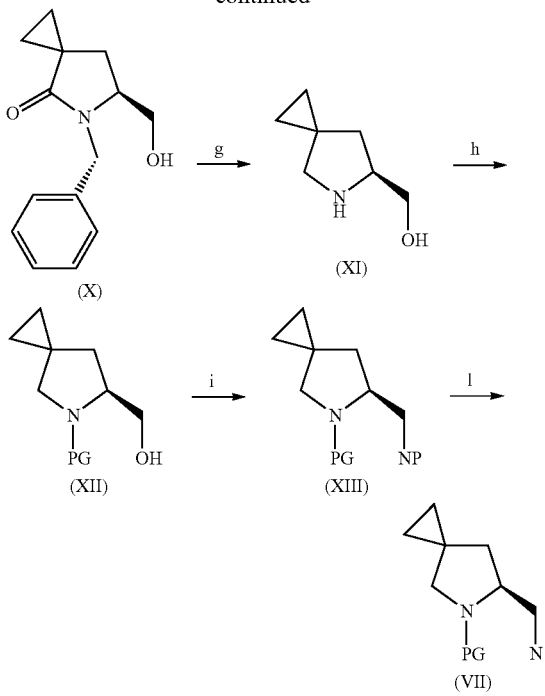

Step e) means reacting a compound of formula (VIII) with a suitable reagent, such as trimethylsulfoxonium iodide, to obtain a compound of formula (IX);
Step f) means reducing with an appropriate reagent, such as LiAlH$_4$, to obtain a compound of formula (X);
Step g) means deprotection of a compound of formula (X) under an atmosphere of hydrogen by using suitable catalyst, such as Pd/C, to obtain an amino alcohol of formula (XI);
Step h) means introducing a protecting group, such as BOC, to obtain a compound of formula (XII);
Step i) means converting the alcohol with an amine by using a precursor, such as phtalimide, under Mitsunobu conditions to obtain a compound of formula (XIII);
Step l) means deprotection of the phtalimide by using a suitable reagent, such as hydrazine, to obtain a compound of formula (VII);

The compounds of formula (I) or their pharmaceutically acceptable salts can be used as medicaments, in particular as antagonists of the Orexin 1/Orexin 2 receptors. They could be used in combination with a pharmaceutically acceptable carrier and, optionally, with suitable excipients, to obtain pharmaceutical compositions. The term "pharmaceutically acceptable carrier" means solvents, carrier agents, diluting agents and the like which are used in the administration of compounds of the invention. Such pharmaceutical compositions can be administered by parenteral, oral, buccal, sublingual, nasal, rectal, topical or transdermal administration. Compositions of this invention suitable for the oral administration will be conveniently discrete units such as tablets, capsules, cachet, powders or pellets, or as liquid suspension.

The tablets can contain also suitable excipients routinely used in pharmaceutical field such as pre-gelatinised starch, microcrystalline cellulose, sodium glycolate starch, talc, lactose, magnesium stearate, sucrose, stearic acid, mannitol. Compositions for parenteral administration conveniently include sterile preparations. Compositions for topical administration may conveniently be formulated as creams, pastes, oils, ointments, emulsions, foams, gels, drops, spray solutions and transdermal patches.

The production of the pharmaceutical compositions can be effected in a manner which will be familiar to any person skilled in the art (see for example Remington, The Science and Practice of Pharmacy, 21 st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically effective amount of a compound of formula (I).

In treatment methods according to the invention, an effective amount of a pharmaceutical composition according to the invention is administered to a subject suffering from or diagnosed as having such disease, disorder or condition.

An "effective amount" means an amount or dose sufficient to generally bring about the desired therapeutic or prophylactic benefit in patients in need of such treatment for the designated disease, disorder or condition. Effective amounts or doses of the compounds of the present invention may be ascertained by routine methods such as modelling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

For avoidance of any doubt, if compounds are described as useful for the prevention or treatment of certain diseases, such compounds are likewise suitable for use in the preparation of a medicament for the prevention or treatment of said diseases.

The compounds according to formula (I) are useful for the prevention or treatment of diseases related to the orexin system.

Such diseases related to the orexin system may be selected from the group consisting of all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

In a sub-embodiment, such diseases related to the orexin system may be selected from the group consisting of sleep disorders that comprises all types of insomnias, narcolepsy and other disorders of excessive sleepiness, sleep-related dystonias, restless leg syndrome, sleep apnoeas, jet-lag syndrome, shift-work syndrome, delayed or advanced sleep phase syndrome or insomnias related to psychiatric disorders (notably all types of insomnias, especially primary insomnia).

In another sub-embodiment, such diseases related to the orexin system may be selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders. In another sub-embodiment, such diseases related to the orexin system may be selected from the group consisting of eating disorders that comprise metabolic dysfunction; dysregulated appetite control; compulsive obesities; emeto-bulimia or anorexia nervosa. In another sub-embodiment, such diseases related to the orexin system may be selected from the group consisting of all types of addictions (especially psychoactive substance use, abuse, seeking and reinstatement) that comprise all types of psychological or physical addictions and their related tolerance and dependence components.

In another sub-embodiment, such diseases related to the orexin system may be selected from the group consisting of menopause; Eating disorders may be defined as comprising metabolic dysfunction; dysregulated appetite control; compulsive obesities; emeto-bulimia or anorexia nervosa.

Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance. Addictions may be defined as addiction to one or more rewarding stimuli, notably to one rewarding stimulus. Such rewarding stimuli may be of either natural or synthetic origin. Psychoactive substance use, abuse, seeking and reinstatement are defined as all types of psychological or physical addictions and their related tolerance and dependence components.

Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

Besides, any characteristics described in this invention for the compounds of formula (I) (whether for the compounds themselves, salts thereof, compositions containing the compounds or salts thereof, uses of the compounds or salts thereof, etc.) apply mutatis mutandis to compounds of formula (II) and (III).

EXPERIMENTAL SECTION

The invention will be now detailed by means of the following examples relating to the preparation of some invention compounds and to the evaluation of their activity against OX1 receptor and OX2 receptor.

In the procedure that follows, after the starting materials, reference to a description is typically provided. The starting material may not necessarily have been prepared from the description referred to. The stereochemistry of the Examples has been assigned on the assumption that the absolute configuration centers are retained.

Reagents used in the following examples were commercially available from various suppliers (for example Sigma-Aldrich, Acros or Apollo scientific) and used without further purifications. Solvents were used in dry form. Reactions in anhydrous environment were run under a positive pressure of dry N2.

Microwave reactions were run on a Biotage Initiator 2.5 instrument.

Proton Nuclear Magnetic Resonance (1H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal.

Mass spectra (MS) were run on a Ion Trap Thermo LCQ classic spectrometer, operating in positive ES(+) and negative ES(−) ionization mode.

UPLC spectra were performed on a Waters Acquity UPLC-SQD instrument using an Acquity UPLC-BEH C18 column (1.7 μM, 50×2.1 mm).

Flash silica gel chromatography was performed on Biotage automatic flash chromatography systems (Sp1 and Isolera systems) using Biotage silica cartridges.

Thin layer chromatography was carried out using Merck TLC plates Kieselgel 60F-254, visualized with UV light, aqueous permanganate solution, iodine vapours.

The following abbreviations are used herein: DEAD:diethylazodicarboxylate; DIPEA: N,N-diisopropylethylamine; HOBT: hydroxybenzotriazole hydrate; Boc: terbutyloxycarbonyl; DCM: dichloromethane; TFA: trifluoroacetic acid; TMEDA: N,N,N',N'-Tetramethylethylenediamine; DMF: dimethylformamide; NMP: N-methylpyrrolidinone; THF: tetrahydrofuran; EDCI: N-(3-Dimethylaminopropyl)-N'-ethylcarbodiimide; HBTU: O-(Benzotriazol-1-yl)-N,N,N',N'-tetramethyluronium hexafluorophosphate; RT: room temperature; dppf: 1,1'-Bis(diphenylphosphino)ferrocene; DMAP: dimethylamino pyridine; LDA: lithium diisopropylammide; PTSA: para-toluene sulphonic acid; DBU: 1,8-Diazabicyclo[5.4.0]undec-7-ene; MsCl: Methanesulfonyl chloride; EDTA: Ethylenediaminetetraacetic acid; TEMPO: Tetramethylpiperidine 1-oxyl.

Description 1

(3'R, 7a'S)-3'-phenyldihydro-1'H-spiro[cyclopropane]-1,6'-pyrrolo[1,2-c][1,3]oxazol-5'-one (D1)

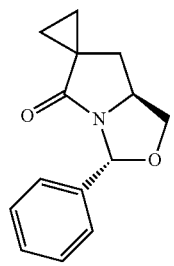 [SMILES: O=C1N2[C@H](CO[C@@H]2c2ccccc2)CC12CC2]

To the suspension of NaH (2.90 g, 72.5 mmol) in DMF (100 mL) trimethylsulfoxonium iodide (17.5 g, 79.7 mmol) was added at 0° C. under a constant current of dry N2 and the mixture was stirred at 0° C. for 1 hour. A solution of (3R, 7aS)-6-Methylene-3-phenyl-tetrahydro-pyrrolo[1,2-c]oxazol-5-one (prepared according to WO 2008101665) (15.6 g, 72.5 mmol) in DMF (30 mL) was slowly added to the mixture at 0° C. and the latter stirred at room temperature for 3 hours. H₂O was added and the reaction was extracted with EtOAc. The organic layer was washed with brine, dried over Na₂SO₄, filtered and concentrated to give a crude mixture which was purified by column chromatography (petroleum ether/ethyl acetate=4:1) to give the title compound as white solid. Yield (6.90 g, 41%)

¹H NMR (400 MHz, CDCl3): δ 0.78-0.80 (m, 1H), 0.9-0.92 (m, 1H), 1.20-1.23 (m, 1H), 1.32-1.35 (m, 1H), 2.03 (dd, J=3.2, 13.2 Hz, 1H), 2.44 (dd, J=8.4, 13.2 Hz, 1H), 3.48 (dd, J=8.0, 9.2 Hz, 1H), 4.11-4.13 (m, 1H), 4.27 (dd, J=6.4, 7.6 Hz, 1H), 6.35 (s, 1H), 7.33-7.39 (m, 3H), 7.47-7.48 (m, 2H).

Description 2

(S)-5-Benzyl-5-aza-spiro[2.4]hept-6-yl)-methanol (D2

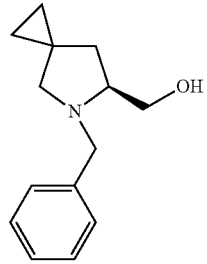 [SMILES: OC[C@@H]1CC2(CC2)CN1Cc1ccccc1]

To the suspension of lithium aluminium hydride (1.66 g, 43.6 mmol) in THF (50 mL) a solution of (D1) (5.00 g, 21.8 mmol) in THF (20 mL) was added and the mixture heated at reflux for 3 hours. After completion, the mixture was cooled to room temperature and wet Na₂SO₄ was added to quench the reaction. The solid was then filtered and the filtrate concentrated to give a crude mixture, which was purified by column chromatography (petroleum ether/ethyl acetate=3:1 to 1:1) to give the title compound as yellow oil. Yield: (3.50 g, 74%)

¹H NMR (400 MHz, CDCl3): δ 0.47-0.53 (m, 4H), 1.76 (dd, J=6.4, 12.4 Hz, 1H), 2.02 (dd, J=8.8, 12.4 Hz, 1H), 2.57 (s, 2H), 2.86 (br, 1H), 3.00-3.02 (br, 1H), 3.37 (d, J=12.8 Hz, 1H), 3.46 (dd, J=2.4, 10.8 Hz, 1H), 3.73 (dd, J=3.2, 10.8 Hz, 1H), 4.02 (d, J=12.8 Hz, 1H), 7.25-7.32 (m, 5H). LCMS [mobile phase: from 90% water (0.05% TFA) and 10% CH₃CN to 10% water (0.05% TFA) and 90% CH₃CN in 6 min, finally under these conditions for 0.5 min.] purity is >95%, Rt=2.40 min;

MS (ESI+): 218 [MH+]

Description 3

(S)-1-(5-Aza-spiro[2.4]hept-6-yl)-methanol (D3)

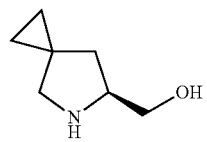

To the solution of (D2) (14.0 g, 64.5 mmol) in AcOH (50 mL) and EtOAc (50 mL), Pd/C was added (10%, 1.50 g), the mixture was stirred at room temperature under H₂ atmosphere for 3 hours. TLC detected that the starting material was consumed, at this point Pd/C was filtered and the solvent concentrated, the residue diluted with DCM (100 mL) and 2N NaOH added up to pH=8-9; the mixture was washed with DCM (100 mL) and the aqueous layer used in the next step without further purification.

Description 4

(S)-6-Hydroxymethyl-5-aza-spiro[2.4]heptane-5-carboxylic acid tert-butyl ester (D4)

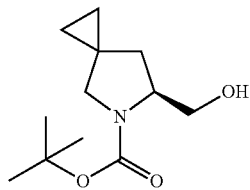 [SMILES: CC(C)(C)OC(=O)N1CC2(CC2)C[C@H]1CO]

To the above solution of (D3) in H₂O (200 mL), NaOH (3.85 g, 96.2 mmol) and (Boc)₂O (16.8 g, 77.0 mmol) were added; the mixture was stirred at room temperature for 2 hours and then extracted with DCM (50 mL×3), the organic layer was dried, filtered and concentrated to give a crude mixture, which was purified by column chromatography (petroleum ether and ethyl acetate=6:1 to 3:1) to give the title compound as colourless oil. Yield: (12.0 g, 82%).

¹H NMR (400 MHz, CDCl3): δ 0.47-0.60 (m, 4H), 1.40 (s, 9H), 1.60-1.70 (m, 1H), 2.00-2.03 (m, 1H), 2.51-2.52 (m, 1H), 3.30-3.34 (m, 2H), 3.55-3.58 (m, 1H), 3.80-3.81 (m, 1H), 4.70-4.73 (m, 1H). LCMS [mobile phase: from 80% water (0.02% NH4OAc) and 20% CH₃CN to 20% water (0.05% TFA) and 80% CH₃CN in 6 min, finally under these conditions for 0.5 min.] purity is >95%, Rt=2.80 min; MS Calcd.: 227. MS Found: 228 ([M+1]⁺).

Description 5

(S)-tert-butyl 6-((1,3-dioxoisoindolin-2-yl)methyl)-5-azaspiro[2.4]heptane-5-carboxylate (D5)

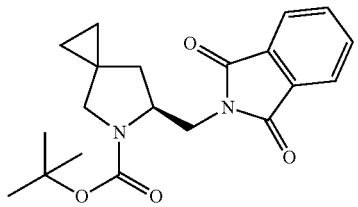 [SMILES: CC(C)(C)OC(=O)N1CC2(CC2)C[C@H]1CN1C(=O)c2ccccc2C1=O]

In a round bottomed flask under nitrogen atmosphere, triphenylphosphine (947 mg, 3.61 mmol) and phtalimide (541 mg, 3.67 mmol) were added to a solution of (S)-tert-butyl 6-(hydroxymethyl)-5-azaspiro[2.4]heptane-5-carboxylate (498 mg, 2.19 mmol) in 10 ml of dry THF. The mixture was cooled with an ice bath and a solution of DEAD 40% wt in toluene was added dropwise (1.6 ml, 3.51 mmol).

The reaction was allowed to warm up to room temperature overnight. The next morning the mixture was quenched with a small amount of MeOH; the solvent was then removed and the obtained residue was purified by flash chromatography on a 50 g silica cartridge, eluting with a step gradient: cyclohexane 100% in 2 column volumes, cyclohexane/AcOEt 95/5 in 2 column volumes, linear gradient up to 85/15 in 10 column volumes and then isocratic 85/15 in 4 column volumes.

The collected fractions were then evaporated to give 758 mg of (D5) as clear oil (yield 97%).

MS (ESI+): 357 [MH+]; 379 [MNa+]; 301, 257 (Boc fragmentation)

Description 6

(S)-tert-butyl 6-(aminomethyl)-5-azaspiro[2.4]heptane-5-carboxylate (D6)

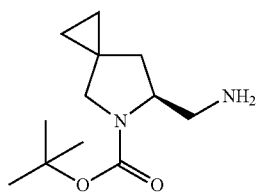 [SMILES: CC(C)(C)OC(=O)N1CC2(CC2)C[C@H]1CN]

(S)-tert-butyl 6-((1,3-dioxoisoindolin-2-yl)methyl)-5-azaspiro[2.4]heptane-5-carboxylate (752 mg, 2.11 mmol) was dissolved in 20 ml of ethanol. Hydrazine monohydrate (550 ul, 11.32 mmol) was added and the mixture was stirred at room temperature overnight.

Copious amount of a white precipitate formed, which was filtered and washed thoroughly with diethyl ether. The liquid phase was evaporated to dryness and the residue was taken up again in diethyl ether. The resulting suspension was then filtered again, further washing all the solids with ether. All the collected liquid phases were evaporated to give 420 mg of (D6) as clear viscous oil (yield 88%).

MS (ESI+): 227 [MH+]; 249 [MNa+]; 171, 127 (Boc fragmentation)

Description 7-22: (D7-22)

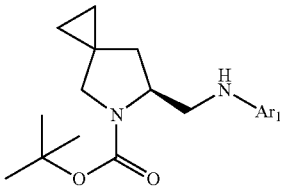

General Procedure 1

To a solution of (S)-tert-butyl 6-(aminomethyl)-5-azaspiro[2.4]heptane-5-carboxylate (prepared according to WO2011006960, 1 mmol) in isopropanol (3 ml/mmol) and N,N-diisopropylethylamine (2.2 mmol), $Ar_1$-X (where X is ortho chloro or fluoro; 1.6 mmol) was added. After complete addition, the reaction mixture was heated (microwave) at 120-150° C. until complete conversion of the starting material. The resulting mixture was evaporated to obtain a crude mixture which was purified by silica gel chromatography (petroleum ether/ethyl acetate from 10/1 to 3/1).

General Procedure 2

To the solution of (S)-tert-butyl 6-(aminomethyl)-5-azaspiro[2.4]heptane-5-carboxylate (prepared according to WO2011006960, 1 mmol) in DMF (2 ml/mmol), $K_2CO_3$ (2 mmol) and Ar1-X (where X is ortho chloro or fluoro; 1.1 mmol) were added. The reaction mixture was heated (microwave) at 80-100° C. until complete conversion of the starting material. The resulting mixture was poured in aqueous solution of NaHCO3 and extracted with AcOEt; organics were collected, washed with water, dried and evaporated.

General Procedure 3

To the solution of (S)-tert-butyl 6-(aminomethyl)-5-azaspiro[2.4]heptane-5-carboxylate (prepared according to WO2011006960, 1 mmol) in NMP (2 ml/mmol), $K_2CO_3$ (2 mmol) and Ar1-X (where X is ortho chloro or fluoro; 1.1 mmol) were added. The reaction mixture was heated (microwave) at 100-150° C. until complete conversion of the starting material. The resulting mixture was poured in aqueous solution of NaHCO3 and extracted with AcOEt; organics were collected, washed with water, dried and evaporated. Crude was purified by silica gel chromatography (petroleum ether/ethyl acetate from 10/1 to 3/1).

General Procedure 4

To a solution of (S)-tert-butyl 6-(aminomethyl)-5-azaspiro [2.4]heptane-5-carboxylate (prepared according to WO2011006960, 1 mmol) in acetonitrile (5 ml/mmol) and N,N-diisopropylethylamine (5 mmol), Ar1-X (where X is ortho chloro or fluoro; 1.5 mmol) was added. After complete addition, the reaction mixture was heated (microwave) at 80° C. until complete conversion of the starting material. The resulting mixture was evaporated to obtain a crude mixture which was dissolved in DCM (5 ml), washed with sat. aq. NaHCO3, dried with Na2CO3 and evaporated. Residue was purified by silica gel chromatography (cyclohexane to cyclohexane/acetone=8/2).

According to general procedure 1-4 the following intermediates were prepared:

| Intermediate | Ar1 | X | Procedure | MS | Yield |
| --- | --- | --- | --- | --- | --- |
| D7 | pyridine-CF3 | F | 2 | ESI+ m/z 372 [M + H]+ | 86 |
| D8 | isoquinoline | Cl | 1 | ESI+ m/z 354 [M + H]+ | 26 |

-continued

| Intermediate | Ar1 | X | Procedure | MS | Yield |
|---|---|---|---|---|---|
| D9 | 3-F, 5-Cl pyridin-2-yl | F | 2 | ESI+ m/z 356 [M + H]+ | 45 |
| D10 | 3-F, 5-CF₃ pyridin-2-yl | F | 2 | ESI+ m/z 390 [M + H]+ | 72 |
| D11 | 3-Cl, 5-CF₃ pyridin-2-yl | F | 3 | ESI+ m/z 406 [M + H]+ | 60 |
| D12 | 5-CF₃ pyrazin-2-yl | Cl | 3 | ESI+ m/z 373 [M + H]+ | 65 |
| D13 | 6-F benzothiazol-2-yl | Cl | 1 | ESI+ m/z 378 [M + H]+ | 50 |
| D14 | 6-Cl benzothiazol-2-yl | Cl | 1 | ESI+ m/z 394 [M + H]+ | 61 |
| D15 | benzoxazol-2-yl | Cl | 4 | ESI+ m/z 344 [M + H]+ | 84 |
| D16 | 5-Cl pyridin-2-yl | — | WO2011006960 | MS (ESI) m/z: 338 [M + H]+ | 60 |
| D17 | 6-methyl pyridin-2-yl | — | WO2011006960 | MS (ESI) m/z 318 [M + H]+ | 64 |
| D18 | 4,6-dimethyl pyrimidin-2-yl | Cl | WO2011006960 | MS (ESI) m/z 333 [M + H]+ | 41 |
| D19 | 5-Cl pyrimidin-2-yl | Cl | WO2011006960 | MS (ESI) m/z 339-341 (Cl pattern) [M + H] | 61 |
| D20 | 4-CF₃ pyridin-2-yl | F | 2 | MS (ESI) m/z 372 | 93 |

| Intermediate | Ar1 | X | Procedure | MS | Yield |
|---|---|---|---|---|---|
| D21 | 4-CF3-6-methyl-pyridin-2-yl | F | 3 | MS (ESI) m/z 386 [M + H] | 33 |
| D22 | 1,5-naphthyridin-4-yl | Cl | 3 | MS (ESI) m/z 355 [M + H] | 51 |
| D23 | 4-CF3-pyrimidin-2-yl | Cl | 2 | MS (ESI) m/z 373 [M + H] | 73 |
| D24 | 4-CF3-5-Cl-pyridin-2-yl | Cl | 2 | MS (ESI) m/z 406 [M + H] | 36 |
| D25 | 5-CF3-pyrimidin-2-yl | Cl | 2 | MS (ESI) m/z 373 [M + H] | 95 |
| D26 | 4-Cl-5-CF3-pyridin-2-yl | Cl | 2 | MS (ESI) m/z 406 [M + H] | 22 |

Description 27-46 (D27-D46)

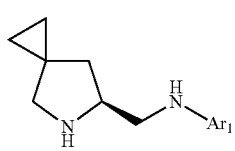

General Procedure 5

(D7-26) (1 eq.) were dissolved in dichloromethane (5 ml/mmol) and cooled to 0° C., then trifluoroacetic acid (2 ml/mmol) was added. After 1 hour at 0° C. and 3 hours at room temperature the solution was evaporated, the residue re-dissolved in dichloromethane and washed with saturated NaHCO₃ aqueous solution. The organic layers were dried (Na₂SO₄) and concentrated under vacuum.

General Procedure 6

(D7-26) (1 eq.) were dissolved in dry DCM (5 ml/mmol) under nitrogen atmosphere. TFA (2 ml/mmol) was added and the solution shaken at room temperature for 0.5-2 hours.

The reaction mixture was diluted in a small amount of MeOH and loaded on a SCX cartridge, which was then washed with MeOH, followed by a solution of ammonia 2.0 M in MeOH. The basic fractions were collected and evaporated.

According to general procedure 5 or 6 the following intermediates were prepared:

| Intermediate | Ar1 | Procedure | MS | Yield |
|---|---|---|---|---|
| D27 | 5-CF3-pyridin-2-yl | 5 | ESI+ m/z 271-273 [M + H]⁺ | 90 |

-continued
| Intermediate | Ar1 | Procedure | MS | Yield |
|---|---|---|---|---|
| D28 | 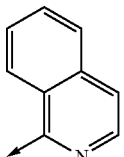 | 6 | ESI+ m/z 254 [M + H]+ | 98 |
| D29 | 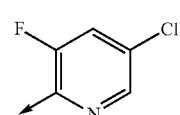 | 6 | ESI+ m/z 256-258 [M + H]+ | 96 |
| D30 | 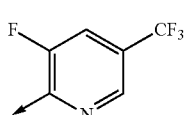 | 6 | ESI+ m/z 290-291 [M + H]+ | 82 |
| D31 | 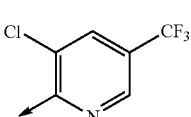 | 6 | ESI+ m/z 306 [M + H]+ | 85 |
| D32 | 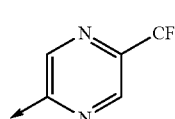 | 6 | ESI+ m/z 273 [M + H]+ | 90 |
| D33 | 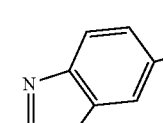 | 6 | ESI+ m/z 278 [M + H]+ | 85 |
| D34 | 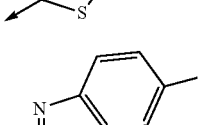 | 6 | ESI+ m/z 294 [M + H]+ | 90 |
| D35 | 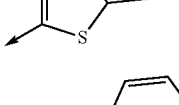 | 5 | ESI+ m/z 244 [M + H]+ | 98 |
| D36 | 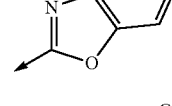 | 5 | MS (ESI) m/z: 238 [M + H]+ | 90 |
| D37 | 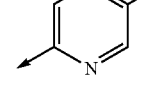 | 5 | MS (ESI) m/z 218 [M + H]+ | 54 |
| D38 | 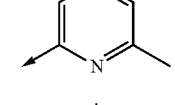 | 6 | MS (ESI) m/z 233 [M + H]+ | 71 |
| D39 | 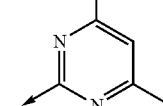 | 6 | MS (ESI) m/z 239 [M + H] | 91 |
| D40 | 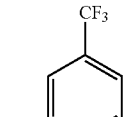 | 6 | MS (ESI) m/z 271 [M + H] | 94 |
| D41 | 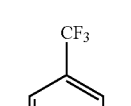 | 6 | MS (ESI) m/z 286 [M + H] | 96 |
| D42 | 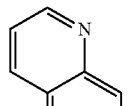 | 6 | MS (ESI) m/z 255 [M + H]+ | 99 |
| D43 | 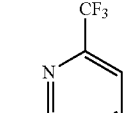 | 6 | MS (ESI) m/z 273 [M + H] | 88 |
| D44 | 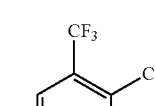 | 6 | MS (ESI) m/z 306 [M + H] | 92 |
| D45 | 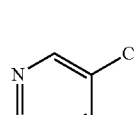 | 6 | MS (ESI) m/z 273 [M + H] | 77 |
| D46 | 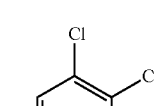 | 6 | MS (ESI) m/z 306 [M + H] | 86 |

Description 47

(S)-(3-iodo-6-methylpyridin-2-yl)(6-(((5-(trifluoromethyl)pyridin-2-yl)-amino)methyl)-5-azaspiro[2.4]heptan-5-yl)methanone (D47)

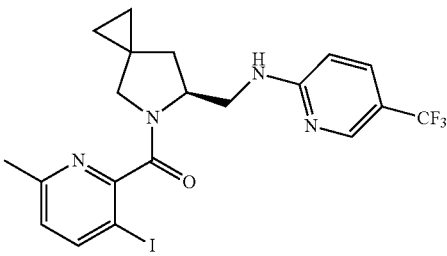 [SMILES: Cc1ccc(I)c(C(=O)N2CC3(CC3)C[C@H]2CNc2ccc(C(F)(F)F)cn2)n1]

A suspension of 3 iodo-6-methyl picolinic acid (230 mg, 1.08 mmol; prepared according to WO2010063663), N-methyl morpholine (330 μl; 3 mmol) and 2-chloro-4,6-dimethoxy-1,3,5-triazine (190 mg; 1.08 mmol) dissolved in dry 1,4-dioxane (3 ml) was stirred at 25° C. for 0.5 hours, then (D27) (290 mg; 1 mmol) dissolved in 1,4-dioxane (2 ml) was added. After 2 hours at 50° C. solvents were evaporated and residue was dissolved in EtOAc, washed with HCl 0.1N, NaOH 1N and brine. The organic layer was dried over $Na_2SO_4$ and concentrated to a crude mixture which was purified by silica gel column chromatography (DCM to AcOEt); yield 300 mg, white solid.

MS (ESI) m/z: 517-518[M+H]$^+$.

$^1$H NMR (CDCl3) δ ppm=8.28 (s, 1H), 8.06-7.90 (m, 2H), 7.70 (d, J=9.3 Hz, 1H), 6.84-7.01 (m, 2H), 4.71 (d, J=6.4 Hz, 1H), 4.06-3.82 (m, 2H), 3.39-3.28 (m, 1H), 3.12-3.03 (m, 1H), 2.57-2.50 (m, 3H), 2.38 (dd, J=8.1, 13.0 Hz, 1H), 1.78 (d, J=12.7 Hz, 1H), 0.91-0.49 (m, 4H).

Description 48

(S)-(3-bromopyridin-2-yl)(6-(((5-(trifluoromethyl)pyridin-2-yl)amino)-methyl)-5-azaspiro[2.4]heptan-5-yl)methanone (D48)

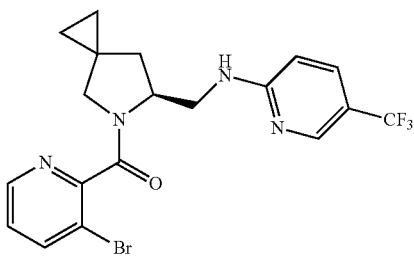 [SMILES: O=C(c1ncccc1Br)N1CC2(CC2)C[C@H]1CNc1ccc(C(F)(F)F)cn1]

A suspension of 3 bromo picolinic acid (73 mg, 0.36 mmol), N-methyl morpholine (110 μl; 1 mmol) and 2-chloro-4,6-dimethoxy-1,3,5-triazine (63 mg; 1 mmol) dissolved in dry 1,4-dioxane (2 ml) was stirred at 25° C. for 0.5 hours, then (D27) (90 mg; 1 mmol) dissolved in 1,4-dioxane (1 ml) was added. After 2 hours at 50° C. solvents were evaporated and residue was dissolved in EtOAc, washed with HCl 0.1N, NaOH 1N and brine. The organic layer was dried over $Na_2SO_4$ and concentrated to a crude mixture which was purified by silica gel column chromatography (DCM to AcOEt); yield 125 mg, white solid.

MS (ESI) m/z: 456-458[M+H]$^+$.

$^1$H NMR (CDCl3) δ ppm=8.82-8.54 (m, 1H), 8.51-8.21 (m, 1H), 8.06-7.69 (m, 2H), 7.28-7.05 (m, 2H), 4.70 (br. s., 1H), 4.11-3.79 (m, 3H), 3.37-3.09 (m, 2H), 2.36 (m, 1H), 1.82 (m, 1H), 0.89-0.48 (m, 4H).

Description 49

(S)-tert-butyl 6-((((benzyloxy)carbonyl)amino)methyl)-5-azaspiro-[2.4]heptane-5-carboxylate (D49)

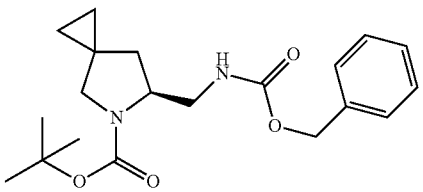 [SMILES: CC(C)(C)OC(=O)N1CC2(CC2)C[C@H]1CNC(=O)OCc1ccccc1]

To a solution of (S)-tert-butyl 6-(aminomethyl)-5-azaspiro[2.4]heptane-5-carboxylate (prepared according to WO2011006960; 136 mg, 0.6 mmol) in acetonitrile (1.5 ml), DIPEA (156 μl, 0.9 mmol) and benzylchloroformate (100 μl, 0.7 mmol) were added. After 1 h at RT the reaction was diluted with DCM (20 ml) and washed with an aqueous satd. solution of $NH_4Cl$; organics were evaporated to obtain an oil, which was purified on silica gel column (Cyclohexane/AcOEt from 9/1 to 7/3). Yield 168 mg, transparent oil.

MS (ESI) m/z: 383[M+Na]$^+$.

$^1$H NMR (CDCl3) δ ppm=7.47-7.31 (m, 5H), 5.12 (br. s., 2H), 4.22-3.99 (m, 1H), 3.46 (br. s., 2H), 3.07 (d, J=10.3 Hz, 1H), 2.31-2.11 (m, 1H), 1.64-1.37 (m, 11H), 0.75-0.48 (m, 3H).

Description 50

(S)-benzyl (5-azaspiro[2.4]heptan-6-ylmethyl)carbamate (D50)

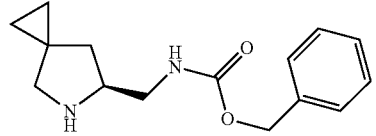 [SMILES: O=C(NC[C@@H]1CC2(CC2)CN1)OCc1ccccc1]

(D49) (168 mg, 0.47 mmol were dissolved in dry DCM (2 ml) under nitrogen atmosphere. TFA (0.5 ml) was added and the solution shaken at room temperature for 1 hour.

The reaction mixture was diluted in a small amount of MeOH and loaded on a SCX cartridge, which was then washed with MeOH, followed by a solution of ammonia 2.0 M in MeOH. The basic fractions were collected and evaporated. Yield 110 mg, transparent oil.

MS (ESI) m/z: 261-262 [M+H]$^+$.

$^1$H NMR (DMSO) δ ppm=7.45-7.27 (m, 5H), 7.25-7.12 (m, 1H), 5.01 (s, 2H), 3.25 (s, 2H), 3.03 (t, J=6.2 Hz, 2H), 2.69 (d, J=7.3 Hz, 2H), 1.72-1.61 (m, 1H), 1.47-1.36 (m, 1H), 0.56-0.37 (m, 4H).

Description 51

(S)-benzyl((5-(6-methyl-3-(pyrimidin-2-yl)picolinoyl)-5-azaspiro[2.4]-heptan-6-yl)methyl)carbamate (D51)

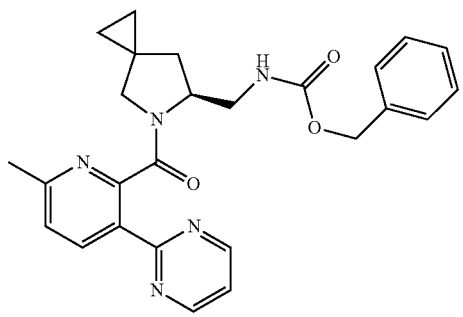 [SMILES: Cc1ccc(-c2ncccn2)c(C(=O)N2CC3(CC3)C[C@H]2CNC(=O)OCc2ccccc2)n1]

6-methyl-3-(pyrimidin-2-yl)picolinic acid (81 mg, 0.37 mmol, prepared according to WO2010063663), N-methyl morpholine (70 µl, 0.64 mmol) and 2-chloro-4,6-dimethoxy-1,3,5-triazine (61 mg, 0.35 mmol) dissolved in dry 1,4-dioxane (0.5 ml) were stirred at 40° C. for 1 hour, then (D50) (82 mg, 0.32 mmol) dissolved in 1,4-dioxane (0.5 ml) was added. After 1.5 hours at 80° C. the mixture was diluted with MeOH (10 ml) and activated carbon (Darco®, 20 mg) was added; the suspension was filtered and evaporated. The crude was purified by cartridge chromatography (Biotage KP-NH, 11 g; mobile phase cyclohexane to AcOEt) obtaining 65 mg of the title compound.

MS (ESI) m/z: 458-459[M+H]$^+$.

$^1$H NMR (DMSO) δ ppm=8.93-8.71 (m, 2H), 8.65-8.29 (m, 1H), 7.47-7.30 (m, 5H), 7.27-6.44 (m, 2H), 5.14 (d, J=4.9 Hz, 1H), 4.70-4.37 (m, 1H), 4.03-3.75 (m, 1H), 3.75-3.48 (m, 1H), 3.48-3.31 (m, 1H), 3.24-3.03 (m, 1H), 2.76-2.55 (m, 3H), 2.46-2.21 (m, 1H), 1.77-1.49 (m, 3H), 0.74 (s, 4H).

Description 52

(S)-(6-(aminomethyl)-5-azaspiro[2.4]heptan-5-yl)(6-methyl-3-(pyrimidin-2-yl)Pyridin-2-yl)methanone (D52)

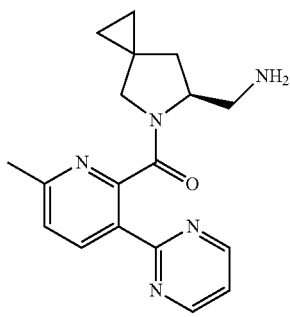 [SMILES: Cc1ccc(-c2ncccn2)c(C(=O)N2CC3(CC3)C[C@H]2CN)n1]

(D51) (65 mg, 0.14 mmol) was dissolved in EtOH (1 ml) and then ammonium formate (68 mg, 1 mmol) and Pd/C 10% (18 mg) were added. The mixture was refluxed for 1 hour then filtered over a celite pad and loaded on a SCX cartridge, which was then washed with MeOH, followed by a solution of ammonia 2.0 M in MeOH. The basic fractions were collected and evaporated. Yield 43 mg, transparent oil.

MS (ESI) m/z: 324-325 [M+H]$^+$.

$^1$H NMR (CDCl3) δ ppm=9.00-8.47 (m, 2H), 7.92-7.11 (m, 3H, under the solvent peak), 4.73-3.67 (m, 1H), 3.45-3.00 (m, 3H), 2.74-2.60 (m, 3H), 2.38 (br. s., 2H), 2.33-1.96 (m, 1H), 1.83-1.45 (m, 2H), 1.43-0.86 (m, 1H), 0.79-0.30 (m, 3H).

Description 53 methyl 2-bromo-5-chlorobenzoate (D53)

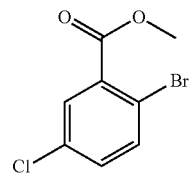

2-bromo-5-chlorobenzoic acid (4 g, 0.016 mol) was dissolved in MeOH (20 ml) and sulphuric acid (1 ml) was added. The reaction was refluxed for 3 h then cooled at RT. Water (20 ml) was added and the solid was filtered, dissolved in DCM and washed with saturated aqueous solution of NaHCO$_3$. The organic solvent was dried (Na$_2$SO$_4$) and evaporated to obtain 4.17 g of the title compound as oil.

$^1$HNMR (CDCl3) δ ppm=7.81 (d, 1H), 7.61 (d, 1H), 7.33 (dd, 1H), 3.96 (s, 3H).

Description 54 methyl 5-chloro-2-(pyrimidin-2-yl)benzoate (D54)

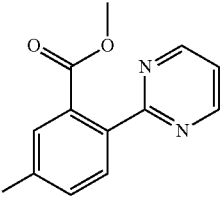

(D53) (2 g, 8 mmol) was dissolved dry DMF (15 ml), then CsF (16 mmol), CuI (1.6 mmol), [Ph$_3$P]$_4$Pd (0.8 mmol) and pyrimidine-2-tributylstannane (12 mmol; prepared according to *Eur. J. Org. Chem.* 2003, 1711-1721) were added. The mixture was warmed at 130° C. for 10 minutes (microwave), then poured in aqueous saturated solution of NH$_4$Cl and extracted with AcOEt (3×50 ml). The organic layers were combined, dried (Na$_2$SO$_4$) and concentrated under vacuum; the crude mixture was purified by silica gel column chromatography (DCM to DCM/MeOH 9/1) to give 1.5 g of the title compound as white solid.

MS (ESI) m/z: 249 [M+H]$^+$.

$^1$HNMR (CDCl3) δ ppm=8.82 (d, 2H), 8.07 (d, 1H), 7.71 (d, 1H), 7.57 (dd, 1H), 7.27 (t, 1H), 3.80 (s, 3H).

Description 55

5-chloro-2-(pyrimidin-2-yl)benzoic acid (D55)

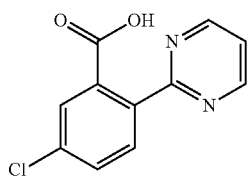 [SMILES: O=C(O)c1cc(Cl)ccc1-c1ncccn1]

(D54) (300 mg; 1.2 mmol) was dissolved in MeOH (5 ml) and aqueous NaOH (2N, 2 ml, 4 mmol) was added. The resultant solution was stirred overnight at RT then solvents were evaporated. HCl (1N, 4 ml) was added to the residue; the precipitate was collected and washed with water. 280 mg of the title compound were obtained as white solid.

MS (ESI) m/z: 235 [M+H]$^+$.

$^1$HNMR (CDCl3) δ ppm=8.91 (d, 2H), 8.26 (d, 1H), 8.17 (d, 1H), 7.63 (dd, 1H), 7.41 (t, 1H).

Description 56 methyl 6-methyl-3-phenylpicolinate (D56)

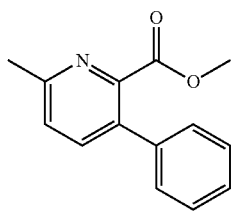

To a suspension of methyl-3-iodo-6-methylpyridine-2-carboxylate (1 g, 3.6 mmol; prepared according to WO2010063663), Phenyl Boronic Acid (440 mg, 3.6 mmol) and Pd Tetrakistriphenylphospine (417 mg; 0.36 mmol) in dry toluene (12 ml) was added K$_2$CO$_3$ 1M aq solution (3.6 ml, 3.6 mmol). The mixture was heated in a microwave oven for 5 min at 120° C. (procedure was repeated for 4 times). To promote the reaction further Tetrakistriphenylphospine palladium (208.5 mg; 0.18 mmol)) and phenyl boronic acid (220 mg, 0.18 mmol) were added. The mixture was subject to 2 cycles of microwave heating at 140° C. for 10 min. The reaction mixture was diluted with AcOEt (10 mL) and water (10 mL). The organic layer was separated, washed with brine, dried with Na$_2$SO$_4$ and filtrated. The solvent was evaporated under reduced pressure and the crude mixture purified on silica gel column (Cyclohexane to Cyclohexane/AcOEt 9:1) to obtain 506 mg of the title compound as yellow oil.

MS (ESI) m/z: 228 [M+H]$^+$.

$^1$HNMR (CDCl3) δ ppm=7.67 (d, J=7.8 Hz, 1H), 7.47-7.33 (m, 6H), 3.77 (s, 3H), 2.68 (s, 3H).

Description 57

6-methyl-3-phenylpicolinic acid (D57)

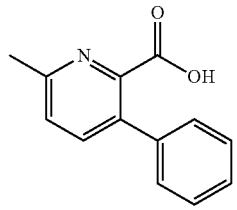 [SMILES: Cc1ccc(-c2ccccc2)c(C(=O)O)n1]

(D56) (0.124 g, 0.545 mmol, 1 eq.) was suspended in 25 ml of a water/dioxane 1/3 mixture. LiOH (34 mg, 0.818 mmol, 1.5 eq.) was added and the resulting mixture was heated to 70° C. for 1 hour. The dioxane was then removed by distillation; the resulting solution was further diluted with water and washed with AcOEt. The basic aqueous phase was then acidified with aqueous HCl (4M) down to pH 1. The resulting suspension was extracted with AcOEt.

The organic phase was then dried over sodium sulphate, filtered and evaporated to dryness to give 120 mg of (D57) as a yellowish solid.

$^1$H NMR (DMSO) δ ppm=13.18 (br. s., 1H), 7.78 (d, J=7.8 Hz, 1H), 7.49-7.37 (m, 6H), 2.54 (s, 3H).

Description 58 methyl 2-iodo-3-methylbenzoate (D58)

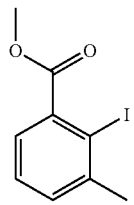

2-iodo-3-methylbenzoic acid (595 mg, 2.27 mmol) was dissolved in DCM/MeOH=1/1 (5 ml) at 0° C., then TMS-CH$_2$N$_2$ (2M in Et2O, 1.4 ml, 2.8 mmol) was added. After 1.5 hours at RT solvents were evaporated. Yield 630 mg yellow oil.

$^1$HNMR (CDCl3) δ ppm==7.42-7.32 (m, 2H), 7.32-7.25 (m, 1H, under the solvent peak), 2.55 (s, 3H).

Description 59 methyl 3-methyl-2-(pyrimidin-2-yl)benzoate (D59)

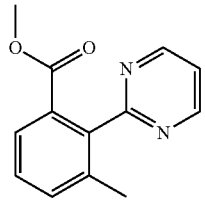 [SMILES: COC(=O)c1cccc(C)c1-c1ncccn1]

(D58) (353 mg, 1.3 mmol) was dissolved dry DMF (3 ml), then CsF (410 mg, 2.7 mmol), CuI (27 mg, 0.14 mmol), [Ph$_3$P]$_4$Pd (153 mg, 0.13 mmol) and pyrimidine-2-tributylstannane (528 mg, 1.43 mmol; prepared according to *Eur. J. Org. Chem.* 2003, 1711-1721) were added. The mixture was warmed at 130° C. for 15 minutes (microwave), then poured in aqueous saturated solution of NH$_4$Cl and extracted with AcOEt (3×50 ml). The organic layers were combined, dried (Na$_2$SO$_4$) and concentrated under vacuum; the crude mixture was purified by silica gel column chromatography (cyclohexane to cyclohexane/AcOEt=1/1) to give 150 mg of the title compound as yellow oil.

MS (ESI) m/z: 229[M+H]$^+$.

$^1$H NMR (CDCl3) δ ppm=8.87 (d, J=4.9 Hz, 1H), 7.91 (d, J=7.3 Hz, 1H), 7.56-7.46 (m, 1H), 7.43 (d, J=7.8 Hz, 1H), 7.34-7.21 (m, 2H, under the solvent peak), 2.18 (s, 3H).

Description 60

3-methyl-2-(pyrimidin-2-yl)benzoic acid (D60)

To a solution of (D59) (179 mg; 0.7 mmol) in MeOH-water (1/1; 5 ml) LiOH.H$_2$O (76 mg; 3.16 mmol) was added and the solution heated at 80° C. for 1 hour.

Solvents were evaporated under reduced pressure, residue taken up with 5 ml of brine and the resultant solution acidified to pH 2 with HCl 1N and extracted with AcOEt (4×10 ml). The organic layers were collected, dried with Na$_2$SO$_4$ and evaporated to obtain 138 mg of the title compound as white solid.

MS (ESI) m/z: 215 [M+H]$^+$.

$^1$H NMR (DMSO) δ ppm=8.86 (d, J=4.4 Hz, 1H), 7.74 (d, J=7.3 Hz, 1H), 7.59-7.37 (m, 3H), 2.07 (s, 3H).

Description 61

2-chloro-5-(methylsulfonyl)benzoic acid (D61)

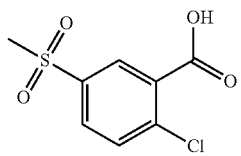

To a solution of 2-chloro-5-(methylthio)benzoic acid (6.05 g, 30 mmol) and NaHCO3 (20 g, 240 mmol) in NaOH 0.5N (75 ml) a solution of oxone (24 g) in EDTA (0.0004M, 90 ml) was added. After 1 hour at RT Na$_2$S$_2$O$_3$ (15 g in 100 ml of water) was added; after 10 min HCl 4N was added to pH 2. The white solid was filtered, washed with water and dried in vacuum at 70° C. Yield 6 g white solid.

MS (ESI) m/z: 235 [M+H]$^+$.

$^1$H NMR (Acetone) δ ppm=8.43 (d, J=2.4 Hz, 1H), 8.11 (dd, J=2.4, 8.3 Hz, 1H), 7.86 (d, J=8.3 Hz, 1H), 3.25 (s, 3H)

Description 62 methyl 2-chloro-5-(methylsulfonyl)benzoate (D62)

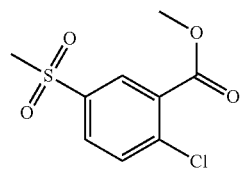

2-chloro-5-(methylsulfonyl)benzoic acid (4 g, 0.016 mol) was dissolved in MeOH (10 ml) and thionyl chloride (1 ml) was added. The reaction was stirred for 72 h at RT. Solvents were evaporated and crude solid was dissolved in DCM and washed with saturated aqueous solution of NaHCO$_3$. The organic solvent was dried (Na$_2$SO$_4$) and evaporated to obtain 0.88 g of the title compound as white solid.

MS (ESI) m/z: 249 [M+H]$^+$.

$^1$H NMR (Acetone) δ ppm=8.37 (d, J=2.4 Hz, 1H), 8.12 (dd, J=2.4, 8.3 Hz, 1H), 7.86 (d, J=8.3 Hz, 1H), 3.98 (s, 3H), 3.24 (s, 3H)

Description 63 methyl 4-(methylsulfonyl)-[1,1]-biphenyls-2-carboxylate (D63)

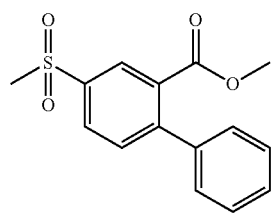

To a suspension of (D62) (450 mg, 1.8 mmol), phenyl boronic acid (330 mg, 2.7 mmol) and Pd tetrakistriphenylphospine (104 mg; 0.09 mmol) in dry Toluene (6 ml) was added K$_2$CO$_3$ (345 mg, 2.7 mmol). The mixture was heated in microwave oven for 30 min at 140° C. The reaction mixture was diluted with AcOEt (10 mL) and water (10 mL). The organic layer was separated, washed with brine, dried over Na$_2$SO$_4$ and filtrated. The solvent was evaporated under reduced pressure; the crude mixture was purified on silica gel (Cyclohexane to Cyclohexane/AcOEt 1:1) to obtain 330 mg of the title compound as white solid.

MS (ESI) m/z: 291 [M+H]$^+$.

$^1$H NMR (CDCl3) δ ppm=8.42 (d, J=2.0 Hz, 1H), 8.11 (dd, J=2.0, 7.8 Hz, 1H), 7.62 (d, J=7.8 Hz, 1H), 7.50-7.42 (m, 3H), 7.38-7.30 (m, 2H), 3.72 (s, 3H), 3.15 (s, 3H).

Description 64

4-(methylsulfonyl)-[1,1'-biphenyl]-2-carboxylic acid (D64)

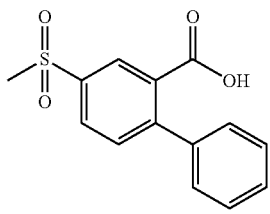 [SMILES: CS(=O)(=O)c1ccc(-c2ccccc2)c(C(=O)O)c1]

To a solution of methyl 4-(methylsulfonyl)-[1,1'-biphenyl]-2-carboxylate (330 mg, 1.1 mmol) in methanol (15 ml) NaOH 2N (1.1 ml; 2.3 mmol) was added and the solution left stirring at room temperature for 72 hours.

Solvents were evaporated under reduced pressure and residue taken up with 5 ml of brine; the resultant solution was acidified to pH 2 with HCl 1N and the solid filtered and dried to obtain 160 mg of the title compound as white solid.

MS (ESI) m/z: 277 [M+H]$^+$.

$^1$H NMR (Acetone) δ ppm=8.39 (d, J=2.0 Hz, 1H), 8.16 (dd, J=2.0, 8.3 Hz, 1H), 7.71 (d, J=8.3 Hz, 1H), 7.50-7.40 (m, 5H), 3.27 (s, 3H).

Description 65

(3-(benzyloxy)-6-methylpyridin-2-yl)methanol (D65)

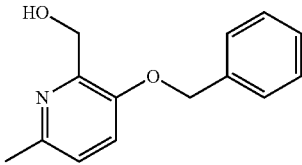 [SMILES: Cc1ccc(OCc2ccccc2)c(CO)n1]

2-(hydroxymethyl)-6-methylpyridin-3-ol (100 mg; 0.719 mmol); K$_2$CO$_3$ (497 mg; 3.59 mmol) and (bromomethyl)benzene (246 mg; 1.44 mmol) were stirred in DMF (1 ml) at RT for 18 h; solvent was evaporated, residue was dissolved in HCl 0.1N (20 ml) and washed with ethyl acetate (3×10 ml); aqueous phase was treated with Na$_2$CO$_3$ to pH 9 and extracted with acetate (3×10 ml). Organics were washed with brine, dried and evaporated to give 110 mg of the title compound (yellow solid).

MS (ESI) m/z: 230 [M+H]$^+$.

$^1$HNMR (CDCl$_3$) δ ppm=7.34-7.41 (m, 5H), 7.12 (d, J=8 Hz, 1H), 7.02 (d, J=8 Hz, 1H), 5.12 (s, 2H), 4.80 (s, 2H), 4.51 (br. s. 1H), 2.53 (s, 3H).

Description 66

3-(benzyloxy)-6-methylpicolinic acid (D66)

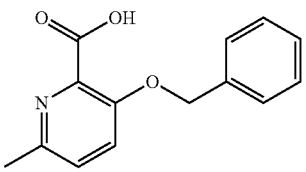 [SMILES: Cc1ccc(OCc2ccccc2)c(C(=O)O)n1]

To a solution of (D65) (110 mg; 0.48 mmol) in acetonitrile (3 ml) TEMPO (11.3 mg; 0.072 mmol) and NaH$_2$PO$_4$ (0.64M in water; 2.06 ml) were added. The solution was warmed at 35° C. then NaOCl$_2$ (235 mg in 1 ml of water; 2.6 mmol) and NaOCl (128 μl in 1 ml of water) were added simultaneously. After 2 h NaOH 2N was added to pH 8, then the mixture was poured in ice and an aqueous solution of Na$_2$S$_2$O$_3$, stirred for 30 min, then HCl was added to pH3 and extracted with DCM (3×20 ml); organics were washed with water, dried and evaporated. Yield 105 mg, light yellow solid.

MS (ESI) m/z: 244 [M+H]$^+$.

$^1$HNMR (CDCl$_3$) δ ppm=7.51-7.53 (m, 2H), 7.39-7.42 (m, 3H), 7.33-7.36 (m, 2H), 5.32 (s, 2H), 2.56 (s, 3H).

Description 67

(3-((2,3-difluorobenzyl)oxy)-6-methylpyridin-2-yl)methanol (D67)

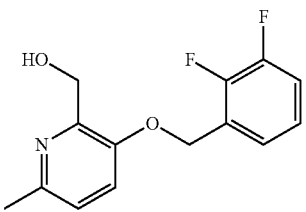 [SMILES: Cc1ccc(OCc2cccc(F)c2F)c(CO)n1]

2-(hydroxymethyl)-6-methylpyridin-3-ol (100 mg; 0.719 mmol); K$_2$CO$_3$ (497 mg; 3.59 mmol) and (bromomethyl)-2,3-benzene (296 mg; 1.44 mmol) were stirred in DMF (1 ml) at RT for 18 h; the solvent was evaporated, the residue was dissolved in HCl 0.1N (20 ml) and washed with ethyl acetate (3×10 ml); the aqueous phase was treated with Na$_2$CO$_3$ to pH 9 and extracted with acetate (3×10 ml). Organics were washed with brine, dried and evaporated to give 144 mg of the title compound (yellow solid).

MS (ESI) m/z: 266 [M+H]$^+$.

$^1$HNMR (CDCl$_3$) δ ppm=7.11-7.24 (m, 4H), 7.05 (d, J=12 Hz, 1H), 5.19 (s, 2H), 4.78 (s, 2H), 4.49 (br. s. 1H), 2.54 (s, 3H).

Description 68

3-((2,3-difluorobenzyl)oxy)-6-methylpicolinic acid (D68)

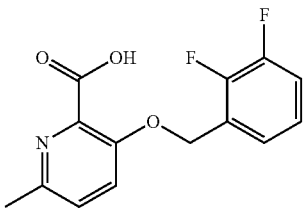 [SMILES: Cc1ccc(OCc2cccc(F)c2F)c(C(=O)O)n1]

To a solution of (D67) (144 mg; 0.54 mmol) in acetonitrile (3.5 ml) TEMPO (12.66 mg; 0.081 mmol) and NaH$_2$PO$_4$ (0.64M in water; 2.32 ml) were added. The solution was warmed at 35° C. then NaOCl$_2$ (263 mg in 1 ml of water; 2.6 mmol) and NaCl (144 μl in 1 ml of water) were added simultaneously. After 30' NaOH 2N was added to pH 8, then the mixture was poured in ice and an aqueous solution of Na$_2$S$_2$O$_3$, stirred for 30 min, then HCl was added to pH3 and extracted with DCM (3×20 ml); organics were washed with water, dried and evaporated. Yield 105 mg, light yellow solid.

MS (ESI) m/z: 280 [M+H]$^+$.

$^1$HNMR (CDCl$_3$) δ ppm=7.59-7.63 (m, 1H), 7.40-7.48 (m, 2H), 7.14-7.19 (m, 2H), 5.36 (s, 2H), 2.57 (s, 3H).

Description 69

(3-((4-fluorobenzyl)oxy)-6-methylpyridin-2-yl) methanol (D69)

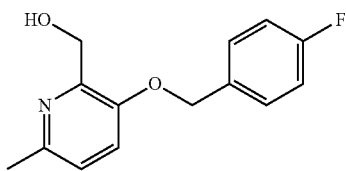 [SMILES: Cc1ccc(OCc2ccc(F)cc2)c(CO)n1]

2-(hydroxymethyl)-6-methylpyridin-3-ol (100 mg; 0.719 mmol); K$_2$CO$_3$ (497 mg; 3.59 mmol) and (bromomethyl)-4 fluorobenzene (270 mg; 1.44 mmol) were stirred in DMF (1 ml) at RT for 18 h; the solvent was evaporated, the residue was dissolved in HCl 0.1N (20 ml) and washed with ethyl acetate (3×10 ml); the aqueous phase was treated with Na$_2$CO$_3$ to pH 9 and extracted with acetate (3×10 ml). Organics were washed with brine, dried and evaporated to give 119 mg of the title compound (yellow solid).

MS (ESI) m/z: 248 [M+H]$^+$.

$^1$HNMR (CDCl$_3$) δ ppm=7.36-7.40 (m, 2H), 7.02-7.12 (m, 4H), 5.07 (s, 2H), 4.78 (s, 2H), 4.50 (br. s. 1H), 2.53 (s, 3H).

Description 70

3-((4-fluorobenzyl)oxy)-6-methylpicolinic acid (D70)

To a solution of (D69) (119 mg; 0.48 mmol) in acetonitrile (3 ml) TEMPO (10.94 mg; 0.07 mmol) and NaH$_2$PO$_4$ (0.64M in water; 2.06 ml) were added. The solution was warmed at 35° C. then NaOCl$_2$ (234 mg in 1 ml of water; 2.6 mmol) and NaCl (127 μl in 1 ml of water) are added simultaneously. After 30' NaOH 2N was added to pH 8, then the mixture was poured in ice and an aqueous solution of Na$_2$S$_2$O$_3$, stirred for 30 min, then HCl was added to pH3 and extracted with DCM (3×20 ml); organics were washed with water, dried and evaporated. Yield 123 mg, light yellow solid.

MS (ESI) m/z: 262 [M+H]$^+$.

$^1$HNMR (CDCl$_3$) δ ppm=7.51-7.54 (m, 2H), 7.35-7.41 (m, 2H), 7.08-7.12 (m, 2H), 5.26 (s, 2H), 2.56 (s, 3H).

Description 71

(3-((2,4-difluorobenzyl)oxy)-6-methylpyridin-2-yl) methanol (D71)

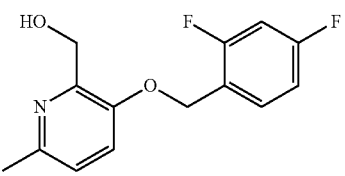 [SMILES: Cc1ccc(OCc2ccc(F)cc2F)c(CO)n1]

2-(hydroxymethyl)-6-methylpyridin-3-ol (100 mg; 0.719 mmol); K$_2$CO$_3$ (497 mg; 3.59 mmol) and (bromomethyl)-2,4 difluorobenzene (296 mg; 1.44 mmol) were stirred in DMF (1 ml) at RT for 18 h; the solvent was evaporated, the residue was dissolved in HCl 0.1N (20 ml) and washed with ethyl acetate (3×10 ml); the aqueous phase was treated with Na$_2$CO$_3$ to pH 9 and extracted with acetate (3×10 ml). Organics were washed with brine, dried and evaporated to give 133 mg of the title compound (yellow solid).

MS (ESI) m/z: 266 [M+H]$^+$.

$^1$HNMR (CDCl$_3$) δ ppm=7.40-7.46 (m, 1H), 7.15-7.17 (m, 1H), 7.03-7.06 (m, 1H), 6.85-6.95 (m, 2H), 5.11 (s, 2H), 4.76 (s, 2H), 4.46 (br. s. 1H), 2.53 (s, 3H).

Description 72

3-((2,4-difluorobenzyl)oxy)-6-methylpicolinic acid (D72)

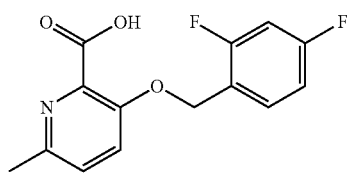 [SMILES: Cc1ccc(OCc2ccc(F)cc2F)c(C(=O)O)n1]

To a solution of (D71) (133 mg; 0.5 mmol) in acetonitrile (3 ml) TEMPO (12.6 mg; 0.08 mmol) and NaH$_2$PO$_4$ (0.64M in water; 2.28 ml) were added. The solution was warmed at 35° C. then NaOCl$_2$ (244 mg in 1 ml of water; 2.7 mmol) and NaOCl (133 μl in 1 ml of water) were added simultaneously. After 30' NaOH 2N was added to pH 8, then the mixture was poured in ice and an aqueous solution of Na$_2$S$_2$O$_3$, stirred for 30 min, then HCl was added to pH3 and extracted with DCM (3×20 ml); organics were washed with water, dried and evaporated. Yield 143 mg, light yellow solid.

MS (ESI) m/z: 280 [M+H]$^+$.

$^1$HNMR (CDCl$_3$) δ ppm=7.79-7.85 (m, 1H), 7.40-7.47 (m, 2H), 6.95-7.0 (m, 1H), 6.83-6.88 (m, 1H), 5.29 (s, 2H), 2.57 (s, 3H).

Description 73

(3-((3,5-difluorobenzyl)oxy)-6-methylpyridin-2-yl)methanol (D73)

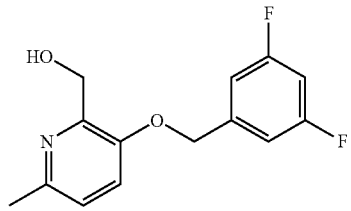 [SMILES: Cc1ccc(OCc2cc(F)cc(F)c2)c(CO)n1]

2-(hydroxymethyl)-6-methylpyridin-3-ol (100 mg; 0.719 mmol); K$_2$CO$_3$ (497 mg; 3.59 mmol) and (bromomethyl)-3,5-difluorobenzene (296 mg; 1.44 mmol) were stirred in DMF (1 ml) at RT for 18 h; solvent was evaporated, residue was dissolved in HCl 0.1N (20 ml) and washed with ethyl acetate (3×10 ml); aqueous phase was treated with Na$_2$CO$_3$ to pH 9 and extracted with acetate (3×10 ml). Organics were washed with brine, dried and evaporated to give 180 mg of the title compound (white solid).

MS (ESI) m/z: 266 [M+H]$^+$.

$^1$HNMR (CD$_3$OD) δ ppm=7.36 (d, J=8 Hz, 1H), 7.16 (d, J=8 Hz, 1H), 7.10-7.13 (m, 2H), 6.89-6.93 (m, H), 5.19 (s, 2H), 4.76 (s, 2H), 2.49 (s, 3H).

Description 74

3-((3,5-difluorobenzyl)oxy)-6-methylpicolinic acid (D74)

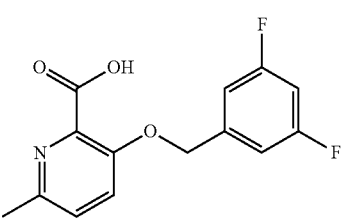 [SMILES: Cc1ccc(OCc2cc(F)cc(F)c2)c(C(=O)O)n1]

To a solution of (D73) (180 mg; 0.68 mmol) in acetonitrile (4.3 ml) TEMPO (15.9 mg; 0.1 mmol) and NaH$_2$PO$_4$ (0.64M in water; 2.28 ml) were added. The solution was warmed at 35° C. then NaOCl$_2$ (332 mg in 1 ml of water; 2.7 mmol) and NaOCl (181 μl in 1 ml of water) were added simultaneously. After 30' NaOH 2N was added to pH 8, then the mixture was poured in ice and an aqueous solution of Na$_2$S$_2$O$_3$, stirred for 30 min, then HCl was added to pH3 and extracted with DCM (3×20 ml); organics were washed with water, dried and evaporated. Yield 180 mg, light yellow solid.

MS (ESI) m/z: 280 [M+H]$^+$.

$^1$HNMR (CD$_3$OD) δ ppm=7.63 (d, J=8 Hz, 1H), 7.44 (d, J=8 Hz, 1H), 7.16-7.18 (m, 2H), 6.88-6.93 (m, H), 5.26 (s, 2H), 2.53 (s, 3H).

Description 75 methyl 5-bromo-2-(pyrimidin-2-yl)benzoate (D75)

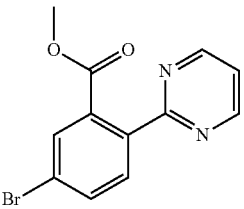 [SMILES: COC(=O)c1cc(Br)ccc1-c1ncccn1]

Methyl-5-bromo-2-iodobenzoate (2.52 g, 7.4 mmol) was dissolved dry DMF (10 ml), then CsF (2.25 g, 14.8 mmol), CuI (285 mg, 1.5 mmol), [Ph$_3$P]$_4$Pd (855 mg, 0.74 mmol) and pyrimidine-2-tributylstannane (2.73 g, 7.4 mmol; prepared according to *Eur. J. Org. Chem.* 2003, 1711-1721) were added. The mixture was warmed at 130° C. for 15 minutes (microwave), then poured in aqueous saturated solution of NH$_4$Cl and extracted with AcOEt (3×50 ml). The organic layers were combined, dried (Na$_2$SO$_4$) and concentrated under vacuum; the crude mixture was purified by silica gel column chromatography (cyclohexane to cyclohexane/AcOEt=1/1) to give 200 mg of the title compound as yellow oil.

MS (ESI) m/z: 294 [M+H]$^+$.

Description 76

5-bromo-2-(pyrimidin-2-yl)benzoic acid (D76)

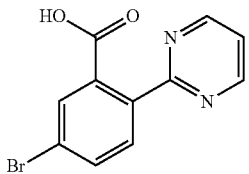 [SMILES: O=C(O)c1cc(Br)ccc1-c1ncccn1]

To a solution of (D75) (200 mg; 0.68 mmol) in MeOH-water (2/1; 12 ml) LiOH.H$_2$O (72 mg; 1.7 mmol) was added and the solution left at room temperature for 18 hours.

Solvents were evaporated under reduced pressure, residue taken up with 5 ml of brine and the resultant solution acidified to pH 2 with HCl 1N and extracted with AcOEt (4×10 ml). The organic layers were collected, dried with Na$_2$SO$_4$ and evaporated to obtain 120 mg of the title compound as white solid.

MS (ESI) m/z: 279-281 [M+H]$^+$.

Description 77 methyl 2-fluoro-6-iodobenzoate (D77)

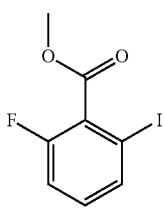

Oxalyl chloride (2.5 ml, 28.66 mmol, 1.5 eq.) was added at room temperature to a suspension of 2-fluoro-6-iodobenzoic acid (5.1 g, 19.17 mmol, 1 eq.) in 40 ml of dry DCM under nitrogen atmosphere. A few drops of dry DMF were added and the mixture was stirred at room temperature for 1 h. The solvent was removed by distillation. The obtained residue was taken up in acetonitrile, which was distilled again, to remove excess acidity. The resulting brown oil was dissolved in dry DCM and the resulting solution was dropwise added to a suspension of potassium carbonate (7 g, 50.6 mmol, 2.6 eq.) in 20 ml of dry methanol. The reaction mixture was then stirred at room temperature overnight.

The next morning the solids were filtered away and washed with DCM. The volume of the liquid phase was reduced by vacuum distillation. The resulting slurry was taken up in DCM and filtered again.

The clear liquid phase was then dried over sodium sulphate, filtered and evaporated do dryness to give 4.27 g (15.25 mmol) of (D77) as a yellow oil.

MS (ESI) m/z: 219 [M+H]$^+$.

$^1$H NMR (CDCl$_3$) δ ppm=7.78-7.60 (m, 1H), 7.28 (s, 1H), 7.14 (dd, J=3.7, 8.1 Hz, 2H), 4.00 (s, 3H).

Description 78 methyl-2-fluoro-6-(pyrimidin-2-yl)benzoate (D78)

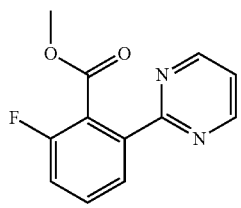 [SMILES: COC(=O)c1c(F)cccc1-c1ncccn1]

Methyl 2-fluoro-6-iodobenzoate (17 g, 61 mmol, 1 eq.) and 2-(tributylstannyl)pyrimidine (26.7 g, 72 mmol, 1.2 eq.) were dissolved in 120 ml of dry DMF under nitrogen atmosphere. Cesium fluoride (18.1 g, 119 mmol, 2 eq., highly hygroscopic) was added and nitrogen was bubbled into the suspension for 5 minutes. While bubbling, Copper iodide (1.1 g, 5.77 mmol 0.1 eq.) and tetrakis(triphenylphosphine)palladium(0) (6.9 g, 5.97 mmol, 0.1 eq) were added. The mixture was then heated at 115° C. for 45 minutes. After that, it was allowed to cool to room temperature, diluted with a large volume of AcOEt and filtered over celite. The resulting liquid phase was washed thoroughly with a saturated aqueous solution of ammonium chloride to remove DMF, dried with sodium sulphate, filtered and evaporated to dryness.

The isolated crude oil was then purified by flash chromatography on silica gel, eluting with a linear gradient from cyclohexane to Cy:AcOEt 6/4. Evaporation of the collected fractions yielded 9.7 g of (D78) as a yellow-orange oil.

MS (ESI) m/z: 233 [M+H]$^+$.

Description 79

2-fluoro-6-(pyrimidin-2-yl)benzoic acid (D79)

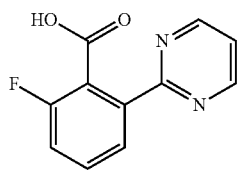 [SMILES: O=C(O)c1c(F)cccc1-c1ncccn1]

(D78) (1.48 g, 6.4 mmol, 1 eq.) was suspended in 25 ml of a water/MeOH 1/1 mixture. LiOH (1.48 g, 35.27 mmol, 5 eq.) was added and the resulting mixture was heated to 80° C. for 3 hours. The methanol was then removed by distillation; the resulting solution was further diluted with water and washed with AcOEt. The basic aqueous phase was then acidified with aqueous HCl (4M) down to pH 1. The resulting suspension was extracted with AcOEt.

The organic phase was then dried over sodium sulphate, filtered and evaporated to dryness to give 1.28 g (5.87 mmol) of (D79) as a yellowish solid.

$^1$H NMR (DMSO) δ ppm=13.23 (br. s., 1H), 8.91 (d, J=4.4 Hz, 2H), 8.01 (d, J=7.8 Hz, 1H), 7.73-7.57 (m, 1H), 7.54-7.29 (m, 2H).

Description 80 methyl 3-fluoro-6-iodobenzoate (D80)

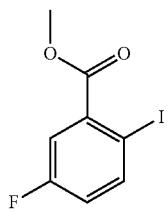

To a solution of 3-fluoro-6-iodo benzoic acid (50 g; 0.18 mol) in methanol (220 ml) were added 10 ml of sulfuric acid and the mixture heated at reflux for 24 hours. After that the solvent was evaporated and the crude mixture diluted with water and extracted with dichloromethane (3×70 ml), the organic phases were collected, washed with bicarbonate (3×100 ml), dried over sodium sulphate and concentrated to yield the desired compound (51 g).

Description 81 methyl 5-fluoro-2-(4,4,5,5,-tetramethyl-1,2,3-dioxaborolan-2-yl)benzoate (D81)

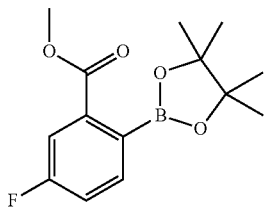 [SMILES: COC(=O)c1cc(F)ccc1B1OC(C)(C)C(C)(C)O1]

To a solution of (D80) in THF (200 ml) and triethylamine (54.3 ml; 390 mmol) at room temperature, 4,4,5,5-Tetramethyl-1,3,2-dioxaborolane (25 g; 195 mmol) was added dropwise prior addition to palladium (II) acetate (730 mg; 3.25 mmol) and tri(o-tolyl)phosphine (2 g; 6.5 mmol). The reaction was heated at 70° C. for 2 hours and subsequently poured into a mixture of H$_2$O/AcOEt (2 L). The organic phases was separated, washed with a water (3×500 ml) and a saturated solution of NaCl (1×300 ml). The organic phase was dried over sodium sulphate and evaporated. (D81) was used in the next step as such without further purifications.

Description 82 methyl 5-fluoro-2-(pyrimidin-2-yl)benzoate (D82)

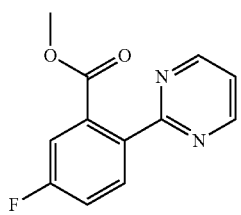 [SMILES: COC(=O)c1cc(F)ccc1-c1ncccn1]

A flow of nitrogen was bubbled into a solution of sodium carbonate (41.34 g; 390 mmol) in water (90 ml) for 15 minutes prior addition to a solution of 2-chloropyrimidine (17.94 g; 156 mmol) and (D81) in tetrahydrofurane (240 ml); After stirring the reaction for 10 minutes at room temperature, [1,1']Bis(diphenylphosphino)ferrocene]dichloropalladium (II) was added. The reaction was heated at 70° C. for 3 hours, cooled to room temperature and then poured into water (600 ml) before extracting with ethyl acetate (3×500 ml); the organic phases were collected, dried over sodium sulphate and filtered. To the filtrate SiO$_2$ (10 g) was added and the ethyl acetate filtered once again, the pad of silica was washed once with ethyl acetate (100 ml). The filtrates were collected and evaporated to yield to brown oil, which was used in the next step as such without further purification.

MS (ESI) m/z: 233 [M+H]$^+$.

Description 83

5-fluoro-2-(pyrimidin-2-yl)benzoic acid (D83)

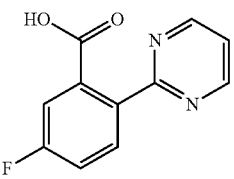 [SMILES: O=C(O)c1cc(F)ccc1-c1ncccn1]

(D82) (36 g, 130 mmol) was suspended in 195 ml of NaOH 2N and 500 ml of MeOH and the resulting mixture left at room temperature for 3 hours. The methanol was removed by distillation; the resulting solution was further diluted with water and washed with AcOEt. The basic aqueous phase was then acidified with aqueous HCl (4M) down to pH 1. The resulting suspension was extracted with AcOEt.

The organic phase was then dried over sodium sulphate, filtered and evaporated to dryness to give 13.7 g of (D83) as white solid.

MS (ESI) m/z: 219 [M+H]$^+$.

$^1$H NMR (DMSO-d$_6$) δ ppm=13.00 (br. s., 1H), 8.88 (d, J=4.9 Hz, 2H), 8.22-7.80 (m, 1H), 7.65-7.13 (m, 3H).

Description 84

5-methyl-2-(pyrimidin-2-yl)benzoic acid (D84)

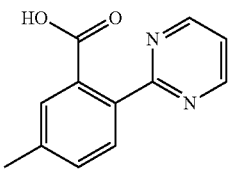 [SMILES: Cc1ccc(-c2ncccn2)c(C(=O)O)c1]

The 5-methyl-2-(pyrimidin-2-yl)benzoic acid was prepared according to the procedure described in WO 2008147518.

Description 85

2 methyl-5-phenylthiazole-4-carboxylic acid (D85)

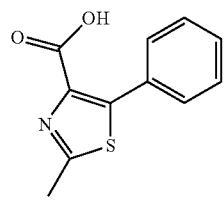

The 2 methyl-5-phenylthiazole-4-carboxylic acid was prepared according to the procedure described in U.S. Pat. No. 3,282,927.

Description 86

Pyridine-2,3-dicarboxylic acid dimethyl ester (D86)

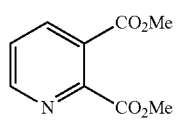

To a solution of pyridine-2,3-dicarboxylic acid (50.0 g, 0.299 mol) in methanol (500 ml) was added con. sulfuric acid (20 ml). After heated to reflux for 24 hours, the mixture was basified with saturate sodium carbonate solution until pH=8 and then extracted with ethyl acetate. The combined extracts were washed with brine, dried over magnesium sulphate, filtered and evaporated to give D78 (45.7 g) as a white solid.

$^1$H NMR (CDCl$_3$) δ ppm=3.95 (s, 3H), 4.01 (s, 3H), 7.51 (m, 1H), 8.18 (dd, J=6.4, 1.6 Hz, 1H), 8.77 (dd, J=6.8, 2.0 Hz, 1H).

Description 87

Pyridine-2,3-dicarboxylic acid dimethyl ester N-oxide (D87)

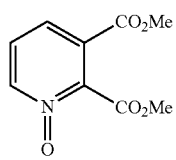

To a solution of pyridine-2,3-dicarboxylic acid dimethyl ester (D78, 45.7 g, 0.234 mol) in trichloromethane (700 mL) was added 3-chloroperbenzoic acid (137.1 g, 0.797 mol). After stirred at reflux overnight, the reaction mixture was washed with aqueous sodium bicarbonate and brine, dried over magnesium sulphate, filtered and evaporated. The resulting solid was purified by column chromatography on silica gel (2% methanol in dichloromethane) to give the first part of D79 as a white solid (17.9 g). Another crude product was purified by recrystallization from methanol to give the second part of D79 as a white solid (6.95 g). The filtrate was concentrated in vacuum to afford a residue which was purified by column chromatography on silica gel (25% ethyl acetate in petroleum ether to 2% methanol in dichloromethane) to give the last part of D79 as a white solid (3.3 g). Total: 28.15 g $^1$HNMR (DMSO-d$_6$) δ ppm=3.88 (s, 3H), 3.89 (s, 3H), 7.66 (m, 1H), 7.90 (d, J=8.4 Hz, 1H), 8.57 (d, J=6.4 Hz, 1H).

Description 88

6-Chloro-pyridine-2,3-dicarboxylic acid dimethyl ester (D88)

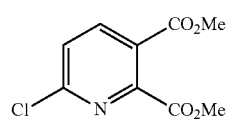

A mixture of pyridine-2,3-dicarboxylic acid dimethyl ester N-oxide (D79, 17.9 g, 84.83 mmol) in phosphoric trichloride (70 ml) was heated to reflux for 2 hours. The reaction solution was poured into ice water and extracted with ethyl acetate. The combined extracts were washed with brine, dried over magnesium sulphate, filtered and evaporated. The residue was purified by column chromatography on silica gel (20% ethyl acetate in petroleum ether) to give D80 (10.31 g) as a brown oil.

$^1$H NMR (CDCl$_3$) δ ppm=3.92 (s, 3H), 3.97 (s, 3H), 7.49 (d, J=8.0 Hz, 1H), 8.151 (d, J=8.0 Hz, 1H)

Description 89

6-Cyclopropyl-pyridine-2,3-dicarboxylic acid dimethyl ester (D89)

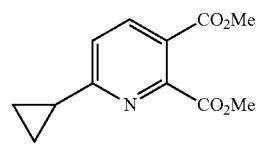 [SMILES: COC(=O)c1ccc(C2CC2)nc1C(=O)OC]

To a solution of 6-chloro-pyridine-2,3-dicarboxylic acid dimethyl ester (D80, 16.8 g, 73.4 mmol) in toluene (340 ml) and water (34 ml) was added cyclopropylboronic acid (7.56 g, 88.1 mmol), K$_3$PO$_4$·H$_2$O (58.6 g, 220.2 mmol) and tricyclohexylphosphine (2.06 g, 7.34 mmol) under N$_2$ atmosphere, followed by addition of palladium diacetate (0.84 g, 3.67 mmol). After stirred at reflux for 4 hours, the mixture was filtered and partitioned between ethyl acetate and water. The combined extracts were washed with brine, dried over magnesium sulphate, filtered and evaporated. The resulting solid was purified by column chromatography on silica gel (12.5% ethyl acetate in petroleum ether) to give D81 (12.6 g) as a yellow solid.

$^1$H NMR (DMSO-d$_6$) δ ppm=0.95~0.99 (m, 2H), 1.05~1.10 (m, 2H), 2.22~2.26 (m, 1H), 3.83 (s, 3H), 3.84 (s, 3H), 7.54 (d, J=8.4 Hz, 1H), 8.14 (d, J=8.4 Hz, 1H)

Description 90

6-Cyclopropyl-pyridine-2,3-dicarboxylic acid (D90)

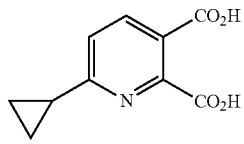 [SMILES: O=C(O)c1ccc(C2CC2)nc1C(=O)O]

To a solution of 6-cyclopropyl-pyridine-2,3-dicarboxylic acid dimethyl ester (D81, 12.6 g, 53.62 mmol) in methanol (90 ml) and water (30 ml) was added potassium hydroxide (9.02 g, 160.86 mmol) at 0~5° C. After heated to 60° C. for 2 hours, the mixture was acidified with 1N HCl until pH=5 and then concentrated to give D82 (21.34 g, containing KCl) as a grey solid.
$^1$H NMR (CD$_3$OD) δ ppm=1.11~1.13 (m, 4H), 2.20~2.23 (m, 1H), 7.39 (d, J=8.4 Hz, 1H), 8.19 (d, J=8.4 Hz, 1H).

Description 91

6-Cyclopropyl-pyridine-2,3-dicarboxylic acid 2-methyl ester (D91)

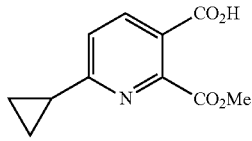 [SMILES: COC(=O)c1nc(C2CC2)ccc1C(=O)O]

A mixture of 6-cyclopropyl-pyridine-2,3-dicarboxylic acid (D82, 19.8 g, 95.6 mmol) in acetic anhydride (100 ml) was heated at 110° C. for 2 hours and then was concentrated in vacuum. To the residue was added methanol (100 ml) and stirring was continued at room temperature for 2 hours. The reaction mixture was concentrated in vacuum and the residue was purified by column chromatography on silica gel (10% ethyl acetate in petroleum ether) and C-18 reversed phase column (5% methanol/water to methanol) to give D83 (10.7 g) as a yellow solid.
$^1$H NMR (DMSO-d$_6$) δ ppm=0.88~0.91 (m, 2H), 0.97~1.00 (m, 2H), 2.14~2.15 (m, 1H), 3.75 (s, 3H), 7.35 (d, J=8.0 Hz, 1H), 8.09 (d, J=8.4 Hz, 1H)

Description 92

3-Amino-6-cyclopropyl-pyridine-2-carboxylic acid methyl ester (D92)

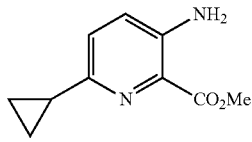 [SMILES: COC(=O)c1nc(C2CC2)ccc1N]

To a solution of 6-cyclopropyl-pyridine-2,3-dicarboxylic acid 2-methyl ester (D83, 10.7 g, 48.4 mmol) in toluene (200 ml) was added triethylamine (13.5 ml, 96.8 mmol), diphenyl azidophosphate (14.6 g, 53.2 mmol) and tert-butanol (56 ml). After refluxed for 5 hours, the resulting mixture was cooled to room temperature and concentrated to dryness. The residue was dissolved in ethyl acetate (200 ml) and washed with 5% citric acid (200 ml), aqueous sodium bicarbonate solution (200 ml) and brine (200 ml), dried over magnesium sulphate, filtered and evaporated to give a crude product for the next step used.
To a solution of the above residue in dichloromethane (150 ml) was added trifluoroacetic acid (20 ml) and the mixture was stirred at room temperature overnight. The solution was concentrated in vacuum. The residue was diluted with water and dichloromethane. The aqueous layers were extracted with dichloromethane. The combined extracts were washed with saturated sodium bicarbonate solution, brine, dried over magnesium sulphate, filtered and concentrated to give a crude product which was purified by flash chromatography on silica gel (10% ethyl acetate in petroleum ether) to afford D84 (3.67 g) as a yellow solid.
$^1$H NMR (CDCl$_3$) δ ppm=0.79~0.83 (m, 2H), 0.91~0.98 (m, 2H), 2.05~2.12 (m, 1H), 3.98 (s, 3H), 5.58 (s, 2H), 6.89 (d, J=8.8 Hz, 1H), 6.97 (d, J=8.4 Hz, 1H).

Description 93

6-Cyclopropyl-3-iodo-pyridine-2-carboxylic acid methyl ester (D93)

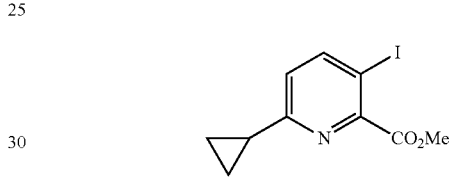

To a solution of 3-amino-6-cyclopropyl-pyridine-2-carboxylic acid methyl ester (D84, 2.0 g, 10.4 mmol) in water (40 ml) and 6N HCl (10.4 ml) was added drop wise a solution of sodium nitrite (1.08 g, 15.6 mmol) in water (20 ml) at 0~5° C. The reaction solution was stirred for 1 hour then a solution of potassium iodine (5.18 g, 31.2 mmol) in water (20 mL) below 10° C. was added. After stirred at room temperature overnight, the reaction solution was basified with saturated sodium carbonate solution until pH=8 and was extracted with ethyl acetate. The combined extracts were washed with brine, dried over magnesium sulphate, filtered and evaporated. The residue was purified by column chromatography on silica gel (5% ethyl acetate in petroleum ether) to give D85 (2.78 g) as colorless oil.
$^1$H NMR (CDCl$_3$) δ ppm=1.01~1.04 (m, 4H), 2.00~2.05 (m, H), 3.97 (s, 3H), 6.89 (d, J=8.4 Hz, 1H), 8.00 (d, J=8.4 Hz, 1H).

Description 94 methyl 6-cyclopropyl-3-phenylpicolinate (D94)

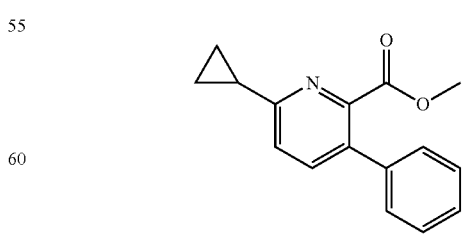

To a suspension of 6-Cyclopropyl-3-iodo-pyridine-2-carboxylic acid methyl ester (D85, 200 mg, 0.66 mmol), phenyl boronic acid (80.5 mg, 0.66 mmol) and Pd tetrakistriphenylphospine (76.3 mg; 0.066 mmol) in dry Toluene (3 ml) was added K$_2$CO$_3$ (1M acq solution, 0.66 ml, 0.66 mmol). The mixture was heated in microwave oven for 25 min at 120° C. The reaction mixture was diluted with AcOEt (10 mL) and water (10 mL). The organic layer was separated, washed with brine, dried over Na$_2$SO$_4$ and filtrated. The solvent was evaporated under reduced pressure; the crude mixture was purified on silica gel (Cyclohexane to Cyclohexane/AcOEt 9:1) to obtain 125 mg of the title compound as white solid.

MS (ESI) m/z: 254 [M+H]$^+$.

$^1$H NMR (CDCl3) δ ppm=7.62 (d, J=7.8 Hz, 1H), 7.50-7.31 (m, 5H), 7.23 (d, J=8.3 Hz, 1H), 3.73 (s, 3H), 2.17 (tt, J=5.0, 8.0 Hz, 1H), 1.13-1.02 (m, 4H).

Description 95

6-cyclopropyl-3-phenylpicolinic acid (D95)

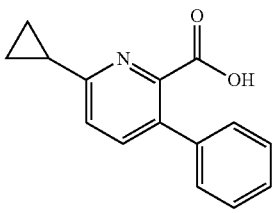 [SMILES: O=C(O)c1nc(C2CC2)ccc1-c1ccccc1]

(D94) (125 mg, 0.49 mmol) was suspended in 4 ml of a water/MeOH 1/1 mixture. LiOH (35 mg, 1.48 mmol) was added and the resulting mixture was heated to 80° C. for 1 hour. The methanol was then removed by distillation; the resulting solution was further diluted with water and washed with AcOEt. The basic aqueous phase was then acidified with aqueous HCl (4M) to pH 3 and evaporated. Residue was diluted in a small amount of MeOH and loaded on a SCX cartridge, which was then washed with MeOH, followed by a solution of ammonia 2.0 M in MeOH. The basic fractions were collected and evaporated. Yield 80 mg white solid.

MS (ESI) m/z: 240 [M+H]$^+$.

Description 96

6-methyl-3-(pyrimidin-2-yl)picolinic acid (D96)

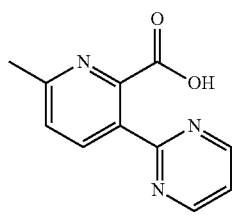 [SMILES: Cc1ccc(-c2ncccn2)c(C(=O)O)n1]

The 6-methyl-3-(pyrimidin-2-yl)picolinic acid was prepared according to the procedure described in WO2010063663.

Description 97

3-(4-fluorophenyl)-6-methylpicolinic acid (D97)

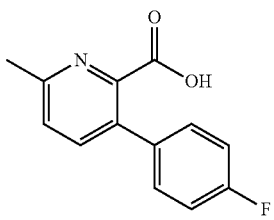 [SMILES: Cc1ccc(-c2ccc(F)cc2)c(C(=O)O)n1]

The 3-(4-fluorophenyl)-6-methylpicolinic acid was prepared according to the procedure described in WO2010063663.

Description 98

6-methyl-3-(3-methyl-1H-pyrazol-1-yl)picolinic acid (D98)

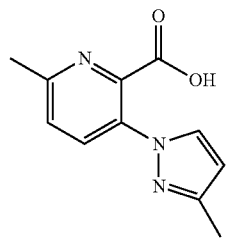 [SMILES: Cc1ccc(-n2ccc(C)n2)c(C(=O)O)n1]

The 6-methyl-3-(3-methyl-1H-pyrazol-1-yl)picolinic acid was prepared according to the procedure described in WO2010063663.

Description 99

6-methyl-3-(4-methyl-1H-pyrazol-1-yl)picolinic acid (D99)

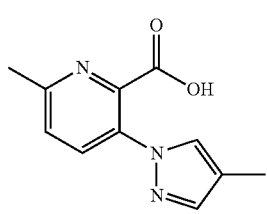

The 6-methyl-3-(4-methyl-1H-pyrazol-1-yl)picolinic acid was prepared according to the procedure described in WO2010063663.

Description 100

6-methyl-3-(thiazol-2-yl)picolinic acid (D100)

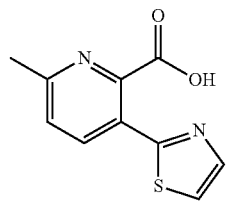

The 6-methyl-3-(thiazol-2-yl)picolinic acid was prepared according to the procedure described in WO2010063663.

EXAMPLES

Example 1

Preparation of Compounds 1a-o

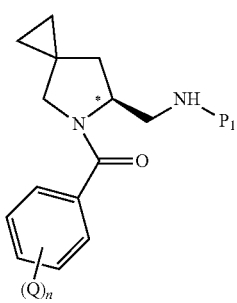

(IV)

Coupling General Procedure 1

Carboxylic acid (1.2 eq), HOBT (1.6 eq) and EDCI.HCl (1.6 eq) dissolved in dichloromethane (20 ml/mmol) were stirred at 25° C. for 0.5-2 hours, then (D27-46) (1 eq.) dissolved in dichloromethane were added. After 2 hours the mixture was poured in an aqueous saturated solution of $NaHCO_3$ and extracted with dichloromethane. The crude was purified by silica gel column chromatography (DCM to DCM/MeOH=9/1 or Cyclohexane/AcOEt=1/1 to AcOEt 100%))

Coupling General Procedure 2

Carboxylic acid (1.2 eq), N-methyl morpholine (3 eq) and 2-chloro-4,6-dimethoxy-1,3,5-triazine (1.2 eq) dissolved in dry 1,4-dioxane (20 ml/mmol) were stirred at 25° C. for 0.5 hours, then (D27-46) (1 eq.) dissolved in 1,4-dioxane were added. After 2-4 hours at 50-70° C. solvents were evaporated and residue was dissolved in EtOAc, washed with HCl 0.1N, NaOH 1N and brine. The crude was purified by silica gel column chromatography (DCM to DCM/MeOH=9/1)

Coupling General Procedure 3

Carboxylic acid, HOBT (1 eq) and EDCI.HCl (1.5 eq) dissolved in dichloromethane (5 ml/mmol) were stirred at 25° C. for 0.5-2 hours, then intermediates (D27-46) dissolved in dichloromethane were added. After 18 hours the mixture was poured in an aqueous saturated solution of $NaHCO_3$ and extracted with dichloromethane. The crude was purified by silica gel column chromatography (DCM to DCM/MeOH=9/1).

Coupling General Procedure 4

2-methyl-5-phenylthiazole-4-carboxylic acid (1.3 eq) and HOBT (2.3 eq) were suspended in dry DCM under nitrogen atmosphere. Then Si-DCC (silica supported carbodiimide from Silicycle, 2.5-3 eq) was added and the mixture was shaken for 10 minutes. After that, a solution of (D27-46) (1 eq) in dry dichloromethane was added and the mixture was shaken at room temperature for 18 hours. The supported reagent was then filtered and washed with MeOH and DCM. The liquid phase was evaporated; the obtained residue was taken up in DCM and the resulting solution washed with an aqueous saturated solution of $NaHCO_3$.

The organic layer was isolated and evaporated. The residue was then purified by flash chromatography on silica gel.

Coupling General Procedure 5

Carboxylic acid (1.1 q), HOBT (1.45 q) and EDCI.HCl (1.3 q) dissolved in DMF (1 ml/mmol) were stirred at 25° C. for 0.5-2 hours, then (D27-46) (1 eq.) dissolved in DMF were added. After 2 hours the mixture was diluted with dichloromethane, washed with an aqueous saturated solution of $NH_4Cl$ first and with an aqueous saturated solution of $NaHCO_3$ after.

The crude was purified by silica gel column chromatography (DCM to DCM/MeOH=9/1 or Cyclohexane/AcOEt=1/1 to AcOEt 100%).

Coupling General Procedure 6

Carboxylic acid (1.3 eq), HOBT (1.5 eq), HBTU (1.25 eq) and DIPEA (3 eq.) dissolved in DMF (15 ml/mmol) were stirred at 25° C. for 15 min, then (D27-46) (1 eq.) dissolved in DMF were added. After 18 hours solvents were evaporated, residue taken up with DCM (50 ml/mmol), washed with NaOH, dried with $Na_2SO_4$ and evaporated. The crude was purified by silica gel column chromatography (cyclohexane to cyclohexane/Acetone=75/25).

Coupling General Procedure 7

Carboxylic acid (1.0 q), HOBT (1.4 q) and EDCI.HCl (1.4 q) were suspended in dry DCM under nitrogen atmosphere and stirred at 25° C. for 0.5-2 hours, then (D27-46) (1 eq.) dissolved in DCM were added. After 2-18 hours the mixture was diluted with dichloromethane, washed with an aqueous saturated solution of $NH_4Cl$ first and with an aqueous saturated solution of $NaHCO_3$ after. The crude was purified by silica gel column chromatography (DCM to DCM/MeOH=9/1 or Cyclohexane/AcOEt=1/1 to AcOEt 100%).

Compound 1b was prepared by the commercially available carboxylic acid.

Compounds 1a-o were prepared according to general procedure 1-6:

| Comp. | Intermediate | Procedure | Yield % |
|---|---|---|---|
| | (D27), (D55) | 2 | 31 |

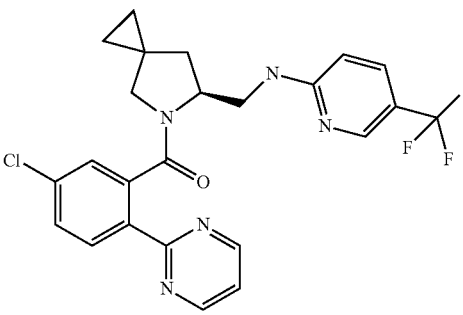

1a

¹H NMR (CDCl₃) δ ppm = 8.70 (br. s., 2 H), 8.43-8.26 (m, 2 H), 7.69-7.47 (m, 2 H), 7.43-6.64 (m, 5 H, under the solvent peak), 4.87-4.64 (m, 1 H), 4.00-2.91 (m, 3 H), 2.44-2.23 (m, 1 H), 1.83-1.62 (m, 1 H), 0.82-0.34 (m, 4 H)
ESI+ m/z 488 [M + H]⁺

(S)-(5-chloro-2-(pyrimidin-2-yl)phenyl)(6-(((5-(trifluoromethyl)pyridin-2-yl)amino)methyl)-5-azaspiro[2.4]heptan-5-yl)methanone.

| | (D27) | 5 | 82 |
|---|---|---|---|

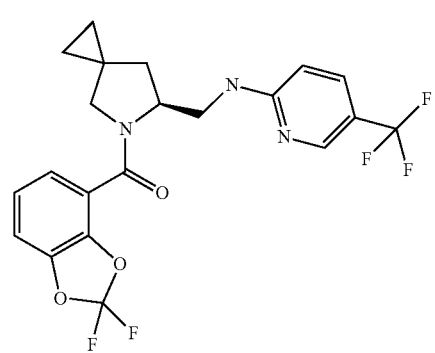 [SMILES: O=C(c1cccc2c1OC(F)(F)O2)N1CC2(CC2)C[C@H]1CNc1ccc(C(F)(F)F)cn1]

1b

¹H NMR (CDCl₃) δ ppm 8.41-7.98 (m, 1 H), 7.70-7.32 (m, 1 H), 7.21-7.00 (m, 3 H), 6.97-6.60 (m, 1 H), 6.58-5.96 (m, 1 H), 4.94-4.53 (m, 1 H), 4.03-3.70 (m, 2 H), 3.62-3.15 (m, 2 H), 2.64-2.08 (m, 1 H), 1.99-1.43 (m, 1 H), 0.87-0.40 (m, 4 H).
ESI+ m/z 456 H]⁺

(S)-(2,2-difluorobenzo[d][1,3]dioxol-4-yl)(6-(((5-(trifluoromethyl)pyridin-2-yl)amino)methyl)-5-azaspiro[2.4]heptan-5-yl)methanone.

| | (D27), (D60) | 2 | 48 |
|---|---|---|---|

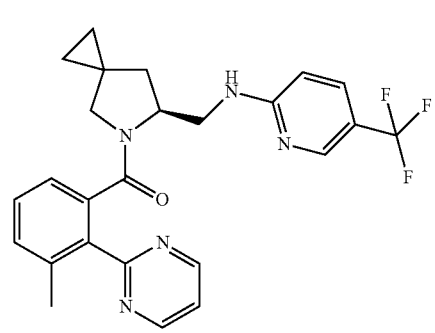 [SMILES: Cc1cccc(C(=O)N2CC3(CC3)C[C@H]2CNc2ccc(C(F)(F)F)cn2)c1-c1ncccn1]

1c

¹HNMR (Acetone-d6) δ ppm 8.82-8.93 (m, 2 H), 8.12-8.31 (m, 1 H), 7.61-7.64 (m, 1 H), 7.20-7.47 (m, 4 H), 6.60-6.85 (m, 2 H), 4.41-4.43 (m, 1 H), 3.54-3.61 (m, 2 H), 3.44-3.53 (m, 1 H), 3.11-3.27 (m, 1 H), 2.34-2.36 (m, 3 H), 2.15-2.20 (m, 1 H), 1.55-1.75 (m, 1 H), 0.56-0.73 (m, 4 H).
ESI+ m/z 468 [M + H]⁺

(S)-(3-methyl-2-(pyrimidin-2-yl)phenyl)(6-(((5-(trifluoromethyl)pyridin-2-yl)amino)methyl)-5-azaspiro[2.4]heptan-5-yl)methanone.

| Comp. | Intermediate | Procedure | Yield % |
|---|---|---|---|
| | (D27), (D64) | 2 | 58 |

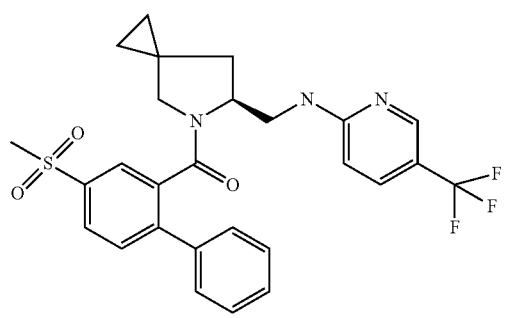 [SMILES: CS(=O)(=O)c1ccc(-c2ccccc2)c(C(=O)N2CC3(CC3)C[C@H]2CNc2ccc(C(F)(F)F)cn2)c1]

1d

¹H NMR (CDCl₃) δ ppm = 8.10-8.35 (m, 1 H), 8.04-8.08 (m, 2 H), 7.57-7.66 (m, 2 H), 7.40-7.51 (m, 4 H), 7.30 (b.s, 1 H), 6.51-6.53 (m, 1 H), 6.12-6.26 (m, 1 H), 4.63-4.78 (m, 1 H), 3.43-3.74 (m, 2 H), 3.24-3.27 (m, 1 H), 3.06-3.13 (m, 3 H), 2.89-2.91 (m, 1 H), 1.46-1.50 (m, 1 H), 0.19-0.61 (m, 4 H).
ESI+ m/z 530 [M + H]⁺

(S)-(4-(methylsulfonyl)-[1,1'-biphenyl]-2-yl)(6-(((5-(trifluoromethyl)pyridin-2-yl)amino)methyl)-5-azaspiro[2.4]heptan-5-yl)-methanone.

| | (D27), (D72) | 2 | 24 |
|---|---|---|---|

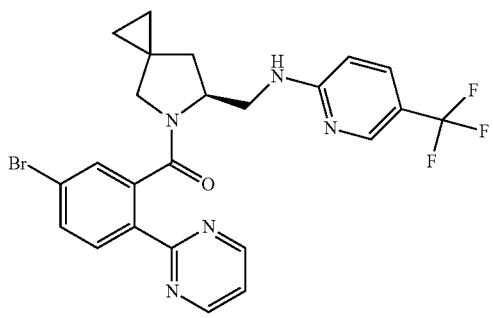 [SMILES: O=C(c1cc(Br)ccc1-c1ncccn1)N1CC2(CC2)C[C@H]1CNc1ccc(C(F)(F)F)cn1]

1e

¹H NMR (CDCl₃) δ ppm = 8.88-8.83 (m, 2 H), 8.28-8.24 (m, 1 H), 8.16-7.74 (m, 1 H), 7.62-6.71 (m, 4 H), 4.67-4.66 (m, 1 H), 3.95-377 (m, 1 H), 3.53-3.41 (m, 2 H), 3.16-3.09 (m, 3 H), 2.29-177 (m, 1 H), 1.31-0.45 (m, 4 H).
ESI+ m/z 532-534 [M + H]⁺

(S)-(5-bromo-2-(pyrimidin-2-yl)phenyl)(6-(((5-(trifluoromethyl)pyridin-2-yl)amino)methyl)-5-azaspiro[2.4]heptan-5-yl)-methanone.

| | (D40), (D55) | 2 | 26 |
|---|---|---|---|

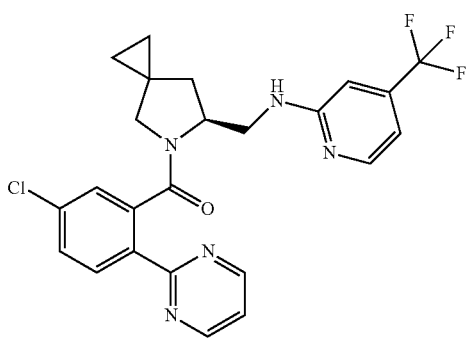 [SMILES: O=C(c1cc(Cl)ccc1-c1ncccn1)N1CC2(CC2)C[C@H]1CNc1cc(C(F)(F)F)ccn1]

1f

¹H NMR (Acetone) δ ppm = 8.96-8.30 (m, 3 H), 8.25 (d, J = 4.9 Hz, 1 H), 7.67-7.32 (m, 3 H), 6.93-6.46 (m, 3 H), 4.66 (d, J = 4.4 Hz, 1 H), 4.16-3.04 (m, 4 H), 2.28 (dd, J = 8.3, 12.2 Hz, 1 H), 1.79 (d, J = 11.7 Hz, 1 H), 0.83-0.40 (m, 4 H)
ESI+ m/z 488 [M + H]⁺

(S)-(5-chloro-2-(pyrimidin-2-yl)phenyl)(6-(((4-(trifluoromethyl)pyridin-2-yl)amino)methyl)-5-azaspiro[2.4]heptan-5-yl)methanone.

-continued

| Comp. | Intermediate | Procedure | Yield % |
|---|---|---|---|
| | (D30), (D79) | 2 | 26 |

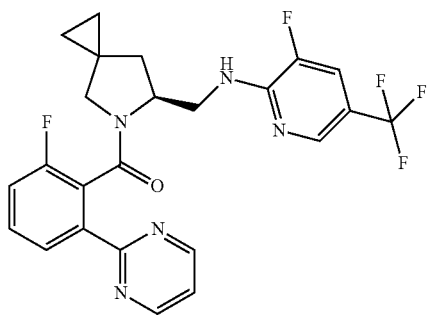 [SMILES: O=C(c1c(F)cccc1-c1ncccn1)N1CC2(CC2)C[C@H]1CNc1ncc(C(F)(F)F)cc1F]

1g

¹H NMR (Acetone) δ ppm = 9.00-8.71 (m, 2 H), 8.35-7.96 (m, 2 H), 7.91-7.22 (m, 5 H), 4.79 (d, J = 4.4 Hz, 1 H), 4.23-3.11 (m, 4 H), 2.52-2.30 (m, 1 H), 1.89-1.65 (m, 1 H), 0.92-0.44 (m, 4 H).
ESI+ m/z 490 [M + H]⁺

(S)-(6-(((3-fluoro-5-(trifluoromethyl)pyridin-2-yl)amino)methyl)-5-azaspiro[2.4]heptan-5-yl)(2-fluoro-6-(pyrimidin-2-yl)phenyl)methanone.

| | (D40), (D79) | 2 | 17 |
|---|---|---|---|

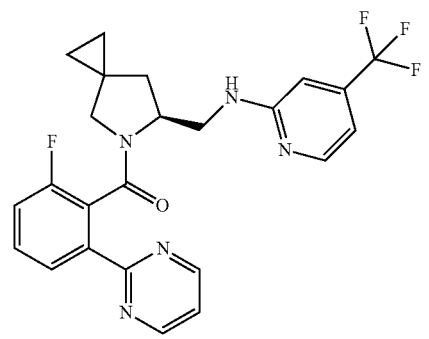 [SMILES: O=C(c1c(F)cccc1-c1ncccn1)N1CC2(CC2)C[C@H]1CNc1cc(C(F)(F)F)ccn1]

1h

¹H NMR (Acetone) δ ppm = 9.08-8.70 (m, 2 H), 8.38-7.81 (m, 2 H), 7.69-7.17 (m, 3 H), 6.99-6.40 (m, 2 H), 4.66 (d, J = 6.8 Hz, 1 H), 4.16-3.13 (m, 4 H, under the solvent peak), 2.49-2.25 (m, 1 H), 1.93-1.37 (m, 1 H), 1.27-0.39 (m, 4 H).
ESI+ m/z 472 [M + H]⁺

(S)-(2-fluoro-6-(pyrimidin-2-yl)phenyl)(6-(((4-(trifluoromethyl)pyridin-2-yl)amino)methyl)-5-azaspiro[2.4]heptan-5-yl)methanone.

| | (D30), (D83) | 2 | 30 |
|---|---|---|---|

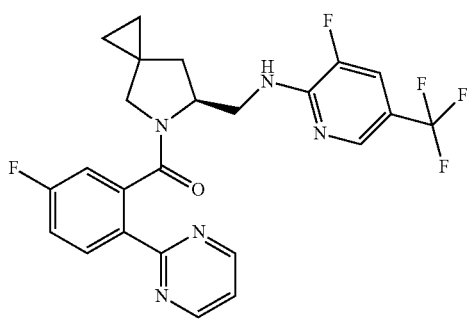 [SMILES: O=C(c1cc(F)ccc1-c1ncccn1)N1CC2(CC2)C[C@H]1CNc1ncc(C(F)(F)F)cc1F]

1i

¹H NMR (Acetone) δ ppm = 8.99-8.74 (m, 2 H), 8.48-7.80 (m, 2 H), 7.63-6.88 (m, 5 H), 4.88-4.68 (m, 1 H), 4.25-3.02 (m, 4 H), 2.35 (dd, J = 8.1, 12.5 Hz, 1 H), 1.76 (d, J = 11.2 Hz, 1 H), 1.47 (d, J = 12.7 Hz, 1 H), 1.37-0.37 (m, 4 H).
ESI+ m/z 490 [M + H]⁺

(S)-(2-fluoro-6-(pyrimidin-2-yl)phenyl)(6-(((4-(trifluoromethyl)pyridin-2-yl)amino)methyl)-5-azaspiro[2.4]heptan-5-yl)methanone.

| Comp. | Intermediate | Procedure | Yield % |
|---|---|---|---|
| | (D41), (D83) | 2 | 20 |

1j

¹H NMR (Acetone) δ ppm = 8.99-8.75 (m, 2 H), 8.37 (dd, J = 5.9, 8.8 Hz, 1 H), 7.49-7.06 (m, 3 H), 6.78-6.17 (m, 2 H), 4.63 (d, J = 4.9 Hz, 1 H), 4.12-3.03 (m, 4 H), 2.28 (dd, J = 8.1, 12.5 Hz, 1 H), 1.79 (d, J = 11.2 Hz, 1 H), 1.36-0.43 (m, 4 H).
ESI+ m/z 485-488 [M + H]⁺

(S)-(5-fluoro-2-(pyrimidin-2-yl)phenyl)(6-(((6-methyl-4-(trifluoromethyl)pyridin-2-yl)amino)methyl)-5-azaspiro[2.4]heptan-5-yl)-methanone.

| | (D40), (D83) | 2 | 25 |
|---|---|---|---|

1k

¹H NMR (Acetone) δ ppm = 9.03-8.71 (m, 2 H), 8.49-7.86 (m, 2 H), 7.51-7.07 (m, 3 H), 7.00-6.41 (m, 3 H), 4.65 (d, J = 4.4 Hz, 1 H), 4.19-3.03 (m, 4 H), 2.28 (dd, J= 8.1, 12.5 Hz, 1 H), 1.87-1.27 (m, 1 H), 1.26-0.35 (m, 4 H).
ESI+ m/z 472 [M + H]⁺

(S)-(5-fluoro-2-(pyrimidin-2-yl)phenyl)(6-(((4-(trifluoromethyl)pyridin-2-yl)amino)methyl)-5-azaspiro[2.4]heptan-5-yl)methanone.

| | (D30), (D84) | 2 | 20 |
|---|---|---|---|

1l

¹H NMR (Acetone) δ ppm = 8.95-8.61 (m, 2 H), 8.35-7.83 (m, 2 H), 7.78-7.09 (m, 5 H), 4.95-4.64 (m, 1 H), 4.13-2.99 (m, 4 H), 2.37-2.24 (m, 1 H), 1.74 (d, J = 11.7 Hz, 1 H), 0.89-0.36 (m, 4 H).
ESI+ m/z 486 [M + H]⁺

(S)-(6-(((3-fluoro-5-(trifluoromethyl)pyridin-2-yl)amino)methyl)-5-azaspiro[2.4]heptan-5-yl)(5-methyl-2-(pyrimidin-2-yl)phenyl)-methanone.

| Comp. | Intermediate | Procedure | Yield % |
|---|---|---|---|
| | (D41), (D84) | 2 | 13 |

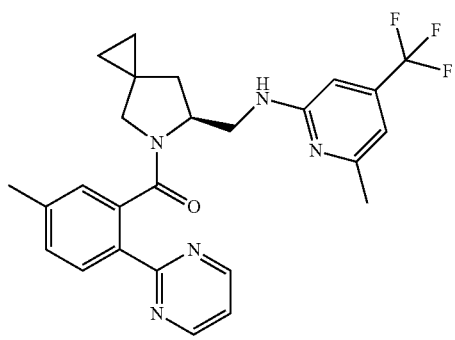 [SMILES: Cc1ccc(-c2ncccn2)c(C(=O)N2CC3(CC3)C[C@H]2CNc2cc(C(F)(F)F)cc(C)n2)c1]

1m

¹H NMR (Acetone) δ ppm = 8.97-8.06 (m, 3 H), 7.49-7.01 (m, 3 H), 6.88-6.39 (m, 2 H), 4.65 (d, J = 5.4 Hz. 1 H), 4.18-2.97 (m, 4 H), 2.35-2.26 (m, 1 H), 1.77 (d, J = 12.7 Hz, 1 H), 1.31 (br. s., 1 H), 1.03-0.28 (m, 4 H).
ESI+ m/z 482 [M + H]⁺

(S)-(5-methyl-2-(pyrimidin-2-yl)phenyl)(6-(((6-methyl-4-(trifluoromethyl)pyridin-2-yl)amino)methyl)-5-azaspiro[2.4]heptan-5-yl)-methanone.

| | (D40), (D84) | 2 | 17 |
|---|---|---|---|

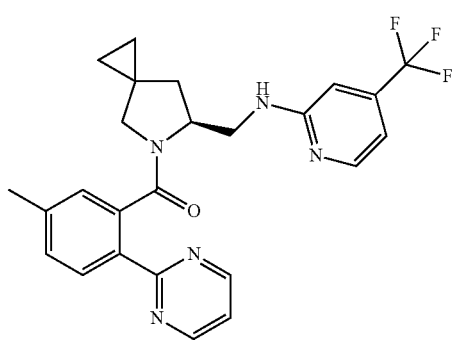 [SMILES: Cc1ccc(-c2ncccn2)c(C(=O)N2CC3(CC3)C[C@H]2CNc2cc(C(F)(F)F)ccn2)c1]

1n

¹H NMR (Acetone) δ ppm = 8.95-7.89 (m, 4 H), 7.47-7.03 (m, 3 H), 7.00-6.37 (m, 2 H), 4.67 (d, J = 5.4 Hz, 1 H), 4.13-3.44 (m, 2 H), 3.32 (s, 2 H), 2.29 (dd, J = 8.1, 12.5 Hz, 1 H), 1.76 (d, J = 11.7 Hz, 1 H), 0.92-0.38 (m, 4 H).
ESI+ m/z 468 [M + H]⁺

(S)-(5-methyl-2-(pyrimidin-2-yl)phenyl)(6-(((4-(trifluoromethyl)pyridin-2-yl)amino)methyl)-5-azaspiro[2.4]heptan-5-yl)methanone.

| | (D27), (D84) | 2 | 25 |
|---|---|---|---|

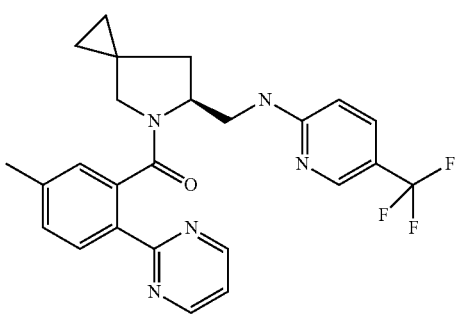 [SMILES: Cc1ccc(-c2ncccn2)c(C(=O)N2CC3(CC3)C[C@H]2CNc2ccc(C(F)(F)F)cn2)c1]

1o

¹H NMR (CDCl3) δ ppm = 8.97-8.55 (m, 2 H), 8.46-8.09 (m, 2 H), 7.60-7.30 (m, 2 H), 7.25-6.92 (m, 2 H), 6.55 (d, J = 8.8 Hz, 1 H), 4.84 (d, J = 4.9 Hz, 1 H), 4.04-2.73 (m, 4 H), 2.29 (dd, J = 8.3, 12.7 Hz, 1 H), 1.63 (d, J = 8.8 Hz, 1 H), 1.03-0.03 (m, 4 H).
ESI+ m/z 468 [M + H]⁺

(S)-(5-methyl-2-(pyrimidin-2-yl)phenyl)(6-(((5-(trifluoromethyl)pyridin-2-yl)amino)methyl)-5-azaspiro[2.4]heptan-5-yl)-methanone

| Comp. | Intermediate | Procedure | Yield % |
|---|---|---|---|
| | (D43), (D84) | 2 | 17 |

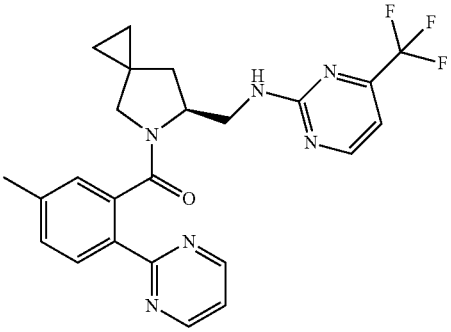 [SMILES: Cc1ccc(-c2ncccn2)c(C(=O)N2CC3(CC3)C[C@H]2CNc2nccc(C(F)(F)F)n2)c1]

1p $^1$H NMR (CD3OD) δ ppm = 8.86-8.83 (m, 2 H), 8.56-8.13 (m, 2 H), 7.40-7.33 (m, 2 H), 7.25-7.09 (m, 1 H), 6.81-6.94 (m, 1 H), 4.71-4.69 (m, 1 H), 4.15-3.88 (m, 2 H), 3.04-2.99 (m, 1 H), 2.43-2.38 (m, 3 H), 2.30-2.25 (m, 1 H), 1.74-1.71 (m, 1 H), 1.40-1.24 (m, 1 H), 0.73-0.42 (m, 4 H).
ESI+ m/z 469 [M + H]$^+$ (S)-(5-methyl-2-(pyrimidin-2-yl)phenyl)(6-(((4-(trifluoromethyl)pyrimidin-2-yl)amino)methyl)-5-azaspiro[2.4]heptan-5-yl)methanone

| | (D43), (D55) | 2 | 25 |
|---|---|---|---|

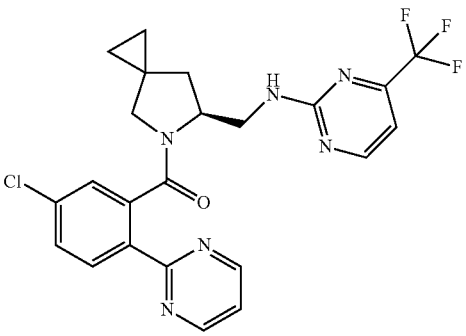 [SMILES: O=C(c1cc(Cl)ccc1-c1ncccn1)N1CC2(CC2)C[C@H]1CNc1nccc(C(F)(F)F)n1]

1q $^1$H NMR (CD3OD) δ ppm = 8.88-8.85 (m, 2 H), 8.55-8.23 (m, 2 H), 7.59-7.37 (m, 3 H), 6.94-6.81 (m, 1 H), 4.73-4.69 (m, 1 H), 4.02-3.87 (m, 2 H), 3.61-3.40 (m, 1 H), 3.35-3.08 (m, 1 H), 2.30-2.25 (m, 1 H), 1.76-1.72 (m, 1 H), 0.75-0.42 (m, 4 H).
ESI+ m/z 489 [M + H]$^+$ ((S)-(5-chloro-2-(pyrimidin-2-yl)phenyl)(6-(((4-(trifluoromethyl)pyrimidin-2-yl)amino)methyl)-5-azaspiro[2.4]heptan-5-yl)methanone

| | (D44), (D84) | 2 | 31 |
|---|---|---|---|

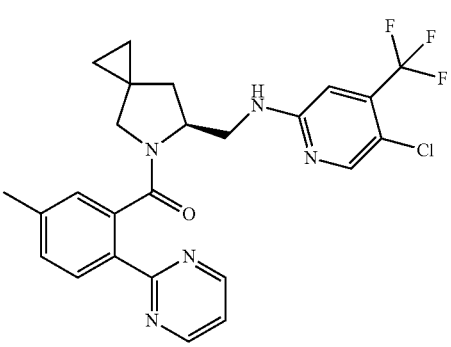 [SMILES: Cc1ccc(-c2ncccn2)c(C(=O)N2CC3(CC3)C[C@H]2CNc2cc(C(F)(F)F)c(Cl)cn2)c1]

1r $^1$H NMR (Acetone) δ ppm = 8.88-8.81 (m, 2 H), 8.23-8.21 (m, 2 H), 7.39-7.0 (m, 4 H), 4.69-4.62 (m, 1 H), 3.92-3.85 (m, 1 H), 3.77-3.70 (m, 1 H), 3.61-3.40 (m, 1 H), 3.34-3.32 (m, 1 H), 3.23-3.02 (m, 1 H), 2.42-2.37 (m, 3 H), 2.32-2.26 (m, 1 H), 1.76-1.73 (m, 1 H), 0.73-0.45 (m, 4 H).
ESI+ m/z 502 [M + H]$^+$ (S)-(6-(((5-chloro-4-(trifluoromethyl)pyridin-2-yl)amino)methyl)-5-azaspiro[2.4]heptan-5-yl)(5-methyl-2-(pyrimidin-2-yl)phenyl)-methanone

| Comp. | Intermediate | Procedure | Yield % |
|---|---|---|---|
| | (D45), (D84) | 2 | 9 |

1s

¹H NMR (Acetone) δ ppm = 8.88-8.83 (m, 2 H), 8.64-8.28 (m, 2 H), 8.24-8.13 (m, 1 H), 7.84-7.78 (m, 1 H), 7.38-7.20 (m, 3 H), 4.76-4.70 (m, 1 H), 3.91-3.61 (m, 2 H), 3.36-3.07 (m, 1 H), 2.42-2.39 (m, 3 H), 2.34-2.29 (m, 1 H), 1.76-1.72 (m, 1 H), 0.70-0.47 (m, 4 H).
ESI+ m/z 469 [M + H]⁺

(S)-(5-methyl-2-(pyrimidin-2-yl)phenyl)(6-(((5-(trifluoromethyl)pyrimidin-2-yl)amino)methyl)-5-azaspiro[2.4]heptan-5-yl)methanone

| | (D44), (D55) | 2 | 9 |
|---|---|---|---|

1t

¹H NMR (Acetone) δ ppm = 8.91-8.86 (m, 2 H), 8.34-8.24 (m, 1 H), 8.21-7.89 (m, 1 H), 7.60-7.39 (m, 3 H), 7.03-7.0 (m, 1 H), 4.66-4.64 (m, 1 H), 3.92-3.87 (m, 1 H), 3.57-3.81 (m, 1 H), 3.50-3.36 (m, 1 H), 2.33-2.26 (m, 1 H), 1.80-1.76 (m, 1 H), 1.37-1.31 (m, 1 H), 0.74-0.48 (m, 4 H).
ESI+ m/z 522-524 [Cl pattern]

(S)-(5-chloro-2-(pyrimidin-2-yl)phenyl)(6-(((5-chloro-4-(trifluoromethyl)pyridin-2-yl)amino)methyl)-5-azaspiro[2.4]heptan-5-yl)methanone

| | (D45), (D55) | 2 | 33 |
|---|---|---|---|

1u

¹H NMR (Acetone) δ ppm = 8.91-8.88 (m, 2 H), 8.64 (m, 1 H), 8.53 (m, 1 H), 8.35-8.33 (m, 1 H), 7.61-7.52 (m, 1 H), 7.48-7.42 (m, 2 H), 4.80-4.69 (m, 1 H), 3.93-3.87 (m, 2 H), 3.41-3.38 (m, 1 H), 3.16 (m, 1 H), 2.34-2.29 (m, 1 H), 1.78-1.75 (m, 1 H), 0.74-0.49 (m, 4 H).
ESI+ m/z 489 [M + H]⁺

(S)-(5-chloro-2-(pyrimidin-2-yl)phenyl)(6-(((5-(trifluoromethyl)pyrimidin-2-yl)amino)methyl)-5-azaspiro[2.4]heptan-5-yl)methanone

-continued

| Comp. | Intermediate | Procedure | Yield % |
|---|---|---|---|
| | (D46), (D55) | 2 | 20 |

1v

¹H NMR (Acetone) δ ppm = 8.92-8.87 (m, 2 H), 8.35-8.33 (m, 2 H), 7.61-7.50 (m, 1 H), 7.44-7.30 (m, 4 H), 4.68-4.61 (m, 1 H), 3.96-3.84 (m, 1 H), 3.40-3.37 (m, 1 H), 3.24-3.06 (m, 1 H), 2.33-2.28 (m, 1 H), 1.79-1.76 (m, 1 H), 2.34-2.29 (m, 1 H), 0.74-0.48 (m, 4 H). ESI+ m/z 522-524 [Cl pattern]

(S)-(5-chloro-2-(pyrimidin-2-yl)phenyl)(6-(((4-chloro-5-(trifluoromethyl)pyridin-2-yl)amino)methyl)-5-azaspiro[2.4]heptan-5-yl)-methanone

Example 2

Preparation of Compounds 2a-k

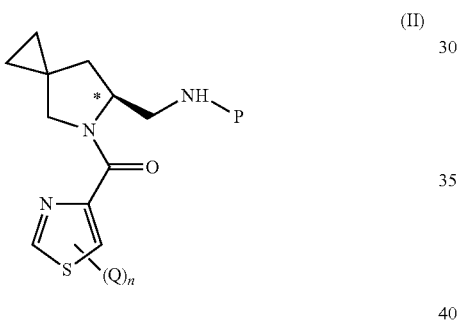

(II)

Carboxylic acids were prepared according to U.S. Pat. No. 3,282,927 for the compounds 2a-i. Compounds 2a-i were prepared according to the general procedure 1-6 described in example 1:

| Comp. | Intermediate | Procedure | Yield % |
|---|---|---|---|
| | (D36) (D85) | 3 | 38 |

2a

¹HNMR (CDCl₃) δ ppm 7.91-8.02 (m, 1 H), 7.23-7.46 (m, 6 H), 6.07-6.51 (m, 2 H), 4.73-4.98 (m, 1 H), 3.62-4.1 (m, 1 H), 3.48-3.84 (m, 1 H), 2.91-3.37 (m, 1 H), 3.28 (m, 1 H), 2.63-2.72 (m, 3 H), 2.12 (m, 1 H), 1.56-1.68 (m, 1 H), 1.18-1.27 (m, 1 H), 0.35-0.63 (m, 4 H) ESI+ m/z 461 [M + Na]⁺

(S)-(6-(((5-chloropyridin-2-yl)amino)methyl)-5-azaspiro[2.4]heptan-5-yl)(2-methyl-5-phenylthiazol-4-yl)methanone.

-continued

| Comp. | Intermediate | Procedure | Yield % |
| --- | --- | --- | --- |
| (D35) | (D85) | 6 | 94 |

¹H NMR (CDCl₃) δ ppm = 7.47-7.50 (m, 2 H), 7.21-7.44 (m, 7 H, under the solvent peak), 7.09-7.13 (m, 1 H), 7.45-7.49 (m, 1 H), 3.78-3.94 (m, 2 H), 3.24-3.39 (m, 1 H), 3.06-3.08 (m, 1 H), 2.61-2.73 (m, 3 H), 2.14-2.19 (m, 1 H), 1.67-1.71 (m, 1 H), 0.35-0.69 (m, 4 H).
ESI+ m/z 446 [M + H]⁺

2b (S)-(6-((benzo[d]oxazol-2-ylamino)methyl)-5-azaspiro[2.4]heptan-5-yl)(2-methyl-5-phenylthiazol-4-yl)methanone.

| | (D37) | (D85) | 3 | 34 |
| --- | --- | --- | --- | --- |

¹HNMR (CDCl₃) δ ppm 7.20-7.40 (m, 6 H), 6.43 (m, 1 H), 5.50-5.78 (m, 1 H), 4.70 (m, 1 H), 3.47-4.07 (m, 1 H), 3.76 (m, 1 H), 2.90-3.39 (m, 2 H), 2.66-2.72 (m, 3 H), 2.32-2.38 (m, 3 H), 2.08 (m, 1 H), 1.63-1.76 (m, 1 H), 1.22-1.33 (m, 1 H), 0.33-0.66 (m, 4 H)
ESI+ m/z 419 [M + H]⁺

2c (S)-(2-methyl-5-phenylthiazol-4-yl)(6-((((6-methylpyridin-2-yl)amino)methyl)-5-azaspiro[2.4]heptan-5-yl)methanone.

| | (D27) | (D85) | 1 | 80 |
| --- | --- | --- | --- | --- |

¹HNMR (CDCl₃) δ ppm 8.24-8.34 (m, 1 H), 7.25-7.58 (m, 7 H), 6.61 (m, 1 H), 4.78 (m, 1 H), 3.62-3.76 (m, 1 H), 2.95-3.39 (m, 2 H), 2.62-2.75 (m, 3 H), 1.59-2.19 (m, 3 H), 0.38-0.67 (m, 4 H),
ESI+ m/z 473-474 [M + H]⁺

2d (S)-(2-methyl-5-phenylthiazol-4-yl)(6-(((5-(trifluoromethyl)pyridin-2-yl)amino)methyl)-5-azaspiro[2.4]heptan-5-yl)methanone.

| Comp. | Intermediate | Procedure | Yield % |
| --- | --- | --- | --- |
| (D28) | (D85) | 4 | 65 |

¹HNMR (CDCl₃) δ ppm 7.84-8.13 (m, 2 H), 7.39-7.69 (m, 6 H), 6.95-7.14 (m, 4 H), 5.04 (m, 1 H), 3.73-3.94 (m, 2 H), 3.35-3.38 (m, 1 H), 2.86-2.89 (m, 1 H), 2.76 (s, 3 H), 2.25-2.30 (m, 1 H), 0.86-0.90 (m, 1 H), 0.35-0.68 (m, 4 H).
ESI+ m/z 455 [M + H]⁺

2e (S)-(6-((isoquinolin-1-ylamino)methyl)-5-azaspiro[2.4]heptan-5-yl)(2-methyl-5-phenylthiazol-4-yl)methanone.

| | | | |
| --- | --- | --- | --- |
| (D38) | (D85) | 4 | 88 |

¹HNMR (CDCl₃) δ ppm 7.35-7.54 (m, 5 H), 6.32 (s, 1 H), 4.07-4.67 (m, 1 H), 3.85 (m, 1 H), 3.33-3.55 (m, 1 H), 2.96-3.22 (m, 1 H), 2.70-2.74 (m, 3 H), 2.26-2.31 (m, 6 H), 1.77-2.07 (m, 1 H), 0.29-0.70 (m, 5 H)
ESI+ m/z 434 [M + H]⁺

2f (S)-(6-(((4,6-dimethylpyrimidin-2-yl)amino)methyl)-5-azaspiro[2.4]heptan-5-yl)(2-methyl-5-phenylthiazol-4-yl)methanone.

| | | | |
| --- | --- | --- | --- |
| (D39) | (D85) | 4 | 70 |

¹HNMR (CDCl₃) δ ppm 8.14-8.23 (m, 2 H), 7.32-7.52 (m, 5 H), 6.41 (m, 1 H), 4.75 (m, 1 H), 3.84-4.15 (m, 1 H), 3.73 (m, 1 H), 3.28-3.44 (m, 1 H), 2.98-3.24 (m, 1 H), 2.70-2.74 (m, 3 H), 2.07-2.12 (m, 1 H) 1.25-1.30 (m, 1 H) 0.32-0.68 (m, 4 H)
ESI+ m/z 440-442 [M + H]⁺

2g (S)-(6-(((5-chloropyrimidin-2-yl)amino)methyl)-5-azaspiro[2.4]heptan-5-yl)(2-methyl-5-phenylthiazol-4-yl)methanone.

| Comp. | Intermediate | Procedure | Yield % |
|---|---|---|---|
| (D33) | (D85) | 4 | 79 |

2h

¹HNMR (CDCl₃) δ ppm 7.26-7.54 (m, 8 H), 7.02-7.08 (m, 1 H), 4.75 (m, 1 H), 3.81-3.96 (m, 1 H), 3.26-3.38 (m, 1 H), 3.01-3.03 (m, 1 H), 2.69-2.75 (m, 3 H), 2.15-2.21 (m, 1 H), 1.67-1.70 (m, 1 H), 1.28-1.33 (m, 1 H), 0.36-0.71 (m, 4 H)
ESI+ m/z 479 [M + H]⁺

(S)-(6-(((6-fluorobenzo[d]thiazol-2-yl)amino)methyl)-5-azaspiro[2.4]heptan-5-yl)(2-methyl-5-phenylthiazol-4-yl)methanone.

| | | | |
|---|---|---|---|
| (D34) | (D85) | 4 | 72 |

2i

¹HNMR (CDCl₃) δ ppm = 7.26-7.56 (m, 9 H), 4.77 (m, 1 H), 3.78-3.88 (m, 1 H), 3.26-3.36 (m, 1 H), 3.01-3.04 (m, 1 H), 2.68-2.74 (m, 3 H), 2.15-2.20 (m, 1 H), 1.65-1.69 (m, 1 H), 1.27-1.33 (m, 1 H), 0.35-0.71 (m, 4 H)
ESI+ m/z 496 [M + H]⁺

(S)-(6-(((6-chlorobenzo[d]thiazol-2-yl)amino)methyl)-5-azaspiro[2.4]heptan-5-yl)(2-methyl-5-phenylthiazol-4-yl)methanone.

| | | | |
|---|---|---|---|
| (D40) | D(85) | 7 | 69 |

2j

¹H NMR (Acetone) δ ppm = 8.35-8.06 (m, 1 H), 7.68-7.28 (m, 5 H), 6.98-6.33 (m, 3 H), 4.80-4.18 (m, 1 H), 3.95-3.47 (m, 2 H), 3.40-2.98 (m, 2 H), 2.74-2.51 (m, 3 H), 2.18 (dd, J = 7.8, 12.7 Hz, 1 H), 1.94-1.22 (m, 1 H), 0.80-0.21 (m, 4 H).
ESI+ m/z 472-475 [M + H]⁺

(S)-(2-methyl-5-phenylthiazol-4-yl)(6-(((4-(trifluoromethyl)pyridin-2-yl)amino)methyl)-5-azaspiro[2.4]heptan-5-yl)methanone.

| Comp. | Intermediate | Procedure | Yield % |
|---|---|---|---|
| | (D41) (D85) | 7 | 70 |

<sup>1</sup>H NMR (Acetone) δ ppm = 7.72-7.25 (m, 5 H), 6.80-6.51 (m, 2 H), 6.40-6.12 (m, 1 H), 4.75-4.22 (m, 1 H), 3.93-3.03 (m, 4 H), 2.73-2.53 (m, 3 H), 2.47-2.27 (m, 3 H), 2.18 (dd, J = 8.1, 12.5 Hz, 1 H), 1.87-1.36 (m, 1 H), 0.95-0.35 (m, 4 H)
ESI+ m/z 486-489 [M + H]$^+$ 2k (S)-(6-(((6-methyl-4-(trifluoromethyl)pyridin-2-yl)amino)methyl)-5-azaspiro[2.4]heptan-5-yl)(2-methyl-5-phenylthiazol-4-yl)methanone.

Example 3

Preparation of Compounds 3a-r

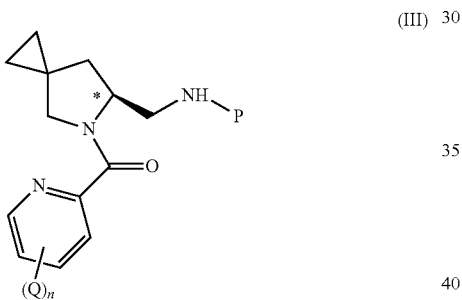

(III)

Carboxylic acids for the compounds 3a-j were prepared according WO2010063663; compounds 3a-o were prepared according to the general procedure 1-6 described in example 1.

| Comp. | Intermediate | Procedure | Yield % |
|---|---|---|---|
| | (D27) (D96) | 2 | 32 |

<sup>1</sup>HNMR (CDCl$_3$) δ ppm 8.6-8.85 (m, 1 H), 8.36-8.58 (m, 1 H), 8.19-8.33 (m, 1 H), 7.47-7.50 (m, 1 H), 7.27-7.34 (m, 2 H), 7.08-7.19 (m, 2 H), 6.01-6.50 (m, 1 H), 4.73-4.87 (m, 1 H), 3.64-3.87 (m, 2 H), 3.35-3.48 (m, 1 H) 3.10-3.13 (m, 1 H) 2.56-2.67 (m, 3 H) 2.37-2.53 (m, 1 H), 1.60-1.66 (m, 1 H), 0.45-0.77 (m, 4 H)
ESI+ m/z 469 [M + H]$^+$ 3a (S)-(6-methyl-3-(pyrimidin-2-yl)pyridin-2-yl)(6-(((5-(trifluoromethyl)pyridin-2-yl)amino)methyl)-5-azaspiro[2.4]heptan-5-yl)methanone.

-continued

| Comp. | Intermediate | Procedure | Yield % |
|---|---|---|---|
| | (D27) (D57) | 2 | 43 |

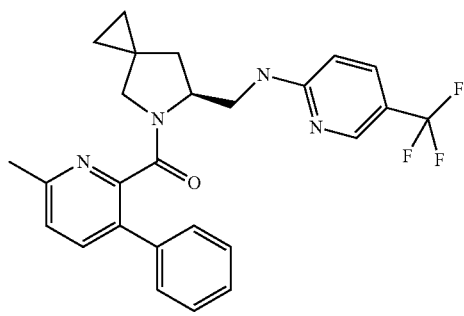 [SMILES: Cc1ccc(-c2ccccc2)c(C(=O)N2CC3(CC3)C[C@H]2CNc2ccc(C(F)(F)F)cn2)n1]

3b

¹HNMR (DMSO) δ ppm 7.97-8.29 (m, 1 H), 7.65-7.82 (m, 2 H), 7.28-7.52 (m, 7 H), 6.21-6.65 (m, 1 H), 3.71-4.28 (m, 1 H), 3.41-3.58 (m, 1 H), 3.09-3.28 (m, 2 H), 2.68-2.76 (m, 1 H), 2.47-2.53 (m, 3 H), 1.92-1.97 (m, 1 H) 1.51-1.54 (m, 1 H) 1.18-1.24 (m, 1 H) 0.34-0.63 (m, 4 H).
ESI+ m/z 466-468 [M + H]⁺

(S)-(6-methyl-3-phenylpyridin-2-yl)(6-(((5-(trifluoromethyl)pyridin-2-yl)amino)methyl)-5-azaspiro[2.4]heptan-5-yl)methanone.

| | (D29) (D96) | 2 | 35 |
|---|---|---|---|

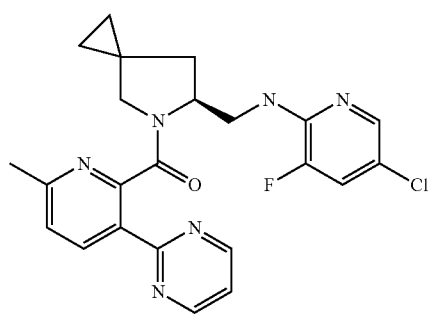 [SMILES: Cc1ccc(-c2ncccn2)c(C(=O)N2CC3(CC3)C[C@H]2CNc2ncc(Cl)cc2F)n1]

3c

¹HNMR (CDCl₃) δ ppm 8.68-8.82 (m, 2 H), 8.35-8.57 (m, 1 H), 7.66-7.88 (m, 1 H), 7.11-7.32 (m, 3 H), 6.86-7.02 (m, 1 H), 4.66-4.86 (m, 1 H), 3.79-3.99 (m, 2 H), 3.40-3.48 (m, 1 H), 3.11-3.37 (m, 1 H), 2.57-2.77 (m, 4 H) 1.57-1.67 (m, 1 H) 0.44-0.72 (m, 4 H)
ESI+ m/z 454 [M + H]⁺

(S)-(6-(((5-chloro-3-fluoropyridin-2-yl)amino)methyl)-5-azaspiro[2.4]heptan-5-yl)(6-methyl-3-(pyrimidin-2-yl)pyridin-2-yl)methanone.

| | (D30) (D96) | 2 | 37 |
|---|---|---|---|

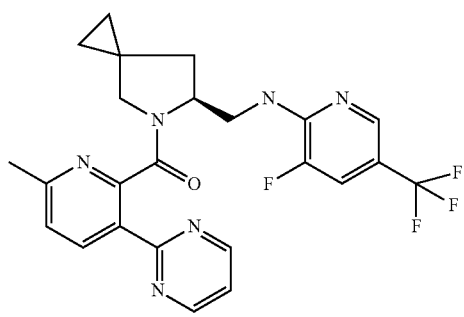 [SMILES: Cc1ccc(-c2ncccn2)c(C(=O)N2CC3(CC3)C[C@H]2CNc2ncc(C(F)(F)F)cc2F)n1]

3d

¹HNMR (CDCl₃) δ ppm 8.67-8.84 (m, 2 H), 8.32-8.58 (m, 1 H), 7.99-8.18 (m, 1 H), 7.10-7.40 (m, 4 H), 4.76-4.86 (m, 1 H), 3.86-4.02 (m, 2 H), 3.43-3.49 (m, 1 H), 3.12-3.48 (m, 1 H), 2.55-2.77 (m, 1 H), 2.38-2.44 (m, 1 H) 1.56-1.68 (m, 1 H) 0.46-0.73 (m, 4 H)
ESI+ m/z 487 [M + H]⁺

(S)-(6-(((3-fluoro-5-(trifluoromethyl)pyridin-2-yl)amino)methyl)-5-azaspiro[2.4]heptan-5-yl)(6-methyl-3-(pyrimidin-2-yl)pyridin-2-yl)-methanone.

| Comp. | Intermediate | Procedure | Yield % |
| --- | --- | --- | --- |
| (D30) | (D57) | 2 | 58 |

¹HNMR (CDCl₃) δ ppm 7.92-8.15 (m, 1 H), 7.50-7.67 (m, 1 H), 7.37-7.48 (m, 3 H), 7.23-7.30 (m, 4 H), 6.89-7.04 (m, 1 H), 4.68-4.72 (m, 1 H), 3.67-3.73 (m, 1 H), 3.45-3.53 (m, 1 H), 3.12-3.28 (m, 1 H), 2.75-2.77 (m, 1 H) 2.55-2.64 (m, 3 H) 2.06-2.13 (m, 1 H) 1.45-1.50 (m, 1 H) 0.28-0.59 (m, 4 H).
ESI+ m/z 485 [M + H]⁺

3e (S)-(6-(((3-fluoro-5-(trifluoromethyl)pyridin-2-yl)amino)methyl)-5-azaspiro[2.4]heptan-5-yl)(6-methyl-3-phenylpyridin-2-yl)methanone.

| | | | |
| --- | --- | --- | --- |
| (D27) | (D97) | 2 | 67 |

¹HNMR (DMSO) δ ppm 7.96-8.29 (m, 1 H), 7.74-7.81 (m, 1 H), 6.65-7.68 (m, 8 H), 3.74-4.30 (m, 1 H), 3.43-3.61 (m, 1 H), 3.31-3.61 (m, 2 H under the solvent peak), 2.75-3.14 (m, 2 H), 2.08-2.47 (m, 3 H), 1.52-1.99 (m, 1 H) 1.26-1.32 (m, 1 H) 0.34-0.62 (m, 4 H).
ESI+ m/z 484-486 [M + H]⁺

3f (S)-(3-(4-fluorophenyl)-6-methylpyridin-2-yl)(6-(((5-(trifluoromethyl)pyridin-2-yl)amino)methyl)-5-azaspiro[2.4]heptan-5-yl)methanone.

| | | | |
| --- | --- | --- | --- |
| (D31) | (D96) | 2 | 27 |

¹HNMR (DMSO) δ ppm 8.80-8.90 (m, 2 H), 8.36 (s, 1 H), 7.90-7.96 (m, 1 H) 7.68-7.78 (m, 1 H), 7.35-7.46 (m, 2 H), 4.54-4.80 (m, 1 H) 3.87-4.09 (m, 2 H), 3.24-3.62 (m, 2 H), 2.55-2.79 (m, 6 H), 2.32-2.46 (m, 1 H), 1.61-179 (m, 1 H), 0.55-0.82 (m, 4 H).
ESI+ m/z 502-505 [M + H]⁺

3g (S)-(6-(((3-chloro-5-(trifluoromethyl)pyridin-2-yl)amino)methyl)-5-azaspiro[2.4]heptan-5-yl)(6-methyl-3-(pyrimidin-2-yl)pyridin-2-yl)-methanone.

| Comp. | Intermediate | Procedure | Yield % |
| --- | --- | --- | --- |
| (D32) | (D96) | 2 | 33 |

¹HNMR (DMSO) δ ppm 8.38-8.93 (m, 3 H), 8.03-8.08 (m, 1 H), 7.35-7.67 (m, 3 H), 4.54-4.71 (m, 1 H), 3.87-3.99 (m, 2 H), 3.50-3.62 (m, 1 H), 3.18-3.26 (m, 1 H), 2.77-2.80 (m, 3 H), 2.55-2.59 (m, 2 H, under the solvent peak), 2.36-2.42 (m, 1 H), 1.56-1.80 (m, 1 H), 0.52-0.81 (m, 4 H).
ESI+ m/z 470 [M + H]⁺

3h (S)-(6-methyl-3-(pyrimidin-2-yl)pyridin-2-yl)(6-(((5-(trifluoromethyl)pyrazin-2-yl)amino)methyl)-5-azaspiro[2.4]heptan-5-yl)methanone.

| | (D27) | (D99) | 2 | 78 |
| --- | --- | --- | --- | --- |

¹HNMR (Acetone-d6) δ ppm 8.07-8.33 (m, 1 H), 7.81-7.95 (m, 2 H), 7.49-7.68 (m, 1 H), 7.32-7.45 (m, 2 H), 6.94-7.01 (m, 1 H), 6.21-6.72 (m, 1 H), 4.40-4.60 (m, 1 H), 3.64-3.85 (m, 2 H), 3.38-3.52 (m, 1 H), 3.05-3.23 (m, 1 H), 2.76-2.80 (m, 3 H), 2.50-2.56 (m, 3 H), 2.19-2.28 (m, 1 H), 1.52-1.76 (m, 1 H), 0.48-0.78 (m, 4 H).
ESI+ m/z 470-472 [M + H]⁺

3i (S)-(6-methyl-3-(4-methyl-1H-pyrazol-1-yl)pyridin-2-yl)(6-(((5-(trifluoromethyl)pyridin-2-yl)amino)-methyl)-5-azaspiro[2.4]heptan-5-yl)-methanone.

| | (D27) | (D98) | 2 | 80 |
| --- | --- | --- | --- | --- |

¹HNMR (Acetone-d6) δ ppm 8.07-8.32 (m, 1 H), 7.91-7.96 (m, 2 H), 7.37-7.66 (m, 2 H), 7.32-7.45 (m, 2 H), 6.94-7.01 (m, 1 H), 6.21-6.72 (m, 1 H), 4.40-4.60 (m, 1 H), 3.64-3.85 (m, 2 H), 3.38-3.52 (m, 1 H), 3.05-3.23 (m, 1 H), 2.76-2.80 (m, 3 H), 2.50-2.56 (m, 3 H), 2.19-2.28 (m, 1 H), 1.52-1.76 (m, 1 H), 0.48-0.78 (m, 4 H).
ESI+ m/z 470-472 [M + H]⁺

3j (S)-(6-methyl-3-(3-methyl-1H-pyrazol-1-yl)pyridin-2-yl)(6-(((5-(trifluoromethyl)pyridin-2-yl)amino)-methyl)-5-azaspiro[2.4]heptan-5-yl)-methanone.

| Comp. | Intermediate | Procedure | Yield % |
|---|---|---|---|
| | (D27) (D66) | 2 | 86 |

3k

¹HNMR (CDCl₃) δ ppm 8.13-8.30 (m, 1 H), 7.01-7.52 (m, 9 H), 6.09-6.61 (m, 1 H), 5.10-5.14 (m, 2 H), 4.74-4.82 (m, 1 H), 3.52-3.83 (m, 2 H), 3.14-3.38 (m, 2 H), 2.49-2.52 (m, 3 H), 2.26-2.33 (m, 1 H) 1.42-1.66 (m, 1 H), 0.44-0.71 (m, 4 H)
ESI+ m/z 497 [M + H]⁺

(S)-(3-(benzyloxy)-6-methylpyridin-2-yl)(6-(((5-(trifluoromethyl)pyridin-2-yl)amino)methyl)-5-azaspiro[2.4]heptan-5-yl)methanone.

| | (D27) (D68) | 2 | 97 |
|---|---|---|---|

3l

¹HNMR (CDCl₃) δ ppm 8.13-8.33 (m, 1 H), 7.39-7.48 (m, 1 H), 7.15-7.29 (m, 2 H), 7.02-7.13 (m, 2 H), 6.89-6.95 (m, 1 H), 6.67-6.73 (m, 1 H), 6.12-6.48 (m, 1 H), 5.11-5.21 (m, 2 H), 4.81-4.84 (m, 1 H), 3.98-4.07 (m, 2 H), 3.72-3.76 (m, 1 H), 3.35-3.38 (m, 1 H), 3.14-3.17 (m, 1 H), 2.50-2.54 (m, 3 H), 2.29-2.34 (m, 1 H), 1.59-1.63 (m, 1 H), 0.48-0.73 (m, 4 H).
ESI+ m/z 533 [M + H]⁺

(S)-(3-((2,3-difluorobenzyl)oxy)-6-methylpyridin-2-yl)(6-(((5-(trifluoromethyl)pyridin-2-yl)amino)methyl)-5-azaspiro[2.4]heptan-5-yl)-methanone.

| | (D27) (D70) | 2 | 71 |
|---|---|---|---|

3m

¹HNMR (CDCl₃) δ ppm 8.13-8.34 (m, 1 H), 7.39-7.50 (m, 1 H), 7.29-7.33 (m, 2 H), 7.12-7.24 (m, 2 H), 6.95-7.09 (m, 2 H), 6.64-6.69 (m, 1 H), 6.09-6.48 (m, 1 H), 5.05-5.09 (m, 2 H), 4.29-4.85 (m, 1 H), 3.72-3.75 (m, 1 H), 3.14-3.40 (m, 2 H), 2.49-2.53 (m, 3 H), 2.25-2.32 (m, 1 H), 1.41-1.65 (m, 1 H), 0.47-0.72 (m, 4 H).
ESI+ m/z 515 [M + H]⁺

(S)-(3((4-fluorobenzyl)oxy)-6-methylpyridin-2-yl)(6-(((5-(trifluoromethyl)pyridin-2-yl)amino)methyl)-5-azaspiro[2.4]heptan-5-yl)methanone.

| | (D27) (D72) | 2 | 87 |
|---|---|---|---|

3n

¹HNMR (CDCl₃) δ ppm 8.13-8.34 (m, 1 H), 7.46-7.54 (m, 1 H), 7.33-7.40 (m, 1 H), 7.26-7.28 (m, 1 H), 7.15-7.17 (m, 1 H), 6.71-6.90 (m, 2 H), 6.65-6.70 (m, 1 H), 6.11-6.47 (m, 1 H), 5.04-5.14 (m, 2 H), 4.31-4.86 (m, 1 H), 3.54-3.73 (m, 2 H), 3.34-3.36 (m, 1 H), 3.14-3.16 (m, 1 H), 2.50-2.53 (m, 3 H), 2.28-2.33 (m, 1 H), 1.59-1.53 (m, 1 H), 0.49-0.73 (m, 4 H).
ESI+ m/z 533 [M + H]⁺

(S)-(3-((2,4-difluorobenzyl)oxy)-6-methylpyridin-2-yl)(6-(((5-(trifluoromethyl)pyridin-2-yl)amino)methyl)-5-azaspiro[2.4]heptan-5-yl)-methanone.

| Comp. | Intermediate | Procedure | Yield % |
|---|---|---|---|
| (D27) | (D74) | 2 | 89 |

¹HNMR (CDCl₃) δ ppm = 8.13-8.32 (m, 1 H), 7.41-7.50 (m, 1 H), 7.03-7.21 (m, 2 H), 6.89-6.98 (m, 2 H), 6.70-6.77 (m, 1 H), 6.56-6.64 (m, 1 H), 6.14-6.52 (m, 1 H), 5.07-5.10 (m, 2 H), 4.32-4.84 (m, 1 H), 3.58-3.81 (m, 1 H), 3.36-3.41 (m, 2 H), 3.19-3.22 (m, 1 H), 2.50-2.53 (m, 3 H), 2.29-2.36 (m, 1 H), 1.66-1.69 (m, 1 H), 0.49-0.76 (m, 4 H).
ESI+ m/z 533 [M + H]⁺

3o (S)-(3-((3,5-difluorobenzyl)oxy)-6-methylpyridin-2-yl)(6-(((5-(trifluoromethyl)pyridin-2-yl)amino)methyl)-5-azaspiro[2.4]heptan-5-yl)-methanone.

| | (D42) | (D96) | 2 | 13 |
|---|---|---|---|---|

¹H NMR (Acetone) δ ppm = 8.98-8.74 (m, 1 H), 8.69-8.46 (m, 2 H), 8.42-7.70 (m, 2 H), 7.54-6.85 (m, 4 H), 5.00-4.65 (m, 1 H), 4.18-3.13 (m, 4 H), 2.68-2.12 (m, 4 H), 1.94-1.48 (m, 1 H), 1.20-0.44 (m, 4 H)
ESI+ m/z 639 [M + H]⁺

3p (S)-(6-(((1,6-naphthyridin-5-yl)amino)methyl)-5-azaspiro[2.4]heptan-5-yl)(6-methyl-3-(pyrimidin-2-yl)pyridin-2-yl)methanone

| | (D27) | (D100) | 2 | 26 |
|---|---|---|---|---|

¹H NMR (CDCl3) δ ppm = 8.42-8.11 (m, 1 H), 8.10-7.69 (m, 2 H), 7.58-7.22 (m, 3 H), 7.10-6.76 (m, 1 H), 6.73-6.37 (m, 1 H), 5.96 (d, J = 8.3 Hz, 1 H), 4.94-4.60 (m, 1 H), 4.08-2.99 (m, 4 H), 2.56-2.23 (m, 2 H), 1.85-1.15 (m, 3 H), 0.88-0.29 (m, 4 H)
ESI+ m/z 474 [M + H]⁺

3q (S)-(6-methyl-3-(thiazol-2-yl)pyridin-2-yl)(6-(((5-(trifluoromethyl)pyridin-2-yl)amino)methyl)-5-azaspiro[2.4]heptan-5-yl)methanone.

| Comp. | Intermediate | Procedure | Yield % |
|---|---|---|---|
| (D27) | (D95) | 2 | 16 |

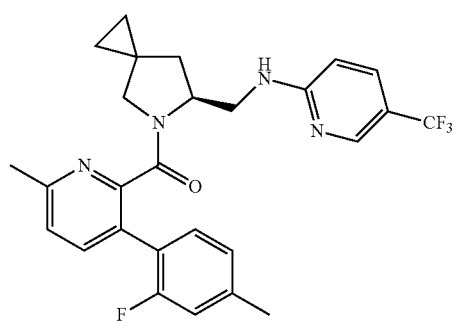 [SMILES: Cc1ccc(-c2ccc(C)nc2C(=O)N2CC3(CC3)C[C@H]2CNc2ccc(C(F)(F)F)cn2)c(F)c1]

3r (S)-(6-cyclopropyl-3-phenylpyridin-2-yl)(6-(((5-(trifluoromethyl)pyridin-2-yl)amino)methyl)-5-azaspiro[2.4]heptan-5-yl)methanone ¹H NMR (CDCl3) δ ppm = 8.34-8.18 (m, 1 H), 7.62-7.54 (m, 1 H), 7.54-7.51 (m, 1 H), 7.45-7.41 (m, 2 H), 7.30-7.20 (m, 4 H), 6.43-6.41 (m, 2 H), 4.71-4.65 (m, 1 H), 3.54-3.28 (m, 2 H), 3.16-3.13 (m, 1 H), 2.85-2.83 (m, 1 H), 2.16-2.07 (m, 2 H), 1.13-1.03 (m, 4 H), 0.55-0.36 (m, 4 H).
ESI+ m/z 493 [M + H]+

Example 4

Preparation of Compound 4

(S)-(3-(2-fluoro-4-methylphenyl)-6-methylpyridin-2-yl)(6-(((5-(trifluoromethyl)pyridin-2-yl)amino)methyl)-5-azaspiro[2.4]heptan-5-yl)methanone. (E4)

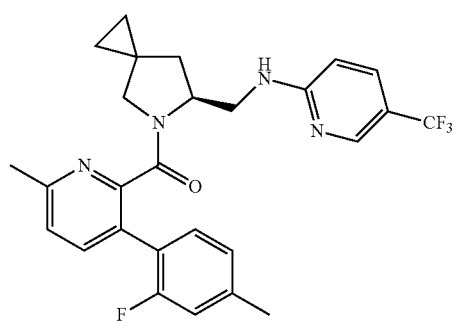 [SMILES: Cc1ccc(-c2ccc(C)nc2C(=O)N2CC3(CC3)C[C@H]2CNc2ccc(C(F)(F)F)cn2)c(F)c1]

To a suspension of (D47) (30 mg, 0.058 mmol), (2-fluoro-4-methylphenyl) boronic acid (8.93 mg, 0.058 mmol) and Tetrakistriphenylphosphine palladium (6.7 mg, 0.0058 mmol) in toluene (0.55 ml), an aqueous solution of K₂CO₃ (1M; 58 μl, 0.058 mmol) was added. The mixture was heated at 130° C. (microwave) for 1 h (6×10' cycles), then poured in water and extracted with AcOEt (3×10 ml); organics were evaporated to obtain a crude mixture which was purified on silica gel (DCM to AcOEt). Yield 20 mg.

MS (ESI) m/z: 499 [M+H]+.

¹HNMR (CDCl₃) δ ppm=8.16 (bs, 1H), 7.85-7.98 (m, 2H), 7.42-7.51 (m, 1H), 7.26-7.30 (m, 2H), 7.01-7.08 (m, 2H), 4.28-4.47 (m, 1H), 3.75-3.89 (m, 1H), 3.62-3.67 (m, 1H), 3.30-3.32 (m, 1H), 2.97-3.12 (m, 1H), 2.69-2.81 (m, 3H), 2.43 (s, 3H), 2.14-2.20 (m, 1H), 1.65-1.69 (m, 1H), 0.85-0.92 (m, 1H), 0.43-0.73 (m, 4H).

Example 5

Preparation of Compound 5

(S)-(3-phenylpyridin-2-yl)(6-(((5-(trifluoromethyl)pyridin-2-yl)amino)methyl)-5-azaspiro[2.4]heptan-5-yl)methanone. (E5)

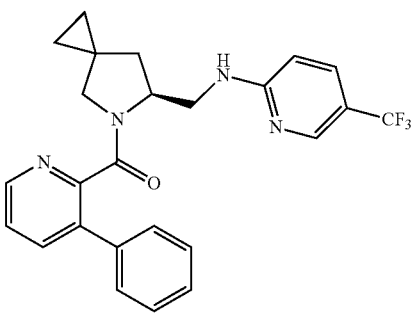 [SMILES: O=C(c1ncccc1-c1ccccc1)N1CC2(CC2)C[C@H]1CNc1ccc(C(F)(F)F)cn1]

To a suspension of (D48) (35 mg, 0.077 mmol), phenyl boronic acid (14 mg, 0.11 mmol) and Tetrakistriphenylphosphine palladium (4.5 mg, 0.00383 mmol) in toluene (0.5 ml) and water (0.1 ml), K₂CO₃ (16 mg, 0.11 mmol) was added. The mixture was heated at 130° C. (microwave) for 30', then poured in water and extracted with AcOEt (3×10 ml); organics were evaporated to obtain a crude mixture which was purified on silica gel (DCM to AcOEt). Yield 17 mg.

MS (ESI) m/z: 453-454 [M+H]+.

¹HNMR (CDCl₃) δ ppm=8.49-8.65 (m, 1H), 8.12-8.32 (m, 1H), 7.69-7.81 (m, 1H), 7.26-7.56 (m, 7H), 6.59-6.65 (m, 1H), 6.22-6.52 (m, 1H), 4.62-4.68 (m, 1H), 3.33-3.58 (m, 2H), 3.14-3.16 (m, 1H), 2.85-2.88 (m, 1H), 2.07-2.12 (m, 1H), 1.52-1.57 (m, 1H), 0.37-0.62 (m, 4H).

Example 6

Preparation of Compound 6

(S)-(6-methyl-[3,3'-bipyridin]-2-yl)(6-(((5-(trifluoromethyl)pyridin-2-yl)amino)methyl)-5-azaspiro[2.4]heptan-5-yl)methanone. (E6)

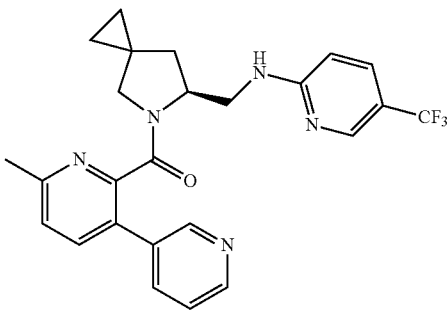 [SMILES: Cc1ccc(-c2cccnc2)c(C(=O)N2CC3(CC3)C[C@H]2CNc2ccc(C(F)(F)F)cn2)n1]

To a suspension of (D47) (26 mg, 0.05 mmol), pyridin-3-ylboronic acid (10 mg, 0.075 mmol) and Tetrakistriphenylphosphine palladium (1 mg, 0.001 mmol) in toluene (0.4 ml) and water (0.1 ml), $K_2CO_3$ (11 mg, 0.075 mmol) was added. The mixture was heated at 130° C. (microwave) for 1 h (2×30' cycles), then poured in water and extracted with AcOEt (3×10 ml); organics were evaporated to obtain a crude mixture which was purified on silica gel (DCM to AcOEt). Yield 7 mg.

MS (ESI) m/z: 468 [M+H]$^+$.

$^1$HNMR (Acetone d$_6$) δ ppm=8.70-8.94 (m, 1H), 8.57-8.66 (m, 1H), 8.09-8.31 (m, 1H), 7.85-7.92 (m, 2H), 7.50-7.67 (m, 1H), 7.37-7.46 (m, 2H), 6.74-6.79 (m, 1H), 6.34-6.70 (m, 1H), 4.0-4.53 (m, 1H), 3.58-3.69 (m, 2H), 3.29-3.34 (m, 1H), 3.02-3.20 (m, 1H), 2.58 (s, 3H), 2.10-2.16 (m, 1H), 1.62-1.73 (m, 1H), 0.42-0.71 (m, 4H).

Example 7

Preparation of Compound 7

(S)-[2,3'-bipyridin]-2'-yl(6-(((5-(trifluoromethyl)pyridin-2-yl)amino)methyl)-5-azaspiro[2.4]heptan-5-yl)methanone. (E7)

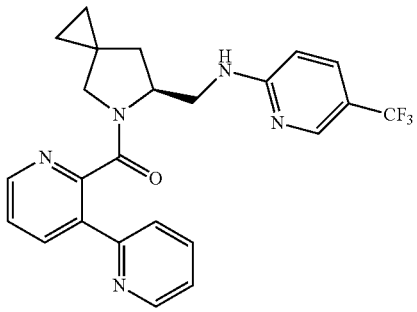 [SMILES: O=C(c1ncccc1-c1ccccn1)N1CC2(CC2)C[C@H]1CNc1ccc(C(F)(F)F)cn1]

A suspension of (D48) (40 mg, 0.088 mmol), 2-(tributylstannyl)pyridine (52 mg, 0.143 mmol), Tetrakistriphenylphosphine palladium (10 mg, 0.001 mmol), CsF (27 mg, 0.176 mmol) and CuI (3.4 mg, 0.0176 mmol) in DMF (1 ml) was heated at 130° C. (microwave) for 10' then poured in water and extracted with DCM (3×10 ml); organics were evaporated to obtain a crude that was purified on silica gel (DCM to DCM/MeOH=95/5). Yield 14 mg.

MS (ESI) m/z: 454 [M+H]$^+$.

$^1$HNMR (Acetone d$_6$) δ ppm=8.55-8.72 (m, 2H), 8.09-8.33 (m, 2H), 7.85-7.97 (m, 1H), 7.75-7.80 (m, 1H), 7.54-7.64 (m, 1H), 7.33-7.49 (m, 2H), 7.02 (bs, 1H), 6.19-6.67 (m, 1H), 4.51-4.59 (m, 1H), 3.69-3.84 (m, 2H), 3.50-3.62 (m, 1H), 3.16-3.24 (m, 1H), 2.23-2.31 (m, 1H), 1.55-1.78 (m, 1H), 0.52-0.79 (m, 4H).

Example 8

Preparation of Compound 8

(S)-4-(6-methyl-2-(6-(((5-(trifluoromethyl)pyridin-2-yl)amino)methyl)-5-azaspiro[2.4]heptane-5-carbonyl)pyridin-3-yl)benzonitrile (E8)

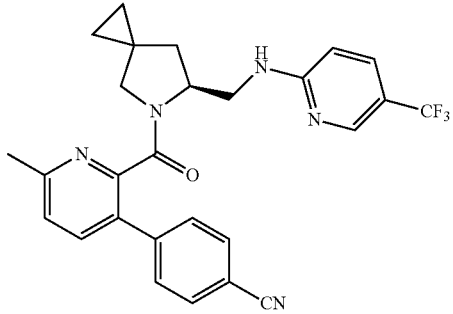 [SMILES: Cc1ccc(-c2ccc(C#N)cc2)c(C(=O)N2CC3(CC3)C[C@H]2CNc2ccc(C(F)(F)F)cn2)n1]

To a suspension of (D47) (26 mg, 0.05 mmol), 4-cyanophenyl boronic acid (11 mg, 0.075 mmol) and Tetrakistriphenylphosphine palladium (1 mg, 0.001 mmol) in toluene (0.4 ml) and water (0.1 ml), $K_2CO_3$ (11 mg, 0.075 mmol) was added. The mixture was heated at 130° C. (microwave) for 1 h (2×30' cycles), then poured in water and extracted with AcOEt (3×10 ml); organics were evaporated to obtain a crude mixture that was purified on silica gel (DCM to AcOEt). Yield 7 mg.

MS (ESI) m/z: 492 [M+H]$^+$.

$^1$HNMR (CDCl$_3$) δ ppm=8.13-8.34 (m, 1H), 7.46-7.76 (m, 6H), 7.18-7.34 (m, 1H), 6.88 (bs, 1H), 6.23-6.59 (m, 1H), 4.60-4.66 (m, 1H), 3.59-3.70 (m, 2H), 3.22-3.29 (m, 1H), 2.93-2.96 (m, 1H), 2.62-2.65 (m, 3H), 2.12-2.17 (m, 1H), 1.40-1.65 (m, 1H), 0.39-0.70 (m, 4H).

Example 9

Preparation of Compound 9

(S)-(6-((benzo[d]oxazol-2-ylamino)methyl)-5-azaspiro[2.4]heptan-5-yl)(6-methyl-3-(pyrimidin-2-yl)pyridin-2-yl)methanone (E9

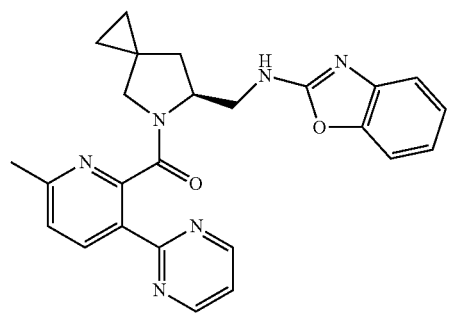 [SMILES: Cc1ccc(-c2ncccn2)c(C(=O)N2CC3(CC3)C[C@H]2CNc2nc3ccccc3o2)n1]

(D52) (10 mg, 0.031 mmol), $K_2CO_3$ (9 mg, 0.065 mmol) and 2-chlorobenzo[d]oxazole (6 μl, 0.052 mmol) are dissolved in DMF (300 μl) and heated at 60° C. (microwave) for 15'. The reaction was diluted with DCM (10 ml), washed with brine and water, dried and evaporated. Crude was purified on flash silica column (Cyclohexane/AcOEt=1/1 to AcOEt to AcOEt/MeOH=9/1). Title compound is obtained as a white solid (6 mg).

MS (ESI) m/z: 441 [M+H]+.
¹HNMR (CDCl₃) δ ppm=8.32-8.87 (m, 3H), 7.02-7.51 (m, 7H), 4.85 (bs, 1H), 3.88-4.22 (m, 2H), 3.38-3.46 (m, 1H), 3.17-3.20 (m, 1H), 2.70 (bs, 3H), 2.40-2.57 (m, 1H), 1.59-1.86 (m, 1H), 0.46-0.78 (m, 4H).

Example 10

Preparation of Compound 10

(S)-(6-(((5-chlorobenzo[d]oxazol-2-yl)amino)methyl)-5-azaspiro[2.4]heptan-5-yl)(6-methyl-3-(pyrimidin-2-yl)pyridin-2-yl)methanone (E10)

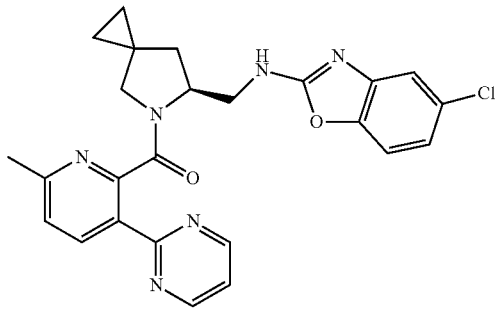 [SMILES: Cc1ccc(-c2ncccn2)c(C(=O)N2CC3(CC3)C[C@H]2CNc2nc3cc(Cl)ccc3o2)n1]

(D52) (22 mg, 0.068 mmol), K₂CO₃ (18 mg, 0.085 mmol) and 2,5-dichlorobenzo[d]oxazole (16 mg, 0.085 mmol, prepared according to J. Med. Chem. 1994, 37, 913-923.) are dissolved in DMF (0.5 ml) and heated at 80° C. for 1 hour. The reaction was diluted with AcOEt, washed with brine and water, dried and evaporated. Crude was purified on C18 column (Isco Redisep, 15 g) eluting with a gradient from H₂O (+acetic acid 0.1%)/CH₃CN (+acetic acid 0.1%)=9/1 to CH₃CN (+acetic acid 0.1%). Fractions were evaporated, treated with a saturated solution of NaHCO₃ and extracted with DCM. Title compound was obtained as a white solid (16 mg).

MS (ESI) m/z: 475 [M+H]+ Chlorine pattern.
¹HNMR (Acetone d₆) δ ppm=8.66-8.94 (m, 2H), 8.38-8.56 (m, 1H), 7.74-7.81 (m, 1H), 7.44-7.48 (m, 1H), 7.32-7.39 (m, 1H), 7.26-7.28 (m, 1H), 7.14-7.17 (m, 1H), 6.96-7.03 (m, 1H), 4.61-4.64 (m, 1H), 3.85-4.01 (m, 2H), 3.51-3.60 (m, 1H), 3.19-3.28 (m, 1H), 2.55-2.58 (m, 3H), 2.37-2.50 (m, 1H), 1.62-1.84 (m, 1H), 0.52-0.86 (m, 4H).

Example 11

Preparation of Compound 11

(S)-(3-(3,4-difluorophenyl)-6-methylpyridin-2-yl)(6-(((5-(trifluoromethyl)pyridin-2-yl)amino)methyl)-5-azaspiro[2.4]heptan-5-yl)methanone (E11)

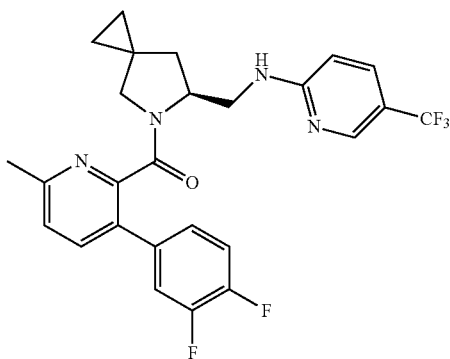 [SMILES: Cc1ccc(-c2ccc(F)c(F)c2)c(C(=O)N2CC3(CC3)C[C@H]2CNc2ccc(C(F)(F)F)cn2)n1]

To a suspension of (D47) (26 mg, 0.05 mmol), 3,4-difluoro-phenyl boronic acid (12 mg, 0.075 mmol) and Tetrakistriphenylphosphine palladium (1 mg, 0.001 mmol) in toluene (0.4 ml) and water (0.1 ml), K₂CO₃ (11 mg, 0.075 mmol) was added. The mixture was heated at 130° C. (microwave) for 1 h (2×30' cycles), then poured in water and extracted with AcOEt (3×10 ml); organics were evaporated to obtain a crude that was purified on silica gel (DCM to DCM/MeOH=95/5). Yield 7 mg.

MS (ESI) m/z: 503 [M+H]+
¹HNMR (CDCl₃) δ ppm=8.13-8.34 (m, 1H), 7.44-7.72 (m, 3H), 7.13-7.30 (m, 2H), 6.99-7.06 (m, 1H), 5.63-6.48 (m, 2H), 3.88-4.70 (m, 1H), 3.58-3.61 (m, 1H), 3.19-3.30 (m, 1H), 2.92-2.95 (m 1H), 2.60-2.64 (m, 3H), 2.12-2.17 (m, 1H), 1.48-1.62 (m, 1H), 0.39-0.67 (m, 4H).

Example 12

Preparation of Compound 12

(S)-4-(pyrimidin-2-yl)-3-(6-(((5-(trifluoromethyl)-pyridin-2-yl)amino)methyl)-5-azaspiro[2.4]heptane-5-carbonyl)benzonitrile (E12)

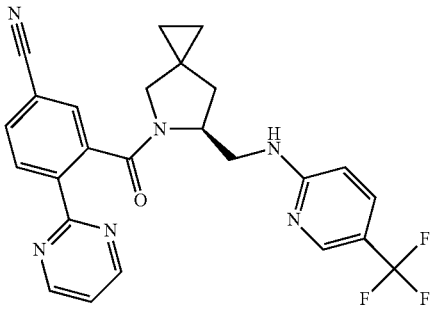 [SMILES: N#Cc1ccc(-c2ncccn2)c(C(=O)N2CC3(CC3)C[C@H]2CNc2ccc(C(F)(F)F)cn2)c1]

To a solution of (Example 1e) (20 mg, 0.037 mmol), potassium hexacyanoferrate (3 mg; 0.009 mmol), palladium (II) acetate (1 mg, 0.001 mmol) in DMF (1.5 ml), Na₂CO₃ (5 mg, 0.047 mmol) was added. The mixture was heated at 120° C. in a sealed tube for 18 h, then poured in water and extracted with DCM (3×10 ml); organics were evaporated to obtain a crude that was purified on silica gel (Cyclohexane/AcOEt=8/2). Yield 1.28 mg.

MS (ESI) m/z: 479 [M+H]+
¹H NMR (Acetone) δ ppm=9.01-8.40 (m, 3H), 8.37-8.01 (m, 1H), 8.00-7.42 (m, 4H), 7.04-6.67 (m, 1H), 4.66 (d, J=4.4 Hz, 1H), 3.99-3.09 (m, 4H), 2.38-2.24 (m, 1H), 1.87-1.42 (m, 1H), 0.99-0.40 (m, 5H).

Example 13

Biological Section

In a typical experiment, the antagonistic activity against human OX1 and OX2 receptors is determined by using CHO e HEK-293 cells transfected with human recombinant OX1 and OX2 receptors respectively, seeded at density of 2 and 3×10⁴ cells/well respectively in a 96 fluorimetry well plate. Thus the plate was loaded with the calcium dye (Fluo-4NW/probenecid in HBSS, Hepes 20 mM, pH 7.4; Invitrogen) at 37° C. for 60 min. Afterward the temperature was equilibrated at 22° C. for 15 min and the [Ca2+]i measured directly on the plate by using a fluorescent plate reader (CellLux Perkin Elmer).

Invention compounds were dissolved in DMSO, diluted in HBSS (DMSO, 0.3% final) and added to the wells. After 5 min CHO cells were activated with orexin-A, 3 nM while HEK-293 cells were activated with orexin-B, 10 nM.

The compounds, dissolved in DMSO and diluted in the medium (DMSO, 0.3% final), have been analysed in the 1 nM-1 µM concentration range (every concentration in duplicate). The antagonistic activity has been expressed as pKb (co-logarithm of the apparent dissociation constant calculated by using the modified Cheng Prusoff equation).

The results are expressed as percent of control specific antagonist response ((measured specific response/control specific agonist response)×100) obtained in the presence of the test compounds.

The $IC_{50}$ values (concentration causing a half-maximal inhibition of the control specific agonist response) were determinated by non-linear regression analysis of the concentration curves generated with mean replicate values using hill equation curve fitting. The $IC_{50}$ values are obtained by the arithmetical mean of at least two experiments. Compounds of the following example tested according to this example gave pKbs as follows:

| Compound | pKb OX1 | pKb OX2 |
|---|---|---|
| 1a | 8.1 | 7.2 |
| 1b | 7.1 | 7.2 |
| 1c | 7.9 | 6.7 |
| 1d | 6.7 | 7.1 |
| 1e | 8.5 | 7.7 |
| 1f | 8.1 | 7.9 |
| 1g | 8.9 | 7.4 |
| 1h | 7.4 | 7.9 |
| 1i | 8.2 | 7.3 |
| 1j | 7.7 | 8.2 |
| 1k | 7.3 | 8.1 |
| 1l | 8.3 | 7.6 |
| 1m | 7.8 | 7.9 |
| 1n | 7.3 | 7.8 |
| 1o | 8.7 | 6.6 |
| 1p | 7.1 | 7.7 |
| 1q | 7.4 | 8.2 |
| 1r | 8.2 | 8.0 |
| 1s | 7.6 | 7.0 |
| 1t | 8.1 | 7.7 |
| 1u | 7.8 | 6.7 |
| 1v | 8.2 | 8.0 |
| 2a | 8.3 | 7.1 |
| 2b | 9.1 | 8.6 |
| 2c | 7.3 | 7.6 |
| 2d | 8.4 | 7.7 |
| 2e | 8.6 | 8.6 |
| 2f | 7.5 | 8.6 |
| 2g | 6.8 | 6.8 |
| 2h | 8.4 | 8.2 |
| 2i | 7.9 | 7.5 |
| 2j | 8.2 | 8.5 |
| 2k | 7.8 | 8.6 |
| 3a | 8.4 | 7.5 |
| 3b | 8.6 | 8.0 |
| 3c | 8.2 | 7.4 |
| 3d | 8.4 | 8.0 |
| 3e | 8.4 | 8.1 |
| 3f | 8.1 | 8.1 |
| 3g | 8.3 | 8.0 |
| 3h | 8.2 | 7.4 |
| 3i | 8.9 | 8.3 |
| 3j | 8.9 | 7.8 |
| 3k | 8.6 | 8.6 |
| 3l | 7.6 | 8.1 |
| 3m | 7.4 | 7.8 |
| 3n | 7.1 | 7.1 |
| 3o | 8.2 | 8.3 |
| 3p | 6.9 | 7.6 |
| 3q | 8.6 | 8.0 |
| 3r | 8.6 | 7.9 |
| E4 | 7.4 | 7.5 |
| E5 | 8.0 | 7.3 |
| E6 | 7.0 | 6.7 |
| E7 | 8.4 | 6.9 |
| E8 | 7.7 | 7.5 |
| E9 | 9.2 | 7.6 |
| E10 | 8.1 | 7.1 |
| E11 | 7.9 | 7.7 |
| E12 | 8.0 | 8.1 |

Example 13

Comparison Data with Compounds Disclosed in WO2011006960

Compound 51 disclosed in WO2011006960 is compared with Examples 1o and 1n of the present invention. It is evident that the specific substitution on the phenyl ring changes the activity of the compounds at the OX2 Receptor.

| Example | pKb OX1 | pKb OX2 |
|---|---|---|
| 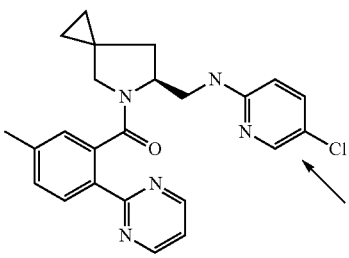 [SMILES: Cc1ccc(-c2ncccn2)c(C(=O)N2CC3(CC3)C[C@H]2CNc2ccc(Cl)cn2)c1] Example 51 of WO2011006960 | 8.2 | <5.0 |
| 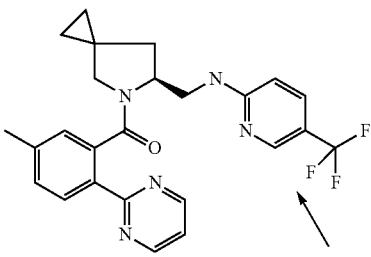 [SMILES: Cc1ccc(-c2ncccn2)c(C(=O)N2CC3(CC3)C[C@H]2CNc2ccc(C(F)(F)F)cn2)c1] Example 1o | 8.7 | 6.6 |
| 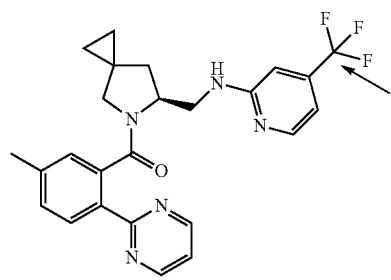 [SMILES: Cc1ccc(-c2ncccn2)c(C(=O)N2CC3(CC3)C[C@H]2CNc2cc(C(F)(F)F)ccn2)c1] Example 1n | 7.3 | 7.8 |

The invention claimed is:
1. A compound of formula (I) or a stereoisomer, a racemate, or a pharmaceutically acceptable salt thereof:

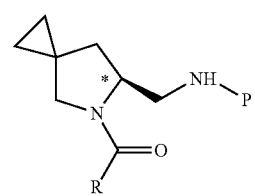

(I)

wherein:

R is phenyl or a 5- or 6-membered heteroaryl ring containing 1 to 3 heteroatoms selected from S, N, and O, such rings may be optionally substituted with n groups Q;

Q is C1-C4 alkyl, halogen, halo C1-C4 alkyl, C1-C4 alkoxy, CN, $SO_2CH_3$ or —O[$CR_1R_2$]$_p$$Q_1$; or Q may be a group $Q_2$;

$Q_1$ is phenyl, which may be optionally substituted with n substituents selected from C1-C4 alkyl, halogen, halo C1-C4 alkyl, C1-C4 alkoxy, CN, or a group $Q_2$; or $Q_1$ corresponds to 2,2-difluorobenzo[d][1,3]dioxol-4-yl;

$Q_2$ is a 5- or 6-membered heteroaryl containing at least one nitrogen atom, which may be optionally substituted with n substituents selected from C1-C4 alkyl, halogen, halo C1-C4 alkyl, C1-C4 alkoxy, or CN;

P is a 6-membered heteroaryl or a 8-11 membered bicyclic heteroaryl group, which may be substituted with n substituents selected from C1-C4 alkyl, halogen, halo C1-C4 alkyl, C1-C4 alkoxy, or CN;

$R_1$ is hydrogen or C1-C3 alkyl;

$R_2$ is hydrogen or C1-C3 alkyl;

n is 1, 2, or 3;

p is 0, 1, or 2; and with the proviso that when R corresponds to phenyl, which may be optionally substituted, P is substituted by at least one $CF_3$.

2. A compound according to claim 1, wherein the compound is a compound of formula (II)

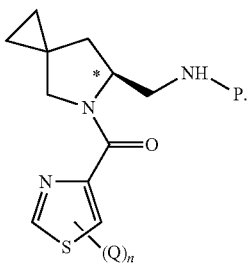

(II)

3. A compound according to claim 1, wherein the compound is a compound of formula (III)

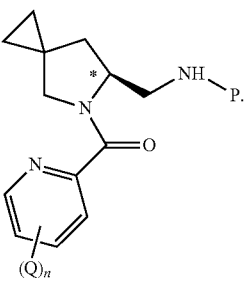

(III)

4. A compound according to claim 1, wherein the compound is a compound of formula (IV)

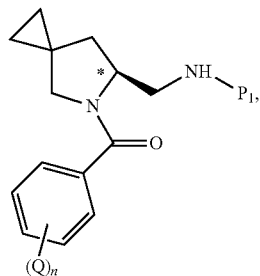

(IV)

wherein $P_1$ is pyridinyl, substituted by at least a group —$CF_3$.

5. A compound, wherein the compound is:
(S)-(6-(((5-chloropyridin-2-yl)amino)methyl)-5-azaspiro[2.4]heptan-5-yl)(2-methyl-5-phenylthiazol-4-yl)methanone;
(S)-(2-methyl-5-phenylthiazol-4-yl)(6-(((6-methylpyridin-2-yl)amino)methyl)-5-azaspiro[2.4]heptan-5-yl)methanone;
(S)-(2-methyl-5-phenylthiazol-4-yl)(6-(((5-(trifluoromethyl)pyridin-2-yl)amino)methyl)-5-azaspiro[2.4]heptan-5-yl)methanone;
(S)-(6-((isoquinolin-1-ylamino)methyl)-5-azaspiro[2.4]heptan-5-yl)(2-methyl-5-phenylthiazol-4-yl)methanone;
(S)-(6-(((4,6-dimethylpyrimidin-2-yl)amino)methyl)-5-azaspiro[2.4]heptan-5-yl)(2-methyl-5-phenylthiazol-4-yl)methanone;
(S)-(6-(((5-chloropyrimidin-2-yl)amino)methyl)-5-azaspiro[2.4]heptan-5-yl)(2-methyl-5-phenylthiazol-4-yl)methanone;
(S)-(6-methyl-3-(pyrimidin-2-yl)pyridin-2-yl)(6-(((5-(trifluoromethyl)pyridin-2-yl)amino)methyl)-5-azaspiro[2.4]heptan-5-yl)methanone;
(S)-(6-methyl-3-phenylpyridin-2-yl)(6-(((5-(trifluoromethyl)pyridin-2-yl)amino)methyl)-5-azaspiro[2.4]heptan-5-yl)methanone;
(S)-(6-(((5-chloro-3-fluoropyridin-2-yl)amino)methyl)-5-azaspiro[2.4]heptan-5-yl)(6-methyl-3-(pyrimidin-2-yl)pyridin-2-yl)methanone;
(S)-(6-(((3-fluoro-5-(trifluoromethyl)pyridin-2-yl)amino)methyl)-5-azaspiro[2.4]heptan-5-yl)(6-methyl-3-(pyrimidin-2-yl)pyridin-2-yl)methanone;
(S)-(6-(((3-fluoro-5-(trifluoromethyl)pyridin-2-yl)amino)methyl)-5-azaspiro[2.4]heptan-5-yl)(6-methyl-3-phenylpyridin-2-yl)methanone;
(S)-(3-(4-fluorophenyl)-6-methylpyridin-2-yl)(6-(((5-(trifluoromethyl)pyridin-2-yl)amino)methyl)-5-azaspiro[2.4]heptan-5-yl)methanone;
(S)-(6-(((3-chloro-5-(trifluoromethyl)pyridin-2-yl)amino)methyl)-5-azaspiro[2.4]heptan-5-yl)(6-methyl-3-(pyrimidin-2-yl)pyridin-2-yl)methanone;
(S)-(6-methyl-3-(pyrimidin-2-yl)pyridin-2-yl)(6-(((5-(trifluoromethyl)pyrazin-2-yl)amino)methyl)-5-azaspiro[2.4]heptan-5-yl)methanone;
(S)-(6-methyl-3-(4-methyl-1H-pyrazol-1-yl)pyridin-2-yl)(6-(((5-(trifluoromethyl)pyridin-2-yl)amino)methyl)-5-azaspiro[2.4]heptan-5-yl)methanone;
(S)-(6-methyl-3-(3-methyl-1H-pyrazol-1-yl)pyridin-2-yl)(6-(((5-(trifluoromethyl)pyridin-2-yl)amino)methyl)-5-azaspiro[2.4]heptan-5-yl)methanone;

(S)-(3-(benzyloxy)-6-methylpyridin-2-yl)(6-(((5-(trifluoromethyl)pyridin-2-yl)amino)methyl)-5-azaspiro[2.4]heptan-5-yl)methanone;

(S)-(6-(((6-fluorobenzo[d]thiazol-2-yl)amino)methyl)-5-azaspiro[2.4]heptan-5-yl)(2-methyl-5-phenylthiazol-4-yl)methanone;

(S)-(6-(((6-chlorobenzo[d]thiazol-2-yl)amino)methyl)-5-azaspiro[2.4]heptan-5-yl)(2-methyl-5-phenylthiazol-4-yl)methanone;

(S)-(3-((2,3-difluorobenzyl)oxy)-6-methylpyridin-2-yl)(6-(((5-(trifluoromethyl)pyridin-2-yl)amino)methyl)-5-azaspiro[2.4]heptan-5-yl)methanone;

(S)-(3-((4-fluorobenzyl)oxy)-6-methylpyridin-2-yl)(6-(((5-(trifluoromethyl)pyridin-2-yl)amino)methyl)-5-azaspiro[2.4]heptan-5-yl)methanone;

(S)-(3-((2,4-difluorobenzyl)oxy)-6-methylpyridin-2-yl)(6-(((5-(trifluoromethyl)pyridin-2-yl)amino)methyl)-5-azaspiro[2.4]heptan-5-yl)methanone;

(S)-(3-((3,5-difluorobenzyl)oxy)-6-methylpyridin-2-yl)(6-(((5-(trifluoromethyl)pyridin-2-yl)amino)methyl)-5-azaspiro[2.4]heptan-5-yl)methanone;

(S)-(2,2-difluorobenzo[d][1,3]dioxol-4-yl)(6-(((5-(trifluoromethyl)pyridin-2-yl)amino)methyl)-5-azaspiro[2.4]heptan-5-yl)methanone;

(S)-(5-chloro-2-(pyrimidin-2-yl)phenyl)(6-(((5-(trifluoromethyl)pyridin-2-yl)amino)methyl)-5-azaspiro[2.4]heptan-5-yl)methanone;

(S)-(6-((benzo[d]oxazol-2-ylamino)methyl)-5-azaspiro[2.4]heptan-5-yl)(2-methyl-5-phenylthiazol-4-yl)methanone;

(S)-(3-methyl-2-(pyrimidin-2-yl)phenyl)(6-(((5-(trifluoromethyl)pyridin-2-yl)amino)methyl)-5-azaspiro[2.4]heptan-5-yl)methanone; or (S)-(4-(methylsulfonyl)[1,1'-biphenyl]-2-yl)(6-(((5-(trifluoromethyl)pyridin-2-yl)amino)-methyl)-5-azaspiro[2.4]heptan-5-yl)methanone; or a pharmaceutically acceptable salt thereof.

6. A method for treating obesity, sleep disorders, compulsive disorders, substance abuse, or schizophrenia, comprising administering to a subject in need thereof an effective amount of a compound of any one of claims 1 to 5 or a stereoisomer, a racemate, or a pharmaceutically acceptable salt thereof.

7. A pharmaceutical composition comprising a compound of anyone of claims 1 to 5, or a pharmaceutically acceptable salt thereof and a pharmaceutically acceptable carrier.

\* \* \* \* \*